United States Patent
Driebe et al.

(10) Patent No.: US 11,345,969 B2
(45) Date of Patent: May 31, 2022

(54) SYSTEMS AND METHODS FOR THE DETECTION OF INFECTIOUS DISEASES

(71) Applicants: THE TRANSLATIONAL GENOMICS RESEARCH INSTITUTE, Phoenix, AZ (US); ARIZONA BOARD OF REGENTS ON BEHALF OF NORTHERN ARIZONA UNIVERSITY, Flagstaff, AZ (US)

(72) Inventors: Elizabeth Driebe, Flagstaff, AZ (US); Paul S. Keim, Flagstaff, AZ (US); David Engelthaler, Flagstaff, AZ (US); Jolene Bowers, Flagstaff, AZ (US); Nathan C. Nieto, Flagstaff, AZ (US)

(73) Assignees: The Translational Genomics Research Institute, Phoenix, AZ (US); Arizona Board of Regents on behalf of Northern Arizona University, Flagstaff, AZ (US)

( * ) Notice: Subject to any disclaimer, the term of this patent is extended or adjusted under 35 U.S.C. 154(b) by 471 days.

(21) Appl. No.: 16/076,608

(22) PCT Filed: Feb. 11, 2017

(86) PCT No.: PCT/US2017/017573
§ 371 (c)(1),
(2) Date: Aug. 8, 2018

(87) PCT Pub. No.: WO2017/139715
PCT Pub. Date: Aug. 17, 2017

(65) Prior Publication Data
US 2019/0040455 A1    Feb. 7, 2019

Related U.S. Application Data

(60) Provisional application No. 62/293,873, filed on Feb. 11, 2016.

(51) Int. Cl.
*C12Q 1/689* (2018.01)
*C12Q 1/6883* (2018.01)

(52) U.S. Cl.
CPC ......... *C12Q 1/689* (2013.01); *C12Q 1/6883* (2013.01); *C12Q 2600/16* (2013.01); *Y02A 50/30* (2018.01)

(58) Field of Classification Search
CPC .. C12Q 1/689; C12Q 1/6883; C12Q 2600/16; Y02A 50/30
See application file for complete search history.

(56) References Cited

U.S. PATENT DOCUMENTS

| 2014/0010835 A1 | 1/2014 | Comstedt et al. |
| 2015/0203900 A1 | 7/2015 | Hung et al. |

FOREIGN PATENT DOCUMENTS

| CN | 104293960 | * | 6/2015 |
| WO | WO 9634106 | * | 10/1996 |
| WO | 2014197607 A1 | | 12/2014 |
| WO | WO 2014197607 | * | 12/2014 |
| WO | 2015070187 A2 | | 5/2015 |

OTHER PUBLICATIONS

Bacon et al., Journal of Clinical Microbiology, vol. 42, No. 5, pp. 2326-2328, May (Year: 2004).*
Wormser, G. P., et al. The clinical assessment, treatment, and prevention of lyme disease, human granulocytic anaplasmosis, and babesiosis: clinical practice guidelines by the Infectious Diseases Society of America. Clin Infect Dis 2006; 43(9):1089-1134.
Steere, A. C., et al. Elucidation of Lyme arthritis. Nat Rev Immunol 2004; 4(2): 143-152.
Lawson, J. P., et al. Lyme arthritis: radiologic findings. Radiology 1985; 154(1):37-43.
Liang, F. T., et al. Protective niche for Borrelia burgdorferi to evade humoral immunity .Am J Pathol, 2004; 165 (3):977-985.
Oosting, M., et. al. Innate immunity networks during infection with Borrelia burgdorferi. Critical Reviews in Microbiology 2016; 42(2):233-244.
Coburn, J., et. al. Illuminating the roles of the Borrelia burgdorferi adhesins. Trends in Microbiology, 2013; 21(8):372-379.
Chamberlin, M., et al. New RNA polymerase from *Escherichia coli* infected with bacteriophage T7. Nature 1970; 228:227-231.
Wu, D. Y., et al. The ligation amplification reaction (LAR)-amplification of specific DNA sequences using sequential rounds of template-dependent ligation. Genomics 1989; 4:560-569.
Jones, J. M., et al. Tick-Borne Relapsing Fever Outbreak among a High School Football Team at an Outdoor Education Camping trip, Arizona, 2014. Am. J. Trop. Med. Hyg., 2016; 95(3):546-550.

* cited by examiner

*Primary Examiner* — Cynthia B Wilder
(74) *Attorney, Agent, or Firm* — Rodney J. Fuller; Booth Udall Fuller, PLC

(57) ABSTRACT

The present invention relates to method of detecting and characterizing one or more *Borrelia* species causing Lyme Disease or tick-borne relapsing fever within a sample from a subject, the method comprising: a) subjecting DNA and/or RNA from the sample to a PCR amplification reaction using primer pairs targeting at least one region of *Borrelia* 16S rRNA and at least one region of flaB, ospA, ospB, ospC, glpQ, 16S-23S intergenic spacer (IGS1), 5S-23S intergenic spacer (IGS2), bbk32, dbpA, dbpB, and/or p66; and b) analyzing amplification products resulting from the PCR amplification reaction to detect the one or more *Borrelia* species.

14 Claims, 7 Drawing Sheets
Specification includes a Sequence Listing.

FIG. 6

*Borrelia* 16S assays

Alignment of 185 unique rDNA sequences from >20 *Borrelia spp.*

- 5 assays cover majority of gene sequence
- 5 amplicons increase accuracy and specificity

SEQUENCE LISTING

<160> NUMBER OF SEQ ID NOS: 477

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
cgggtgagta acgcgtggat                                              20

<210> SEQ ID NO 2
<211> LENGTH: 22
<212> TYPE: DNA
<213> ORGANISM: Artificial Sequence
<220> FEATURE:
<223> OTHER INFORMATION: Primer

<400> SEQUENCE: 2
cctctcaggc cggttactta tc                                           22

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
cggtcacact ggaactgaga                                              20

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
gctgctggca cgtaattagc                                              20

<210> SEQ ID NO 5
<211> LENGTH: 18
<212> TYPE: DNA
<213> ORGANISM: Artificial Sequence
<220> FEATURE:
<223> OTHER INFORMATION: Primer

<400> SEQUENCE: 5
gcgagcgttg ttcgggat                                                18

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
actcagcgtc agtcttgacc                                              20

<210> SEQ ID NO 7
<211> LENGTH: 22
<212> TYPE: DNA
<213> ORGANISM: Artificial Sequence

```
<220> FEATURE:
<223> OTHER INFORMATION: Primer

<400> SEQUENCE: 7
cgctgtaaac gatgcacact tg                                            22

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
acaaccatgc agcacctgta                                               20

<210> SEQ ID NO 9
<211> LENGTH: 18
<212> TYPE: DNA
<213> ORGANISM: Artificial Sequence
<220> FEATURE:
<223> OTHER INFORMATION: Primer

<400> SEQUENCE: 9
gcaacgagcg caaccctt                                                 18

<210> SEQ ID NO 10
<211> LENGTH: 24
<212> TYPE: DNA
<213> ORGANISM: Artificial Sequence
<220> FEATURE:
<223> OTHER INFORMATION: Primer

<400> SEQUENCE: 10
tacaaggccc gagaacgtat tcac                                          24

<210> SEQ ID NO 11
<211> LENGTH: 27
<212> TYPE: DNA
<213> ORGANISM: Artificial Sequence
<220> FEATURE:
<223> OTHER INFORMATION: Primer

<400> SEQUENCE: 11
gagttcgcgg gagagtaggt tattgcc                                       27

<210> SEQ ID NO 12
<211> LENGTH: 26
<212> TYPE: DNA
<213> ORGANISM: Artificial Sequence
<220> FEATURE:
<223> OTHER INFORMATION: Primer

<400> SEQUENCE: 12
tcagggtact tagatgkttc acttcc                                        26

<210> SEQ ID NO 13
<211> LENGTH: 18
<212> TYPE: DNA
<213> ORGANISM: Artificial Sequence
<220> FEATURE:
<223> OTHER INFORMATION: Primer

<400> SEQUENCE: 13
ctgcgagttc gcgggaga                                                 18
```

```
<210> SEQ ID NO 14
<211> LENGTH: 18
<212> TYPE: DNA
<213> ORGANISM: Artificial Sequence
<220> FEATURE:
<223> OTHER INFORMATION: Primer

<400> SEQUENCE: 14
tcctaggcat tcaccata                                                    18

<210> SEQ ID NO 15
<211> LENGTH: 21
<212> TYPE: DNA
<213> ORGANISM: Artificial Sequence
<220> FEATURE:
<223> OTHER INFORMATION: Primer

<400> SEQUENCE: 15
cgaccttctt cgccttaaag c                                                21

<210> SEQ ID NO 16
<211> LENGTH: 21
<212> TYPE: DNA
<213> ORGANISM: Artificial Sequence
<220> FEATURE:
<223> OTHER INFORMATION: Primer

<400> SEQUENCE: 16
agctcttatt cgctgatggt a                                                21

<210> SEQ ID NO 17
<211> LENGTH: 21
<212> TYPE: DNA
<213> ORGANISM: Artificial Sequence
<220> FEATURE:
<223> OTHER INFORMATION: Primer

<400> SEQUENCE: 17
gtatgtttag tgaggggggt g                                                21

<210> SEQ ID NO 18
<211> LENGTH: 22
<212> TYPE: DNA
<213> ORGANISM: Artificial Sequence
<220> FEATURE:
<223> OTHER INFORMATION: Primer

<400> SEQUENCE: 18
ggatcatagc tcaggtggtt ag                                               22

<210> SEQ ID NO 19
<211> LENGTH: 22
<212> TYPE: DNA
<213> ORGANISM: Artificial Sequence
<220> FEATURE:
<223> OTHER INFORMATION: Primer

<400> SEQUENCE: 19
aggggggtga agtcgtaaca ag                                               22

<210> SEQ ID NO 20
<211> LENGTH: 22
<212> TYPE: DNA
<213> ORGANISM: Artificial Sequence
<220> FEATURE:
<223> OTHER INFORMATION: Primer
```

<400> SEQUENCE: 20
gtctgataaa cctgaggtcg ga                                    22

<210> SEQ ID NO 21
<211> LENGTH: 22
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (21)..(21)
<223> OTHER INFORMATION: n is i

<400> SEQUENCE: 21
gcwtctgatg atgctgctgg na                                    22

<210> SEQ ID NO 22
<211> LENGTH: 22
<212> TYPE: DNA
<213> ORGANISM: Artificial Sequence
<220> FEATURE:
<223> OTHER INFORMATION: Primer

<400> SEQUENCE: 22
gcattccaag ytcttcagct gt                                    22

<210> SEQ ID NO 23
<211> LENGTH: 22
<212> TYPE: DNA
<213> ORGANISM: Artificial Sequence
<220> FEATURE:
<223> OTHER INFORMATION: Primer

<400> SEQUENCE: 23
gcattccaag ctcttcagcw gt                                    22

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
acaccagcrt crctttcagg                                       20

<210> SEQ ID NO 25
<211> LENGTH: 21
<212> TYPE: DNA
<213> ORGANISM: Artificial Sequence
<220> FEATURE:
<223> OTHER INFORMATION: Primer

<400> SEQUENCE: 25
acaccagcat caytakctgg a                                     21

<210> SEQ ID NO 26
<211> LENGTH: 21
<212> TYPE: DNA
<213> ORGANISM: Artificial Sequence
<220> FEATURE:
<223> OTHER INFORMATION: Primer

<400> SEQUENCE: 26
acaccagcat cattrgctgg a        21

<210> SEQ ID NO 27
<211> LENGTH: 25
<212> TYPE: DNA
<213> ORGANISM: Artificial Sequence
<220> FEATURE:
<223> OTHER INFORMATION: Primer

<400> SEQUENCE: 27
ttggaaagca cctaaatttg cyctt        25

<210> SEQ ID NO 28
<211> LENGTH: 25
<212> TYPE: DNA
<213> ORGANISM: Artificial Sequence
<220> FEATURE:
<223> OTHER INFORMATION: Primer

<400> SEQUENCE: 28
ttgraaagca ccaagatttg ctctt        25

<210> SEQ ID NO 29
<211> LENGTH: 25
<212> TYPE: DNA
<213> ORGANISM: Artificial Sequence
<220> FEATURE:
<223> OTHER INFORMATION: Primer

<400> SEQUENCE: 29
ttggaaagca ccyaaatttg ctctt        25

<210> SEQ ID NO 30
<211> LENGTH: 26
<212> TYPE: DNA
<213> ORGANISM: Artificial Sequence
<220> FEATURE:
<223> OTHER INFORMATION: Primer

<400> SEQUENCE: 30
ccagaacata ccttagaakc taaagc        26

<210> SEQ ID NO 31
<211> LENGTH: 25
<212> TYPE: DNA
<213> ORGANISM: Artificial Sequence
<220> FEATURE:
<223> OTHER INFORMATION: Primer

<400> SEQUENCE: 31
cagaacatac attagaagcc aaagc        25

<210> SEQ ID NO 32
<211> LENGTH: 25
<212> TYPE: DNA
<213> ORGANISM: Artificial Sequence
<220> FEATURE:
<223> OTHER INFORMATION: Primer

<400> SEQUENCE: 32
ccttgttgyt tatgccataa kggtt        25

<210> SEQ ID NO 33
<211> LENGTH: 25
<212> TYPE: DNA
<213> ORGANISM: Artificial Sequence

```
<220> FEATURE:
<223> OTHER INFORMATION: Primer

<400> SEQUENCE: 33
ccttgttgtt tatgccahaa gggtt                                              25

<210> SEQ ID NO 34
<211> LENGTH: 26
<212> TYPE: DNA
<213> ORGANISM: Artificial Sequence
<220> FEATURE:
<223> OTHER INFORMATION: Primer

<400> SEQUENCE: 34
ccagaacata ccttagaakc taaagc                                             26

<210> SEQ ID NO 35
<211> LENGTH: 25
<212> TYPE: DNA
<213> ORGANISM: Artificial Sequence
<220> FEATURE:
<223> OTHER INFORMATION: Primer

<400> SEQUENCE: 35
cagaacatac attagaagcc aaagc                                              25

<210> SEQ ID NO 36
<211> LENGTH: 23
<212> TYPE: DNA
<213> ORGANISM: Artificial Sequence
<220> FEATURE:
<223> OTHER INFORMATION: Primer

<400> SEQUENCE: 36
cacattagca gaaatcaaat cac                                                23

<210> SEQ ID NO 37
<211> LENGTH: 27
<212> TYPE: DNA
<213> ORGANISM: Artificial Sequence
<220> FEATURE:
<223> OTHER INFORMATION: Primer

<400> SEQUENCE: 37
gatcaaatct ttcgctaagr cttagtg                                            27

<210> SEQ ID NO 38
<211> LENGTH: 27
<212> TYPE: DNA
<213> ORGANISM: Artificial Sequence
<220> FEATURE:
<223> OTHER INFORMATION: Primer

<400> SEQUENCE: 38
gatcaaatct ttcactgaga cttagtg                                            27

<210> SEQ ID NO 39
<211> LENGTH: 27
<212> TYPE: DNA
<213> ORGANISM: Artificial Sequence
<220> FEATURE:
<223> OTHER INFORMATION: Primer

<400> SEQUENCE: 39
gatcaaatct ttcactaagg cttaatg                                            27
```

<210> SEQ ID NO 40
<211> LENGTH: 18
<212> TYPE: DNA
<213> ORGANISM: Artificial Sequence
<220> FEATURE:
<223> OTHER INFORMATION: Primer

<400> SEQUENCE: 40
gggtatccar ggtccaat                                                       18

<210> SEQ ID NO 41
<211> LENGTH: 24
<212> TYPE: DNA
<213> ORGANISM: Artificial Sequence
<220> FEATURE:
<223> OTHER INFORMATION: Primer

<400> SEQUENCE: 41
tggaggagmc tattgaaagy aatg                                                24

<210> SEQ ID NO 42
<211> LENGTH: 24
<212> TYPE: DNA
<213> ORGANISM: Artificial Sequence
<220> FEATURE:
<223> OTHER INFORMATION: Primer

<400> SEQUENCE: 42
tgaaggakac tattgaaagy aatg                                                24

<210> SEQ ID NO 43
<211> LENGTH: 25
<212> TYPE: DNA
<213> ORGANISM: Artificial Sequence
<220> FEATURE:
<223> OTHER INFORMATION: Primer

<400> SEQUENCE: 43
gcgtgtagaa tacatttggg ttagc                                               25

<210> SEQ ID NO 44
<211> LENGTH: 26
<212> TYPE: DNA
<213> ORGANISM: Artificial Sequence
<220> FEATURE:
<223> OTHER INFORMATION: Primer

<400> SEQUENCE: 44
gacgtgtaga atacatttgg gtttgc                                              26

<210> SEQ ID NO 45
<211> LENGTH: 24
<212> TYPE: DNA
<213> ORGANISM: Artificial Sequence
<220> FEATURE:
<223> OTHER INFORMATION: Primer

<400> SEQUENCE: 45
aacaatgtaa attttgctgc cttt                                                24

<210> SEQ ID NO 46
<211> LENGTH: 20
<212> TYPE: DNA
<213> ORGANISM: Artificial Sequence
<220> FEATURE:
<223> OTHER INFORMATION: Primer

<400> SEQUENCE: 46
cctgagacct caagcatcat                                          20

<210> SEQ ID NO 47
<211> LENGTH: 20
<212> TYPE: DNA
<213> ORGANISM: Artificial Sequence
<220> FEATURE:
<223> OTHER INFORMATION: Primer

<400> SEQUENCE: 47
cggttccaag gtaacaagtg                                          20

<210> SEQ ID NO 48
<211> LENGTH: 26
<212> TYPE: DNA
<213> ORGANISM: Artificial Sequence
<220> FEATURE:
<223> OTHER INFORMATION: Primer

<400> SEQUENCE: 48
taatccaata ctacatgcga ccaata                                   26

<210> SEQ ID NO 49
<211> LENGTH: 24
<212> TYPE: DNA
<213> ORGANISM: Artificial Sequence
<220> FEATURE:
<223> OTHER INFORMATION: Primer

<400> SEQUENCE: 49
agtttgactg gaacacwcct gatc                                     24

<210> SEQ ID NO 50
<211> LENGTH: 24
<212> TYPE: DNA
<213> ORGANISM: Artificial Sequence
<220> FEATURE:
<223> OTHER INFORMATION: Primer

<400> SEQUENCE: 50
ctcgtaacca atctcaagct caac                                     24

<210> SEQ ID NO 51
<211> LENGTH: 24
<212> TYPE: DNA
<213> ORGANISM: Artificial Sequence
<220> FEATURE:
<223> OTHER INFORMATION: Primer

<400> SEQUENCE: 51
gggagagtaa cggagaracw aagg                                     24

<210> SEQ ID NO 52
<211> LENGTH: 23
<212> TYPE: DNA
<213> ORGANISM: Artificial Sequence
<220> FEATURE:
<223> OTHER INFORMATION: Primer

<400> SEQUENCE: 52
ctggcaccac caataccata acc                                      23

<210> SEQ ID NO 53

```
<211> LENGTH: 22
<212> TYPE: DNA
<213> ORGANISM: Artificial Sequence
<220> FEATURE:
<223> OTHER INFORMATION: Primer

<400> SEQUENCE: 53
ctggcaccac caataccrta cc                                          22

<210> SEQ ID NO 54
<211> LENGTH: 24
<212> TYPE: DNA
<213> ORGANISM: Artificial Sequence
<220> FEATURE:
<223> OTHER INFORMATION: Primer

<400> SEQUENCE: 54
gggagagtaa cggagaracw aagg                                        24

<210> SEQ ID NO 55
<211> LENGTH: 24
<212> TYPE: DNA
<213> ORGANISM: Artificial Sequence
<220> FEATURE:
<223> OTHER INFORMATION: Primer

<400> SEQUENCE: 55
ctcgtaacca atctcaagct caac                                        24

<210> SEQ ID NO 56
<211> LENGTH: 29
<212> TYPE: DNA
<213> ORGANISM: Artificial Sequence
<220> FEATURE:
<223> OTHER INFORMATION: Primer

<400> SEQUENCE: 56
gaggatttta tctttgtatt gtagctaac                                   29

<210> SEQ ID NO 57
<211> LENGTH: 23
<212> TYPE: DNA
<213> ORGANISM: Artificial Sequence
<220> FEATURE:
<223> OTHER INFORMATION: Primer

<400> SEQUENCE: 57
tgtaaggtcc agccgaactg act                                         23

<210> SEQ ID NO 58
<211> LENGTH: 30
<212> TYPE: DNA
<213> ORGANISM: Artificial Sequence
<220> FEATURE:
<223> OTHER INFORMATION: Primer

<400> SEQUENCE: 58
tttaataatg ctggtcaagt atggaatcat                                  30

<210> SEQ ID NO 59
<211> LENGTH: 24
<212> TYPE: DNA
<213> ORGANISM: Artificial Sequence
<220> FEATURE:
<223> OTHER INFORMATION: Primer

<400> SEQUENCE: 59
```
aagcrtgytc ccatacatcc atag                                              24

<210> SEQ ID NO 60
<211> LENGTH: 18
<212> TYPE: DNA
<213> ORGANISM: Artificial Sequence
<220> FEATURE:
<223> OTHER INFORMATION: Primer

<400> SEQUENCE: 60
tgcggtgaca gaagactc                                                     18

<210> SEQ ID NO 61
<211> LENGTH: 29
<212> TYPE: DNA
<213> ORGANISM: Artificial Sequence
<220> FEATURE:
<223> OTHER INFORMATION: Primer

<400> SEQUENCE: 61
cagcagaaac tgttaatttt actttactc                                         29

<210> SEQ ID NO 62
<211> LENGTH: 18
<212> TYPE: DNA
<213> ORGANISM: Artificial Sequence
<220> FEATURE:
<223> OTHER INFORMATION: Primer

<400> SEQUENCE: 62
tgcggtgaca gaagactc                                                     18

<210> SEQ ID NO 63
<211> LENGTH: 30
<212> TYPE: DNA
<213> ORGANISM: Artificial Sequence
<220> FEATURE:
<223> OTHER INFORMATION: Primer

<400> SEQUENCE: 63
aatcagcaga aactgttaat tttactttac                                        30

<210> SEQ ID NO 64
<211> LENGTH: 23
<212> TYPE: DNA
<213> ORGANISM: Artificial Sequence
<220> FEATURE:
<223> OTHER INFORMATION: Primer

<400> SEQUENCE: 64 atgaaaaga atacattaag tgc                                                23

<210> SEQ ID NO 65
<211> LENGTH: 31
<212> TYPE: DNA
<213> ORGANISM: Artificial Sequence
<220> FEATURE:
<223> OTHER INFORMATION: Primer

<400> SEQUENCE: 65
attaatctta taatattgat tttaattaag g                                      31

<210> SEQ ID NO 66
<211> LENGTH: 29
<212> TYPE: DNA

<210> SEQ ID NO 66
<211> LENGTH: 29
<212> TYPE: DNA
<213> ORGANISM: Artificial Sequence
<220> FEATURE:
<223> OTHER INFORMATION: Primer

<400> SEQUENCE: 66
tattaatgac tttatttta tttatatct                                 29

<210> SEQ ID NO 67
<211> LENGTH: 25
<212> TYPE: DNA
<213> ORGANISM: Artificial Sequence
<220> FEATURE:
<223> OTHER INFORMATION: Primer

<400> SEQUENCE: 67 ttgatttaa ttaaggtttt tttgg                                     25

<210> SEQ ID NO 68
<211> LENGTH: 24
<212> TYPE: DNA
<213> ORGANISM: Artificial Sequence
<220> FEATURE:
<223> OTHER INFORMATION: Primer

<400> SEQUENCE: 68
aaagaataca ttaagtgcga tatt                                     24

<210> SEQ ID NO 69
<211> LENGTH: 21
<212> TYPE: DNA
<213> ORGANISM: Artificial Sequence
<220> FEATURE:
<223> OTHER INFORMATION: Primer

<400> SEQUENCE: 69
gggcttgtaa gctctttaac t                                        21

<210> SEQ ID NO 70
<211> LENGTH: 23
<212> TYPE: DNA
<213> ORGANISM: Artificial Sequence
<220> FEATURE:
<223> OTHER INFORMATION: Primer

<400> SEQUENCE: 70
gatttttcta tatttggaca cat                                      23

<210> SEQ ID NO 71
<211> LENGTH: 24
<212> TYPE: DNA
<213> ORGANISM: Artificial Sequence
<220> FEATURE:
<223> OTHER INFORMATION: Primer

<400> SEQUENCE: 71
tgtaaatctt attagttttt caag                                     24

<210> SEQ ID NO 72
<211> LENGTH: 24
<212> TYPE: DNA
<213> ORGANISM: Artificial Sequence
<220> FEATURE:
<223> OTHER INFORMATION: Primer

<400> SEQUENCE: 72
caaaaaagaa acaccctcag atcc                                     24

<210> SEQ ID NO 73
<211> LENGTH: 29
<212> TYPE: DNA
<213> ORGANISM: Artificial Sequence
<220> FEATURE:
<223> OTHER INFORMATION: Primer

<400> SEQUENCE: 73
cctgttttta ataaattttt tgtagcatc                                              29

<210> SEQ ID NO 74
<211> LENGTH: 18
<212> TYPE: DNA
<213> ORGANISM: Artificial Sequence
<220> FEATURE:
<223> OTHER INFORMATION: Primer

<400> SEQUENCE: 74
cgaagatact aaatctgt                                                          18

<210> SEQ ID NO 75
<211> LENGTH: 20
<212> TYPE: DNA
<213> ORGANISM: Artificial Sequence
<220> FEATURE:
<223> OTHER INFORMATION: Primer

<400> SEQUENCE: 75
gctgcttttg agatgtgtcc                                                        20

<210> SEQ ID NO 76
<211> LENGTH: 23
<212> TYPE: DNA
<213> ORGANISM: Artificial Sequence
<220> FEATURE:
<223> OTHER INFORMATION: Primer

<400> SEQUENCE: 76
gagcttaaag gaacttctga taa                                                    23

<210> SEQ ID NO 77
<211> LENGTH: 21
<212> TYPE: DNA
<213> ORGANISM: Artificial Sequence
<220> FEATURE:
<223> OTHER INFORMATION: Primer

<400> SEQUENCE: 77
gtattgttgt actgtaattg t                                                      21

<210> SEQ ID NO 78
<211> LENGTH: 21
<212> TYPE: DNA
<213> ORGANISM: Artificial Sequence
<220> FEATURE:
<223> OTHER INFORMATION: Primer

<400> SEQUENCE: 78
accagargaa gccatacaaa c                                                      21

<210> SEQ ID NO 79
<211> LENGTH: 23
<212> TYPE: DNA
<213> ORGANISM: Artificial Sequence
<220> FEATURE:

<223> OTHER INFORMATION: Primer

<400> SEQUENCE: 79
tgacacttca agcaatgttc gta                                          23

<210> SEQ ID NO 80
<211> LENGTH: 18
<212> TYPE: DNA
<213> ORGANISM: Artificial Sequence
<220> FEATURE:
<223> OTHER INFORMATION: Primer

<400> SEQUENCE: 80
aacgccgaac ttggtgtg                                                18

<210> SEQ ID NO 81
<211> LENGTH: 19
<212> TYPE: DNA
<213> ORGANISM: Artificial Sequence
<220> FEATURE:
<223> OTHER INFORMATION: Primer

<400> SEQUENCE: 81
aacaccgaac cagaggaag                                               19

<210> SEQ ID NO 82
<211> LENGTH: 21
<212> TYPE: DNA
<213> ORGANISM: Artificial Sequence
<220> FEATURE:
<223> OTHER INFORMATION: Primer

<400> SEQUENCE: 82
sctgaytgcc artggaatga a                                            21

<210> SEQ ID NO 83
<211> LENGTH: 24
<212> TYPE: DNA
<213> ORGANISM: Artificial Sequence
<220> FEATURE:
<223> OTHER INFORMATION: Primer

<400> SEQUENCE: 83
atgtgctgtt attgctacct actg                                         24

<210> SEQ ID NO 84
<211> LENGTH: 28
<212> TYPE: DNA
<213> ORGANISM: Artificial Sequence
<220> FEATURE:
<223> OTHER INFORMATION: Primer

<400> SEQUENCE: 84
attattacta ctaccattca ctgctaca                                     28

<210> SEQ ID NO 85
<211> LENGTH: 21
<212> TYPE: DNA
<213> ORGANISM: Artificial Sequence
<220> FEATURE:
<223> OTHER INFORMATION: Primer

<400> SEQUENCE: 85
tcaaatccag caaagccatc a                                            21

```
<210> SEQ ID NO 86
<211> LENGTH: 27
<212> TYPE: DNA
<213> ORGANISM: Artificial Sequence
<220> FEATURE:
<223> OTHER INFORMATION: Primer

<400> SEQUENCE: 86
agaatacact agcattacta cctgact                                          27

<210> SEQ ID NO 87
<211> LENGTH: 23
<212> TYPE: DNA
<213> ORGANISM: Artificial Sequence
<220> FEATURE:
<223> OTHER INFORMATION: Primer

<400> SEQUENCE: 87
tagcgttggt attaagtggt tgt                                              23

<210> SEQ ID NO 88
<211> LENGTH: 21
<212> TYPE: DNA
<213> ORGANISM: Artificial Sequence
<220> FEATURE:
<223> OTHER INFORMATION: Primer

<400> SEQUENCE: 88
gtcatagcat agttcgggtc a                                                21

<210> SEQ ID NO 89
<211> LENGTH: 23
<212> TYPE: DNA
<213> ORGANISM: Artificial Sequence
<220> FEATURE:
<223> OTHER INFORMATION: Primer

<400> SEQUENCE: 89
aagaccaaty ctgtcacctc tga                                              23

<210> SEQ ID NO 90
<211> LENGTH: 22
<212> TYPE: DNA
<213> ORGANISM: Artificial Sequence
<220> FEATURE:
<223> OTHER INFORMATION: Primer

<400> SEQUENCE: 90
caaagcgtct acgctgcagt cc                                               22

<210> SEQ ID NO 91
<211> LENGTH: 23
<212> TYPE: DNA
<213> ORGANISM: Artificial Sequence
<220> FEATURE:
<223> OTHER INFORMATION: Primer

<400> SEQUENCE: 91
gaaaggagtg cgggtaatag gtt                                              23

<210> SEQ ID NO 92
<211> LENGTH: 22
<212> TYPE: DNA
<213> ORGANISM: Artificial Sequence
<220> FEATURE:
<223> OTHER INFORMATION: Primer
```

<400> SEQUENCE: 92
ggcctgcaag tccaatatat gg                                    22

<210> SEQ ID NO 93
<211> LENGTH: 19
<212> TYPE: DNA
<213> ORGANISM: Artificial Sequence
<220> FEATURE:
<223> OTHER INFORMATION: Primer

<400> SEQUENCE: 93
cattggacgg catcacgat                                        19

<210> SEQ ID NO 94
<211> LENGTH: 18
<212> TYPE: DNA
<213> ORGANISM: Artificial Sequence
<220> FEATURE:
<223> OTHER INFORMATION: Primer

<400> SEQUENCE: 94
agttggccag cgattcga                                         18

<210> SEQ ID NO 95
<211> LENGTH: 29
<212> TYPE: DNA
<213> ORGANISM: Artificial Sequence
<220> FEATURE:
<223> OTHER INFORMATION: Primer

<400> SEQUENCE: 95
ctaagccata agccctttct ctaacttgt                             29

<210> SEQ ID NO 96
<211> LENGTH: 26
<212> TYPE: DNA
<213> ORGANISM: Artificial Sequence
<220> FEATURE:
<223> OTHER INFORMATION: Primer

<400> SEQUENCE: 96
agcaatgaca aagcttgttg aaaaag                                26

<210> SEQ ID NO 97
<211> LENGTH: 25
<212> TYPE: DNA
<213> ORGANISM: Artificial Sequence
<220> FEATURE:
<223> OTHER INFORMATION: Primer

<400> SEQUENCE: 97
gtaattgcag aaacaccttt tgaat                                 25

<210> SEQ ID NO 98
<211> LENGTH: 21
<212> TYPE: DNA
<213> ORGANISM: Artificial Sequence
<220> FEATURE:
<223> OTHER INFORMATION: Primer

<400> SEQUENCE: 98
ctgcttttga gatgtgtcca a                                     21

<210> SEQ ID NO 99
<211> LENGTH: 24

```
<212> TYPE: DNA
<213> ORGANISM: Artificial Sequence
<220> FEATURE:
<223> OTHER INFORMATION: Primer

<400> SEQUENCE: 99
tgtaattgca gaaacacctt ttga                                          24

<210> SEQ ID NO 100
<211> LENGTH: 20
<212> TYPE: DNA
<213> ORGANISM: Artificial Sequence
<220> FEATURE:
<223> OTHER INFORMATION: Primer

<400> SEQUENCE: 100
gctgcttttg agatgtgtcc                                               20

<210> SEQ ID NO 101
<211> LENGTH: 27
<212> TYPE: DNA
<213> ORGANISM: Artificial Sequence
<220> FEATURE:
<223> OTHER INFORMATION: Primer

<400> SEQUENCE: 101
atcawmtgag gcaaataaag ttgtaga                                       27

<210> SEQ ID NO 102
<211> LENGTH: 21
<212> TYPE: DNA
<213> ORGANISM: Artificial Sequence
<220> FEATURE:
<223> OTHER INFORMATION: Primer

<400> SEQUENCE: 102
tgttctgcyg ctttagtaag g                                             21

<210> SEQ ID NO 103
<211> LENGTH: 25
<212> TYPE: DNA
<213> ORGANISM: Artificial Sequence
<220> FEATURE:
<223> OTHER INFORMATION: Primer

<400> SEQUENCE: 103
ttracttctt ctatygcatc catta                                         25

<210> SEQ ID NO 104
<211> LENGTH: 25
<212> TYPE: DNA
<213> ORGANISM: Artificial Sequence
<220> FEATURE:
<223> OTHER INFORMATION: Primer

<400> SEQUENCE: 104
trttccttct catccaattc tatgt                                         25

<210> SEQ ID NO 105
<211> LENGTH: 26
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (9)..(9)
```

<223> OTHER INFORMATION: n is i

<400> SEQUENCE: 105
ggctaaatna gtagttgcaa aygaca                                         26

<210> SEQ ID NO 106
<211> LENGTH: 17
<212> TYPE: DNA
<213> ORGANISM: Artificial Sequence
<220> FEATURE:
<223> OTHER INFORMATION: Primer

<400> SEQUENCE: 106
gcttctgttg ccaggtg                                                    17

<210> SEQ ID NO 107
<211> LENGTH: 21
<212> TYPE: DNA
<213> ORGANISM: Artificial Sequence
<220> FEATURE:
<223> OTHER INFORMATION: Primer

<400> SEQUENCE: 107
accgtccaaa gctgataggt c                                               21

<210> SEQ ID NO 108
<211> LENGTH: 22
<212> TYPE: DNA
<213> ORGANISM: Artificial Sequence
<220> FEATURE:
<223> OTHER INFORMATION: Primer

<400> SEQUENCE: 108
cgaaactgcg aatggctcat ta                                              22

<210> SEQ ID NO 109
<211> LENGTH: 24
<212> TYPE: DNA
<213> ORGANISM: Artificial Sequence
<220> FEATURE:
<223> OTHER INFORMATION: Primer

<400> SEQUENCE: 109
cctgccaaat atgatgacat caag                                            24

<210> SEQ ID NO 110
<211> LENGTH: 19
<212> TYPE: DNA
<213> ORGANISM: Artificial Sequence
<220> FEATURE:
<223> OTHER INFORMATION: Primer

<400> SEQUENCE: 110
gtggtcgttg agggcaatg                                                  19

<210> SEQ ID NO 111
<211> LENGTH: 37
<212> TYPE: DNA
<213> ORGANISM: Artificial Sequence
<220> FEATURE:
<223> OTHER INFORMATION: Primer

<400> SEQUENCE: 111
acccaactga atggagccgg gtgagtaacg cgtggat                              37

```
<210> SEQ ID NO 112
<211> LENGTH: 41
<212> TYPE: DNA
<213> ORGANISM: Artificial Sequence
<220> FEATURE:
<223> OTHER INFORMATION: Primer

<400> SEQUENCE: 112
acgcacttga cttgtcttcc ctctcaggcc ggttacttat c        41

<210> SEQ ID NO 113
<211> LENGTH: 37
<212> TYPE: DNA
<213> ORGANISM: Artificial Sequence
<220> FEATURE:
<223> OTHER INFORMATION: Primer

<400> SEQUENCE: 113
acccaactga atggagccgg tcacactgga actgaga            37

<210> SEQ ID NO 114
<211> LENGTH: 39
<212> TYPE: DNA
<213> ORGANISM: Artificial Sequence
<220> FEATURE:
<223> OTHER INFORMATION: Primer

<400> SEQUENCE: 114
acgcacttga cttgtcttcg ctgctggcac gtaattagc          39

<210> SEQ ID NO 115
<211> LENGTH: 35
<212> TYPE: DNA
<213> ORGANISM: Artificial Sequence
<220> FEATURE:
<223> OTHER INFORMATION: Primer

<400> SEQUENCE: 115
acccaactga atggagcgcg agcgttgttc gggat              35

<210> SEQ ID NO 116
<211> LENGTH: 39
<212> TYPE: DNA
<213> ORGANISM: Artificial Sequence
<220> FEATURE:
<223> OTHER INFORMATION: Primer

<400> SEQUENCE: 116
acgcacttga cttgtcttca ctcagcgtca gtcttgacc          39

<210> SEQ ID NO 117
<211> LENGTH: 39
<212> TYPE: DNA
<213> ORGANISM: Artificial Sequence
<220> FEATURE:
<223> OTHER INFORMATION: Primer

<400> SEQUENCE: 117
acccaactga atggagccgc tgtaaacgat gcacacttg          39

<210> SEQ ID NO 118
<211> LENGTH: 39
<212> TYPE: DNA
<213> ORGANISM: Artificial Sequence
<220> FEATURE:
<223> OTHER INFORMATION: Primer
```

<400> SEQUENCE: 118
acgcacttga cttgtcttca caaccatgca gcacctgta                                39

<210> SEQ ID NO 119
<211> LENGTH: 35
<212> TYPE: DNA
<213> ORGANISM: Artificial Sequence
<220> FEATURE:
<223> OTHER INFORMATION: Primer

<400> SEQUENCE: 119
acccaactga atggagcgca acgagcgcaa ccctt                                   35

<210> SEQ ID NO 120
<211> LENGTH: 43
<212> TYPE: DNA
<213> ORGANISM: Artificial Sequence
<220> FEATURE:
<223> OTHER INFORMATION: Primer

<400> SEQUENCE: 120
acgcacttga cttgtcttct acaaggcccg agaacgtatt cac                          43

<210> SEQ ID NO 121
<211> LENGTH: 41
<212> TYPE: DNA
<213> ORGANISM: Artificial Sequence
<220> FEATURE:
<223> OTHER INFORMATION: Primer

<400> SEQUENCE: 121
acccaactga atggagcagt ttgactggaa cacwcctgat c                            41

<210> SEQ ID NO 122
<211> LENGTH: 43
<212> TYPE: DNA
<213> ORGANISM: Artificial Sequence
<220> FEATURE:
<223> OTHER INFORMATION: Primer

<400> SEQUENCE: 122
acgcacttga cttgtcttcc tcgtaaccaa tctcaagctc aac                          43

<210> SEQ ID NO 123
<211> LENGTH: 41
<212> TYPE: DNA
<213> ORGANISM: Artificial Sequence
<220> FEATURE:
<223> OTHER INFORMATION: Primer

<400> SEQUENCE: 123
acccaactga atggagcggg agagtaacgg agaracwaag g                            41

<210> SEQ ID NO 124
<211> LENGTH: 42
<212> TYPE: DNA
<213> ORGANISM: Artificial Sequence
<220> FEATURE:
<223> OTHER INFORMATION: Primer

<400> SEQUENCE: 124
acgcacttga cttgtcttcc tggcaccacc aataccataa cc                           42

<210> SEQ ID NO 125
<211> LENGTH: 41

```
<212> TYPE: DNA
<213> ORGANISM: Artificial Sequence
<220> FEATURE:
<223> OTHER INFORMATION: Primer

<400> SEQUENCE: 125
acgcacttga cttgtcttcc tggcaccacc aataccrtac c                          41

<210> SEQ ID NO 126
<211> LENGTH: 38
<212> TYPE: DNA
<213> ORGANISM: Artificial Sequence
<220> FEATURE:
<223> OTHER INFORMATION: Primer

<400> SEQUENCE: 126
acccaactga atggagcacc gtccaaagct gataggtc                              38

<210> SEQ ID NO 127
<211> LENGTH: 41
<212> TYPE: DNA
<213> ORGANISM: Artificial Sequence
<220> FEATURE:
<223> OTHER INFORMATION: Primer

<400> SEQUENCE: 127
acgcacttga cttgtcttcc gaaactgcga atggctcatt a                          41

<210> SEQ ID NO 128
<211> LENGTH: 43
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (26)..(26)
<223> OTHER INFORMATION: n is i

<400> SEQUENCE: 128
acccaactga atggagcggc taaatnagta gttgcaaayg aca                        43

<210> SEQ ID NO 129
<211> LENGTH: 36
<212> TYPE: DNA
<213> ORGANISM: Artificial Sequence
<220> FEATURE:
<223> OTHER INFORMATION: Primer

<400> SEQUENCE: 129
acgcacttga cttgtcttcg cttctgttgc caggtg                               36

<210> SEQ ID NO 130
<211> LENGTH: 41
<212> TYPE: DNA
<213> ORGANISM: Artificial Sequence
<220> FEATURE:
<223> OTHER INFORMATION: Primer

<400> SEQUENCE: 130
acccaactga atggagctgg aggagmctat tgaaagyaat g                          41

<210> SEQ ID NO 131
<211> LENGTH: 41
<212> TYPE: DNA
<213> ORGANISM: Artificial Sequence
<220> FEATURE:
```

<223> OTHER INFORMATION: Primer

<400> SEQUENCE: 131
acccaactga atggagctga aggakactat tgaaagyaat g         41

<210> SEQ ID NO 132
<211> LENGTH: 44
<212> TYPE: DNA
<213> ORGANISM: Artificial Sequence
<220> FEATURE:
<223> OTHER INFORMATION: Primer

<400> SEQUENCE: 132
acgcacttga cttgtcttcg cgtgtagaat acatttgggt tagc       44

<210> SEQ ID NO 133
<211> LENGTH: 45
<212> TYPE: DNA
<213> ORGANISM: Artificial Sequence
<220> FEATURE:
<223> OTHER INFORMATION: Primer

<400> SEQUENCE: 133
acgcacttga cttgtcttcg acgtgtagaa tacatttggg tttgc      45

<210> SEQ ID NO 134
<211> LENGTH: 41
<212> TYPE: DNA
<213> ORGANISM: Artificial Sequence
<220> FEATURE:
<223> OTHER INFORMATION: Primer

<400> SEQUENCE: 134
acccaactga atggagcaac aatgtaaatt ttgctgcctt t          41

<210> SEQ ID NO 135
<211> LENGTH: 39
<212> TYPE: DNA
<213> ORGANISM: Artificial Sequence
<220> FEATURE:
<223> OTHER INFORMATION: Primer

<400> SEQUENCE: 135
acgcacttga cttgtcttcc ctgagacctc aagcatcat            39

<210> SEQ ID NO 136
<211> LENGTH: 37
<212> TYPE: DNA
<213> ORGANISM: Artificial Sequence
<220> FEATURE:
<223> OTHER INFORMATION: Primer

<400> SEQUENCE: 136
acccaactga atggagccgg ttccaaggta acaagtg              37

<210> SEQ ID NO 137
<211> LENGTH: 45
<212> TYPE: DNA
<213> ORGANISM: Artificial Sequence
<220> FEATURE:
<223> OTHER INFORMATION: Primer

<400> SEQUENCE: 137
acgcacttga cttgtcttct aatccaatac tacatgcgac caata     45

```
<210> SEQ ID NO 138
<211> LENGTH: 46
<212> TYPE: DNA
<213> ORGANISM: Artificial Sequence
<220> FEATURE:
<223> OTHER INFORMATION: Primer

<400> SEQUENCE: 138
acccaactga atggagcgag gattttatct ttgtattgta gctaac          46

<210> SEQ ID NO 139
<211> LENGTH: 42
<212> TYPE: DNA
<213> ORGANISM: Artificial Sequence
<220> FEATURE:
<223> OTHER INFORMATION: Primer

<400> SEQUENCE: 139
acgcacttga cttgtcttct gtaaggtcca gccgaactga ct              42

<210> SEQ ID NO 140
<211> LENGTH: 47
<212> TYPE: DNA
<213> ORGANISM: Artificial Sequence
<220> FEATURE:
<223> OTHER INFORMATION: Primer

<400> SEQUENCE: 140
acccaactga atggagcttt aataatgctg gtcaagtatg gaatcat         47

<210> SEQ ID NO 141
<211> LENGTH: 43
<212> TYPE: DNA
<213> ORGANISM: Artificial Sequence
<220> FEATURE:
<223> OTHER INFORMATION: Primer

<400> SEQUENCE: 141
acgcacttga cttgtcttca agcrtgytcc catacatcca tag             43

<210> SEQ ID NO 142
<211> LENGTH: 38
<212> TYPE: DNA
<213> ORGANISM: Artificial Sequence
<220> FEATURE:
<223> OTHER INFORMATION: Primer

<400> SEQUENCE: 142
acccaactga atggagcacc agargaagcc atacaaac                   38

<210> SEQ ID NO 143
<211> LENGTH: 40
<212> TYPE: DNA
<213> ORGANISM: Artificial Sequence
<220> FEATURE:
<223> OTHER INFORMATION: Primer

<400> SEQUENCE: 143
acccaactga atggagctga cacttcaagc aatgttcgta                 40

<210> SEQ ID NO 144
<211> LENGTH: 35
<212> TYPE: DNA
<213> ORGANISM: Artificial Sequence
<220> FEATURE:
<223> OTHER INFORMATION: Primer
```

<400> SEQUENCE: 144
acccaactga atggagcaac gccgaacttg gtgtg    35

<210> SEQ ID NO 145
<211> LENGTH: 36
<212> TYPE: DNA
<213> ORGANISM: Artificial Sequence
<220> FEATURE:
<223> OTHER INFORMATION: Primer

<400> SEQUENCE: 145
acccaactga atggagcaac accgaaccag aggaag    36

<210> SEQ ID NO 146
<211> LENGTH: 40
<212> TYPE: DNA
<213> ORGANISM: Artificial Sequence
<220> FEATURE:
<223> OTHER INFORMATION: Primer

<400> SEQUENCE: 146
acgcacttga cttgtcttcs ctgaytgcca rtggaatgaa    40

<210> SEQ ID NO 147
<211> LENGTH: 43
<212> TYPE: DNA
<213> ORGANISM: Artificial Sequence
<220> FEATURE:
<223> OTHER INFORMATION: Primer

<400> SEQUENCE: 147
acgcacttga cttgtcttca tgtgctgtta ttgctaccta ctg    43

<210> SEQ ID NO 148
<211> LENGTH: 47
<212> TYPE: DNA
<213> ORGANISM: Artificial Sequence
<220> FEATURE:
<223> OTHER INFORMATION: Primer

<400> SEQUENCE: 148
acgcacttga cttgtcttca ttattactac taccattcac tgctaca    47

<210> SEQ ID NO 149
<211> LENGTH: 40
<212> TYPE: DNA
<213> ORGANISM: Artificial Sequence
<220> FEATURE:
<223> OTHER INFORMATION: Primer

<400> SEQUENCE: 149
acgcacttga cttgtcttct caaatccagc aaagccatca    40

<210> SEQ ID NO 150
<211> LENGTH: 46
<212> TYPE: DNA
<213> ORGANISM: Artificial Sequence
<220> FEATURE:
<223> OTHER INFORMATION: Primer

<400> SEQUENCE: 150
acgcacttga cttgtcttca gaatacacta gcattactac ctgact    46

<210> SEQ ID NO 151
<211> LENGTH: 39

```
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (38)..(38)
<223> OTHER INFORMATION: n is i

<400> SEQUENCE: 151
acccaactga atggagcgcw tctgatgatg ctgctggna                         39

<210> SEQ ID NO 152
<211> LENGTH: 41
<212> TYPE: DNA
<213> ORGANISM: Artificial Sequence
<220> FEATURE:
<223> OTHER INFORMATION: Primer

<400> SEQUENCE: 152
acgcacttga cttgtcttcg cattccaagy tcttcagctg t                      41

<210> SEQ ID NO 153
<211> LENGTH: 41
<212> TYPE: DNA
<213> ORGANISM: Artificial Sequence
<220> FEATURE:
<223> OTHER INFORMATION: Primer

<400> SEQUENCE: 153
acgcacttga cttgtcttcg cattccaagc tcttcagcwg t                      41

<210> SEQ ID NO 154
<211> LENGTH: 37
<212> TYPE: DNA
<213> ORGANISM: Artificial Sequence
<220> FEATURE:
<223> OTHER INFORMATION: Primer

<400> SEQUENCE: 154
acccaactga atggagcaca ccagcrtcrc tttcagg                           37

<210> SEQ ID NO 155
<211> LENGTH: 38
<212> TYPE: DNA
<213> ORGANISM: Artificial Sequence
<220> FEATURE:
<223> OTHER INFORMATION: Primer

<400> SEQUENCE: 155
acccaactga atggagcaca ccagcatcay takctgga                          38

<210> SEQ ID NO 156
<211> LENGTH: 38
<212> TYPE: DNA
<213> ORGANISM: Artificial Sequence
<220> FEATURE:
<223> OTHER INFORMATION: Primer

<400> SEQUENCE: 156
acccaactga atggagcaca ccagcatcat trgctgga                          38

<210> SEQ ID NO 157
<211> LENGTH: 44
<212> TYPE: DNA
<213> ORGANISM: Artificial Sequence
<220> FEATURE:
```

<223> OTHER INFORMATION: Primer

<400> SEQUENCE: 157
acgcacttga cttgtcttct tggaaagcac ctaaatttgc yctt           44

<210> SEQ ID NO 158
<211> LENGTH: 44
<212> TYPE: DNA
<213> ORGANISM: Artificial Sequence
<220> FEATURE:
<223> OTHER INFORMATION: Primer

<400> SEQUENCE: 158
acgcacttga cttgtcttct tgraaagcac caagatttgc tctt           44

<210> SEQ ID NO 159
<211> LENGTH: 44
<212> TYPE: DNA
<213> ORGANISM: Artificial Sequence
<220> FEATURE:
<223> OTHER INFORMATION: Primer

<400> SEQUENCE: 159
acgcacttga cttgtcttct tggaaagcac cyaaatttgc tctt           44

<210> SEQ ID NO 160
<211> LENGTH: 46
<212> TYPE: DNA
<213> ORGANISM: Artificial Sequence
<220> FEATURE:
<223> OTHER INFORMATION: Primer

<400> SEQUENCE: 160
acccaactga atggagccta agccataagc cctttctcta acttgt         46

<210> SEQ ID NO 161
<211> LENGTH: 45
<212> TYPE: DNA
<213> ORGANISM: Artificial Sequence
<220> FEATURE:
<223> OTHER INFORMATION: Primer

<400> SEQUENCE: 161
acgcacttga cttgtcttca gcaatgacaa agcttgttga aaaag          45

<210> SEQ ID NO 162
<211> LENGTH: 43
<212> TYPE: DNA
<213> ORGANISM: Artificial Sequence
<220> FEATURE:
<223> OTHER INFORMATION: Primer

<400> SEQUENCE: 162
acccaactga atggagccca gaacatacct tagaakctaa agc            43

<210> SEQ ID NO 163
<211> LENGTH: 42
<212> TYPE: DNA
<213> ORGANISM: Artificial Sequence
<220> FEATURE:
<223> OTHER INFORMATION: Primer

<400> SEQUENCE: 163
acccaactga atggagccag aacatacatt agaagccaaa gc             42

<210> SEQ ID NO 164
<211> LENGTH: 44
<212> TYPE: DNA
<213> ORGANISM: Artificial Sequence
<220> FEATURE:
<223> OTHER INFORMATION: Primer

<400> SEQUENCE: 164
acgcacttga cttgtcttcc cttgttgytt atgccataak ggtt                44

<210> SEQ ID NO 165
<211> LENGTH: 44
<212> TYPE: DNA
<213> ORGANISM: Artificial Sequence
<220> FEATURE:
<223> OTHER INFORMATION: Primer

<400> SEQUENCE: 165
acgcacttga cttgtcttcc cttgttgttt atgccahaag ggtt                44

<210> SEQ ID NO 166
<211> LENGTH: 43
<212> TYPE: DNA
<213> ORGANISM: Artificial Sequence
<220> FEATURE:
<223> OTHER INFORMATION: Primer

<400> SEQUENCE: 166
acccaactga atggagccca gaacatacct tagaakctaa agc                 43

<210> SEQ ID NO 167
<211> LENGTH: 42
<212> TYPE: DNA
<213> ORGANISM: Artificial Sequence
<220> FEATURE:
<223> OTHER INFORMATION: Primer

<400> SEQUENCE: 167
acccaactga atggagccag aacatacatt agaagccaaa gc                  42

<210> SEQ ID NO 168
<211> LENGTH: 42
<212> TYPE: DNA
<213> ORGANISM: Artificial Sequence
<220> FEATURE:
<223> OTHER INFORMATION: Primer

<400> SEQUENCE: 168
acgcacttga cttgtcttcc acattagcag aaatcaaatc ac                  42

<210> SEQ ID NO 169
<211> LENGTH: 46
<212> TYPE: DNA
<213> ORGANISM: Artificial Sequence
<220> FEATURE:
<223> OTHER INFORMATION: Primer

<400> SEQUENCE: 169
acgcacttga cttgtcttcg atcaaatctt tcgctaagrc ttagtg              46

<210> SEQ ID NO 170
<211> LENGTH: 46
<212> TYPE: DNA
<213> ORGANISM: Artificial Sequence
<220> FEATURE:
<223> OTHER INFORMATION: Primer -continued

<400> SEQUENCE: 170
acgcacttga cttgtcttcg atcaaatctt tcactgagac ttagtg        46

<210> SEQ ID NO 171
<211> LENGTH: 46
<212> TYPE: DNA
<213> ORGANISM: Artificial Sequence
<220> FEATURE:
<223> OTHER INFORMATION: Primer

<400> SEQUENCE: 171
acgcacttga cttgtcttcg atcaaatctt tcactaaggc ttaatg        46

<210> SEQ ID NO 172
<211> LENGTH: 37
<212> TYPE: DNA
<213> ORGANISM: Artificial Sequence
<220> FEATURE:
<223> OTHER INFORMATION: Primer

<400> SEQUENCE: 172
acgcacttga cttgtcttcg ggtatccarg gtccaat        37

<210> SEQ ID NO 173
<211> LENGTH: 40
<212> TYPE: DNA
<213> ORGANISM: Artificial Sequence
<220> FEATURE:
<223> OTHER INFORMATION: Primer

<400> SEQUENCE: 173
acccaactga atggagcaag accaatyctg tcacctctga        40

<210> SEQ ID NO 174
<211> LENGTH: 41
<212> TYPE: DNA
<213> ORGANISM: Artificial Sequence
<220> FEATURE:
<223> OTHER INFORMATION: Primer

<400> SEQUENCE: 174
acgcacttga cttgtcttcc aaagcgtcta cgctgcagtc c        41

<210> SEQ ID NO 175
<211> LENGTH: 38
<212> TYPE: DNA
<213> ORGANISM: Artificial Sequence
<220> FEATURE:
<223> OTHER INFORMATION: Primer

<400> SEQUENCE: 175
acccaactga atggagcgta tgtttagtga gggggggtg        38

<210> SEQ ID NO 176
<211> LENGTH: 41
<212> TYPE: DNA
<213> ORGANISM: Artificial Sequence
<220> FEATURE:
<223> OTHER INFORMATION: Primer

<400> SEQUENCE: 176
acgcacttga cttgtcttcg gatcatagct caggtggtta g        41

<210> SEQ ID NO 177
<211> LENGTH: 39

```
<212> TYPE: DNA
<213> ORGANISM: Artificial Sequence
<220> FEATURE:
<223> OTHER INFORMATION: Primer

<400> SEQUENCE: 177
acccaactga atggagcagg ggggtgaagt cgtaacaag                           39

<210> SEQ ID NO 178
<211> LENGTH: 41
<212> TYPE: DNA
<213> ORGANISM: Artificial Sequence
<220> FEATURE:
<223> OTHER INFORMATION: Primer

<400> SEQUENCE: 178
acgcacttga cttgtcttcg tctgataaac ctgaggtcgg a                        41

<210> SEQ ID NO 179
<211> LENGTH: 38
<212> TYPE: DNA
<213> ORGANISM: Artificial Sequence
<220> FEATURE:
<223> OTHER INFORMATION: Primer

<400> SEQUENCE: 179
acccaactga atggagccga ccttcttcgc cttaaagc                            38

<210> SEQ ID NO 180
<211> LENGTH: 40
<212> TYPE: DNA
<213> ORGANISM: Artificial Sequence
<220> FEATURE:
<223> OTHER INFORMATION: Primer

<400> SEQUENCE: 180
acgcacttga cttgtcttca gctcttattc gctgatggta                          40

<210> SEQ ID NO 181
<211> LENGTH: 35
<212> TYPE: DNA
<213> ORGANISM: Artificial Sequence
<220> FEATURE:
<223> OTHER INFORMATION: Primer

<400> SEQUENCE: 181
acccaactga atggagcctg cgagttcgcg ggaga                               35

<210> SEQ ID NO 182
<211> LENGTH: 37
<212> TYPE: DNA
<213> ORGANISM: Artificial Sequence
<220> FEATURE:
<223> OTHER INFORMATION: Primer

<400> SEQUENCE: 182
acgcacttga cttgtcttct cctaggcatt caccata                             37

<210> SEQ ID NO 183
<211> LENGTH: 44
<212> TYPE: DNA
<213> ORGANISM: Artificial Sequence
<220> FEATURE:
<223> OTHER INFORMATION: Primer

<400> SEQUENCE: 183
```

-continued acccaactga atggagcgag ttcgcgggag agtaggttat tgcc      44

<210> SEQ ID NO 184
<211> LENGTH: 45
<212> TYPE: DNA
<213> ORGANISM: Artificial Sequence
<220> FEATURE:
<223> OTHER INFORMATION: Primer

<400> SEQUENCE: 184
acgcacttga cttgtcttct cagggtactt agatgkttca cttcc      45

<210> SEQ ID NO 185
<211> LENGTH: 41
<212> TYPE: DNA
<213> ORGANISM: Artificial Sequence
<220> FEATURE:
<223> OTHER INFORMATION: Primer

<400> SEQUENCE: 185
acccaactga atggagccct gccaaatatg atgacatcaa g      41

<210> SEQ ID NO 186
<211> LENGTH: 38
<212> TYPE: DNA
<213> ORGANISM: Artificial Sequence
<220> FEATURE:
<223> OTHER INFORMATION: Primer

<400> SEQUENCE: 186
acgcacttga cttgtcttcg tggtcgttga gggcaatg      38

<210> SEQ ID NO 187
<211> LENGTH: 40
<212> TYPE: DNA
<213> ORGANISM: Artificial Sequence
<220> FEATURE:
<223> OTHER INFORMATION: Primer

<400> SEQUENCE: 187
acccaactga atggagcgag cttaaaggaa cttctgataa      40

<210> SEQ ID NO 188
<211> LENGTH: 40
<212> TYPE: DNA
<213> ORGANISM: Artificial Sequence
<220> FEATURE:
<223> OTHER INFORMATION: Primer

<400> SEQUENCE: 188
acgcacttga cttgtcttcg tattgttgta ctgtaattgt      40

<210> SEQ ID NO 189
<211> LENGTH: 35
<212> TYPE: DNA
<213> ORGANISM: Artificial Sequence
<220> FEATURE:
<223> OTHER INFORMATION: Primer

<400> SEQUENCE: 189
acccaactga atggagctgc ggtgacagaa gactc      35

<210> SEQ ID NO 190
<211> LENGTH: 48
<212> TYPE: DNA
<213> ORGANISM: Artificial Sequence
<220> FEATURE:
<223> OTHER INFORMATION: Primer

<400> SEQUENCE: 190
acgcacttga cttgtcttcc agcagaaact gttaatttta ctttactc          48

<210> SEQ ID NO 191
<211> LENGTH: 35
<212> TYPE: DNA
<213> ORGANISM: Artificial Sequence
<220> FEATURE:
<223> OTHER INFORMATION: Primer

<400> SEQUENCE: 191
acccaactga atggagctgc ggtgacagaa gactc                        35

<210> SEQ ID NO 192
<211> LENGTH: 49
<212> TYPE: DNA
<213> ORGANISM: Artificial Sequence
<220> FEATURE:
<223> OTHER INFORMATION: Primer

<400> SEQUENCE: 192
acgcacttga cttgtcttca atcagcagaa actgttaatt ttactttac         49

<210> SEQ ID NO 193
<211> LENGTH: 40
<212> TYPE: DNA
<213> ORGANISM: Artificial Sequence
<220> FEATURE:
<223> OTHER INFORMATION: Primer

<400> SEQUENCE: 193
acccaactga atggagcatg aaaaagaata cattaagtgc                   40

<210> SEQ ID NO 194
<211> LENGTH: 50
<212> TYPE: DNA
<213> ORGANISM: Artificial Sequence
<220> FEATURE:
<223> OTHER INFORMATION: Primer

<400> SEQUENCE: 194
acgcacttga cttgtcttca ttaatcttat aatattgatt ttaattaagg        50

<210> SEQ ID NO 195
<211> LENGTH: 46
<212> TYPE: DNA
<213> ORGANISM: Artificial Sequence
<220> FEATURE:
<223> OTHER INFORMATION: Primer

<400> SEQUENCE: 195
acccaactga atggagctat taatgacttt atttttattt atatct            46

<210> SEQ ID NO 196
<211> LENGTH: 44
<212> TYPE: DNA
<213> ORGANISM: Artificial Sequence
<220> FEATURE:
<223> OTHER INFORMATION: Primer

<400> SEQUENCE: 196
acgcacttga cttgtcttct tgattttaat taaggttttt ttgg              44

```
<210> SEQ ID NO 197
<211> LENGTH: 41
<212> TYPE: DNA
<213> ORGANISM: Artificial Sequence
<220> FEATURE:
<223> OTHER INFORMATION: Primer

<400> SEQUENCE: 197
acccaactga atggagcaaa gaatacatta agtgcgatat t          41

<210> SEQ ID NO 198
<211> LENGTH: 40
<212> TYPE: DNA
<213> ORGANISM: Artificial Sequence
<220> FEATURE:
<223> OTHER INFORMATION: Primer

<400> SEQUENCE: 198
acgcacttga cttgtcttcg ggcttgtaag ctctttaact            40

<210> SEQ ID NO 199
<211> LENGTH: 40
<212> TYPE: DNA
<213> ORGANISM: Artificial Sequence
<220> FEATURE:
<223> OTHER INFORMATION: Primer

<400> SEQUENCE: 199
acccaactga atggagcgag cttaaaggaa cttctgataa            40

<210> SEQ ID NO 200
<211> LENGTH: 40
<212> TYPE: DNA
<213> ORGANISM: Artificial Sequence
<220> FEATURE:
<223> OTHER INFORMATION: Primer

<400> SEQUENCE: 200
acgcacttga cttgtcttcg tattgttgta ctgtaattgt            40

<210> SEQ ID NO 201
<211> LENGTH: 40
<212> TYPE: DNA
<213> ORGANISM: Artificial Sequence
<220> FEATURE:
<223> OTHER INFORMATION: Primer

<400> SEQUENCE: 201
acccaactga atggagcgag cttaaaggaa cttctgataa            40

<210> SEQ ID NO 202
<211> LENGTH: 40
<212> TYPE: DNA
<213> ORGANISM: Artificial Sequence
<220> FEATURE:
<223> OTHER INFORMATION: Primer

<400> SEQUENCE: 202
acgcacttga cttgtcttcg tattgttgta ctgtaattgt            40

<210> SEQ ID NO 203
<211> LENGTH: 40
<212> TYPE: DNA
<213> ORGANISM: Artificial Sequence
<220> FEATURE:
<223> OTHER INFORMATION: Primer
```

-continued

<400> SEQUENCE: 203
acccaactga atggagcgag cttaaaggaa cttctgataa       40

<210> SEQ ID NO 204
<211> LENGTH: 40
<212> TYPE: DNA
<213> ORGANISM: Artificial Sequence
<220> FEATURE:
<223> OTHER INFORMATION: Primer

<400> SEQUENCE: 204
acgcacttga cttgtcttcg tattgttgta ctgtaattgt       40

<210> SEQ ID NO 205
<211> LENGTH: 40
<212> TYPE: DNA
<213> ORGANISM: Artificial Sequence
<220> FEATURE:
<223> OTHER INFORMATION: Primer

<400> SEQUENCE: 205
acccaactga atggagcgat ttttctatat ttggacacat       40

<210> SEQ ID NO 206
<211> LENGTH: 43
<212> TYPE: DNA
<213> ORGANISM: Artificial Sequence
<220> FEATURE:
<223> OTHER INFORMATION: Primer

<400> SEQUENCE: 206
acgcacttga cttgtcttct gtaaatctta ttagtttttc aag       43

<210> SEQ ID NO 207
<211> LENGTH: 41
<212> TYPE: DNA
<213> ORGANISM: Artificial Sequence
<220> FEATURE:
<223> OTHER INFORMATION: Primer

<400> SEQUENCE: 207
acccaactga atggagccaa aaagaaaca ccctcagatc c       41

<210> SEQ ID NO 208
<211> LENGTH: 48
<212> TYPE: DNA
<213> ORGANISM: Artificial Sequence
<220> FEATURE:
<223> OTHER INFORMATION: Primer

<400> SEQUENCE: 208
acgcacttga cttgtcttcc ctgtttttaa ataaattttt gtagcatc       48

<210> SEQ ID NO 209
<211> LENGTH: 35
<212> TYPE: DNA
<213> ORGANISM: Artificial Sequence
<220> FEATURE:
<223> OTHER INFORMATION: Primer

<400> SEQUENCE: 209
acccaactga atggagccga agatactaaa tctgt       35

<210> SEQ ID NO 210

```
<211> LENGTH: 39
<212> TYPE: DNA
<213> ORGANISM: Artificial Sequence
<220> FEATURE:
<223> OTHER INFORMATION: Primer

<400> SEQUENCE: 210
acgcacttga cttgtcttcg ctgcttttga gatgtgtcc                              39

<210> SEQ ID NO 211
<211> LENGTH: 40
<212> TYPE: DNA
<213> ORGANISM: Artificial Sequence
<220> FEATURE:
<223> OTHER INFORMATION: Primer

<400> SEQUENCE: 211
acccaactga atggagcgag cttaaaggaa cttctgataa                             40

<210> SEQ ID NO 212
<211> LENGTH: 40
<212> TYPE: DNA
<213> ORGANISM: Artificial Sequence
<220> FEATURE:
<223> OTHER INFORMATION: Primer

<400> SEQUENCE: 212
acgcacttga cttgtcttcg tattgttgta ctgtaattgt                             40

<210> SEQ ID NO 213
<211> LENGTH: 36
<212> TYPE: DNA
<213> ORGANISM: Artificial Sequence
<220> FEATURE:
<223> OTHER INFORMATION: Primer

<400> SEQUENCE: 213
acccaactga atggagccat tggacggcat cacgat                                 36

<210> SEQ ID NO 214
<211> LENGTH: 37
<212> TYPE: DNA
<213> ORGANISM: Artificial Sequence
<220> FEATURE:
<223> OTHER INFORMATION: Primer

<400> SEQUENCE: 214
acgcacttga cttgtcttca gttggccagc gattcga                                37

<210> SEQ ID NO 215
<211> LENGTH: 40
<212> TYPE: DNA
<213> ORGANISM: Artificial Sequence
<220> FEATURE:
<223> OTHER INFORMATION: Primer

<400> SEQUENCE: 215
acccaactga atggagcgaa aggagtgcgg gtaataggtt                             40

<210> SEQ ID NO 216
<211> LENGTH: 41
<212> TYPE: DNA
<213> ORGANISM: Artificial Sequence
<220> FEATURE:
<223> OTHER INFORMATION: Primer

<400> SEQUENCE: 216
```

-continued acgcacttga cttgtcttcg gcctgcaagt ccaatatatg g        41

<210> SEQ ID NO 217
<211> LENGTH: 17
<212> TYPE: DNA
<213> ORGANISM: Artificial Sequence
<220> FEATURE:
<223> OTHER INFORMATION: Primer

<400> SEQUENCE: 217
acccaactga atggagc        17

<210> SEQ ID NO 218
<211> LENGTH: 19
<212> TYPE: DNA
<213> ORGANISM: Artificial Sequence
<220> FEATURE:
<223> OTHER INFORMATION: Primer

<400> SEQUENCE: 218
acgcacttga cttgtcttc        19

<210> SEQ ID NO 219
<211> LENGTH: 20
<212> TYPE: DNA
<213> ORGANISM: Artificial Sequence
<220> FEATURE:
<223> OTHER INFORMATION: Primer

<400> SEQUENCE: 219
gggttcgagt ccctyaacct        20

<210> SEQ ID NO 220
<211> LENGTH: 23
<212> TYPE: DNA
<213> ORGANISM: Artificial Sequence
<220> FEATURE:
<223> OTHER INFORMATION: Primer

<400> SEQUENCE: 220
ttggtttaga gcatcggctt tgc        23

<210> SEQ ID NO 221
<211> LENGTH: 22
<212> TYPE: DNA
<213> ORGANISM: Artificial Sequence
<220> FEATURE:
<223> OTHER INFORMATION: Primer

<400> SEQUENCE: 221
ccttgcactt tagcgaaaca ac        22

<210> SEQ ID NO 222
<211> LENGTH: 22
<212> TYPE: DNA
<213> ORGANISM: Artificial Sequence
<220> FEATURE:
<223> OTHER INFORMATION: Primer

<400> SEQUENCE: 222
ccttgtgctt tagtgaaaca ac        22

<210> SEQ ID NO 223
<211> LENGTH: 23
<212> TYPE: DNA

```
<213> ORGANISM: Artificial Sequence
<220> FEATURE:
<223> OTHER INFORMATION: Primer

<400> SEQUENCE: 223
acttgccata cgtaaacaac cgt                                              23

<210> SEQ ID NO 224
<211> LENGTH: 26
<212> TYPE: DNA
<213> ORGANISM: Artificial Sequence
<220> FEATURE:
<223> OTHER INFORMATION: Primer

<400> SEQUENCE: 224
ctcatgactt gtcacacgta aacaac                                           26

<210> SEQ ID NO 225
<211> LENGTH: 22
<212> TYPE: DNA
<213> ORGANISM: Artificial Sequence
<220> FEATURE:
<223> OTHER INFORMATION: Primer

<400> SEQUENCE: 225
gttcaactcc tcctggtccc aa                                               22

<210> SEQ ID NO 226
<211> LENGTH: 25
<212> TYPE: DNA
<213> ORGANISM: Artificial Sequence
<220> FEATURE:
<223> OTHER INFORMATION: Primer

<400> SEQUENCE: 226
atcctataga tgcaatctct tgwcc                                            25

<210> SEQ ID NO 227
<211> LENGTH: 27
<212> TYPE: DNA
<213> ORGANISM: Artificial Sequence
<220> FEATURE:
<223> OTHER INFORMATION: Primer

<400> SEQUENCE: 227
tttgcatgta atcaagtctt ggaattc                                          27

<210> SEQ ID NO 228
<211> LENGTH: 25
<212> TYPE: DNA
<213> ORGANISM: Artificial Sequence
<220> FEATURE:
<223> OTHER INFORMATION: Primer

<400> SEQUENCE: 228
tactttcacc tctagacatt cttgt                                            25

<210> SEQ ID NO 229
<211> LENGTH: 25
<212> TYPE: DNA
<213> ORGANISM: Artificial Sequence
<220> FEATURE:
<223> OTHER INFORMATION: Primer

<400> SEQUENCE: 229
taggttgatt catgatcagg tcctt                                            25
```

```
<210> SEQ ID NO 230
<211> LENGTH: 21
<212> TYPE: DNA
<213> ORGANISM: Artificial Sequence
<220> FEATURE:
<223> OTHER INFORMATION: Primer

<400> SEQUENCE: 230
cgattcggtc acggctctta c                                            21

<210> SEQ ID NO 231
<211> LENGTH: 28
<212> TYPE: DNA
<213> ORGANISM: Artificial Sequence
<220> FEATURE:
<223> OTHER INFORMATION: Primer

<400> SEQUENCE: 231
ccttatgatt tagtaacaca acgtaagt                                     28

<210> SEQ ID NO 232
<211> LENGTH: 25
<212> TYPE: DNA
<213> ORGANISM: Artificial Sequence
<220> FEATURE:
<223> OTHER INFORMATION: Primer

<400> SEQUENCE: 232
aagctagtaa tgaatgtggg atgtt                                        25

<210> SEQ ID NO 233
<211> LENGTH: 18
<212> TYPE: DNA
<213> ORGANISM: Artificial Sequence
<220> FEATURE:
<223> OTHER INFORMATION: Primer

<400> SEQUENCE: 233
cagccgcatc tgtaactg                                                18

<210> SEQ ID NO 234
<211> LENGTH: 19
<212> TYPE: DNA
<213> ORGANISM: Artificial Sequence
<220> FEATURE:
<223> OTHER INFORMATION: Primer

<400> SEQUENCE: 234
tcagttccca ttgaaactg                                               19

<210> SEQ ID NO 235
<211> LENGTH: 18
<212> TYPE: DNA
<213> ORGANISM: Artificial Sequence
<220> FEATURE:
<223> OTHER INFORMATION: Primer

<400> SEQUENCE: 235
ttyagcygca tctgagac                                                18

<210> SEQ ID NO 236
<211> LENGTH: 18
<212> TYPE: DNA
<213> ORGANISM: Artificial Sequence
<220> FEATURE:
```

<223> OTHER INFORMATION: Primer

<400> SEQUENCE: 236
ttcagctgcc wttgagac                                              18

<210> SEQ ID NO 237
<211> LENGTH: 19
<212> TYPE: DNA
<213> ORGANISM: Artificial Sequence
<220> FEATURE:
<223> OTHER INFORMATION: Primer

<400> SEQUENCE: 237
caggyagcaa ggtatcaga                                             19

<210> SEQ ID NO 238
<211> LENGTH: 19
<212> TYPE: DNA
<213> ORGANISM: Artificial Sequence
<220> FEATURE:
<223> OTHER INFORMATION: Primer

<400> SEQUENCE: 238
crggtagygg ggtatcaga                                             19

<210> SEQ ID NO 239
<211> LENGTH: 19
<212> TYPE: DNA
<213> ORGANISM: Artificial Sequence
<220> FEATURE:
<223> OTHER INFORMATION: Primer

<400> SEQUENCE: 239
aacaggtrga aaggyagca                                             19

<210> SEQ ID NO 240
<211> LENGTH: 23
<212> TYPE: DNA
<213> ORGANISM: Artificial Sequence
<220> FEATURE:
<223> OTHER INFORMATION: Primer

<400> SEQUENCE: 240
cgcaagcaat ctttcagytg tgt                                        23

<210> SEQ ID NO 241
<211> LENGTH: 23
<212> TYPE: DNA
<213> ORGANISM: Artificial Sequence
<220> FEATURE:
<223> OTHER INFORMATION: Primer

<400> SEQUENCE: 241
ctcaaccaat ctttcagcyg tgt                                        23

<210> SEQ ID NO 242
<211> LENGTH: 24
<212> TYPE: DNA
<213> ORGANISM: Artificial Sequence
<220> FEATURE:
<223> OTHER INFORMATION: Primer

<400> SEQUENCE: 242
cttcaagcaa tctttcacat gtgt                                       24

<210> SEQ ID NO 243
<211> LENGTH: 25
<212> TYPE: DNA
<213> ORGANISM: Artificial Sequence
<220> FEATURE:
<223> OTHER INFORMATION: Primer

<400> SEQUENCE: 243
cctcaattaa tctttcagat gtgct                                    25

<210> SEQ ID NO 244
<211> LENGTH: 23
<212> TYPE: DNA
<213> ORGANISM: Artificial Sequence
<220> FEATURE:
<223> OTHER INFORMATION: Primer

<400> SEQUENCE: 244
ttcaagcaat ctttcggctg tgt                                      23

<210> SEQ ID NO 245
<211> LENGTH: 23
<212> TYPE: DNA
<213> ORGANISM: Artificial Sequence
<220> FEATURE:
<223> OTHER INFORMATION: Primer

<400> SEQUENCE: 245
ctccattact ctttcggctg tgt                                      23

<210> SEQ ID NO 246
<211> LENGTH: 25
<212> TYPE: DNA
<213> ORGANISM: Artificial Sequence
<220> FEATURE:
<223> OTHER INFORMATION: Primer

<400> SEQUENCE: 246
ryagckcttg aatcrtcyty taagg                                    25

<210> SEQ ID NO 247
<211> LENGTH: 25
<212> TYPE: DNA
<213> ORGANISM: Artificial Sequence
<220> FEATURE:
<223> OTHER INFORMATION: Primer

<400> SEQUENCE: 247
aagcaatgct tgaatcstmt tctga                                    25

<210> SEQ ID NO 248
<211> LENGTH: 23
<212> TYPE: DNA
<213> ORGANISM: Artificial Sequence
<220> FEATURE:
<223> OTHER INFORMATION: Primer

<400> SEQUENCE: 248
aagcaaagct tgaatcgtct tcc                                      23

<210> SEQ ID NO 249
<211> LENGTH: 24
<212> TYPE: DNA
<213> ORGANISM: Artificial Sequence
<220> FEATURE:
<223> OTHER INFORMATION: Primer

<400> SEQUENCE: 249
gtygaactta aaggaacttc cgat                                          24

<210> SEQ ID NO 250
<211> LENGTH: 24
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(1)
<223> OTHER INFORMATION: n is a, c, g, or t

<400> SEQUENCE: 250
nttgagctwa aaggaacwtc tgat                                          24

<210> SEQ ID NO 251
<211> LENGTH: 23
<212> TYPE: DNA
<213> ORGANISM: Artificial Sequence
<220> FEATURE:
<223> OTHER INFORMATION: Primer

<400> SEQUENCE: 251
gttgagctta aaggrgttkc tga                                           23

<210> SEQ ID NO 252
<211> LENGTH: 23
<212> TYPE: DNA
<213> ORGANISM: Artificial Sequence
<220> FEATURE:
<223> OTHER INFORMATION: Primer

<400> SEQUENCE: 252
ggtgagctta aagggattt tga                                            23

<210> SEQ ID NO 253
<211> LENGTH: 24
<212> TYPE: DNA
<213> ORGANISM: Artificial Sequence
<220> FEATURE:
<223> OTHER INFORMATION: Primer

<400> SEQUENCE: 253
gttgagctta aaggcctttc tgag                                          24

<210> SEQ ID NO 254
<211> LENGTH: 21
<212> TYPE: DNA
<213> ORGANISM: Artificial Sequence
<220> FEATURE:
<223> OTHER INFORMATION: Primer

<400> SEQUENCE: 254
ccgmctmcaa gacttccttc a                                             21

<210> SEQ ID NO 255
<211> LENGTH: 21
<212> TYPE: DNA
<213> ORGANISM: Artificial Sequence
<220> FEATURE:
<223> OTHER INFORMATION: Primer

<400> SEQUENCE: 255
ccgcctacaa gatttcctgg a                                             21

<210> SEQ ID NO 256
<211> LENGTH: 24
<212> TYPE: DNA
<213> ORGANISM: Artificial Sequence
<220> FEATURE:
<223> OTHER INFORMATION: Primer

<400> SEQUENCE: 256
ccaccaacaa gacttccttc tagt                                              24

<210> SEQ ID NO 257
<211> LENGTH: 24
<212> TYPE: DNA
<213> ORGANISM: Artificial Sequence
<220> FEATURE:
<223> OTHER INFORMATION: Primer

<400> SEQUENCE: 257
ccaccaacta gacttccttt aaac                                              24

<210> SEQ ID NO 258
<211> LENGTH: 24
<212> TYPE: DNA
<213> ORGANISM: Artificial Sequence
<220> FEATURE:
<223> OTHER INFORMATION: Primer

<400> SEQUENCE: 258
ccaccaacaa gatttccttc gaac                                              24

<210> SEQ ID NO 259
<211> LENGTH: 24
<212> TYPE: DNA
<213> ORGANISM: Artificial Sequence
<220> FEATURE:
<223> OTHER INFORMATION: Primer

<400> SEQUENCE: 259
cattagctac ttttccttca agag                                              24

<210> SEQ ID NO 260
<211> LENGTH: 24
<212> TYPE: DNA
<213> ORGANISM: Artificial Sequence
<220> FEATURE:
<223> OTHER INFORMATION: Primer

<400> SEQUENCE: 260
cattagctag agttccttca agag                                              24

<210> SEQ ID NO 261
<211> LENGTH: 24
<212> TYPE: DNA
<213> ORGANISM: Artificial Sequence
<220> FEATURE:
<223> OTHER INFORMATION: Primer

<400> SEQUENCE: 261
tcagcagyta gagttccttc aaga                                              24

<210> SEQ ID NO 262
<211> LENGTH: 26
<212> TYPE: DNA
<213> ORGANISM: Artificial Sequence
<220> FEATURE:

```
<223> OTHER INFORMATION: Primer

<400> SEQUENCE: 262
tcaggraaag atgggaatrc atctgc                                              26

<210> SEQ ID NO 263
<211> LENGTH: 27
<212> TYPE: DNA
<213> ORGANISM: Artificial Sequence
<220> FEATURE:
<223> OTHER INFORMATION: Primer

<400> SEQUENCE: 263
grcttgtaag ctctttaact gmattag                                             27

<210> SEQ ID NO 264
<211> LENGTH: 19
<212> TYPE: DNA
<213> ORGANISM: Artificial Sequence
<220> FEATURE:
<223> OTHER INFORMATION: Primer

<400> SEQUENCE: 264
gccyatgacy ggattcaaa                                                      19

<210> SEQ ID NO 265
<211> LENGTH: 21
<212> TYPE: DNA
<213> ORGANISM: Artificial Sequence
<220> FEATURE:
<223> OTHER INFORMATION: Primer

<400> SEQUENCE: 265
ttygcaccta tgactggrtt t                                                   21

<210> SEQ ID NO 266
<211> LENGTH: 20
<212> TYPE: DNA
<213> ORGANISM: Artificial Sequence
<220> FEATURE:
<223> OTHER INFORMATION: Primer

<400> SEQUENCE: 266
ggyttccatg ttgcttgaay                                                     20

<210> SEQ ID NO 267
<211> LENGTH: 21
<212> TYPE: DNA
<213> ORGANISM: Artificial Sequence
<220> FEATURE:
<223> OTHER INFORMATION: Primer

<400> SEQUENCE: 267
tgargctatc catccaagrc c                                                   21

<210> SEQ ID NO 268
<211> LENGTH: 22
<212> TYPE: DNA
<213> ORGANISM: Artificial Sequence
<220> FEATURE:
<223> OTHER INFORMATION: Primer

<400> SEQUENCE: 268
gaagctgtcc atccaagatt ag                                                  22
```

```
<210> SEQ ID NO 269
<211> LENGTH: 24
<212> TYPE: DNA
<213> ORGANISM: Artificial Sequence
<220> FEATURE:
<223> OTHER INFORMATION: Primer

<400> SEQUENCE: 269
cggtttagct tggaatacag atga                                              24

<210> SEQ ID NO 270
<211> LENGTH: 24
<212> TYPE: DNA
<213> ORGANISM: Artificial Sequence
<220> FEATURE:
<223> OTHER INFORMATION: Primer

<400> SEQUENCE: 270
cggttttgcc tggaataaag atga                                              24

<210> SEQ ID NO 271
<211> LENGTH: 23
<212> TYPE: DNA
<213> ORGANISM: Artificial Sequence
<220> FEATURE:
<223> OTHER INFORMATION: Primer

<400> SEQUENCE: 271
ggcytagctt ggaayataga tga                                               23

<210> SEQ ID NO 272
<211> LENGTH: 21
<212> TYPE: DNA
<213> ORGANISM: Artificial Sequence
<220> FEATURE:
<223> OTHER INFORMATION: Primer

<400> SEQUENCE: 272
gcaatmggaa aytcaacatt c                                                 21

<210> SEQ ID NO 273
<211> LENGTH: 23
<212> TYPE: DNA
<213> ORGANISM: Artificial Sequence
<220> FEATURE:
<223> OTHER INFORMATION: Primer

<400> SEQUENCE: 273
crcttgcaaa tgggtctatt cct                                               23

<210> SEQ ID NO 274
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(3)
<223> OTHER INFORMATION: n is i

<400> SEQUENCE: 274
ggntctggaa yacttgaagg                                                   20

<210> SEQ ID NO 275
<211> LENGTH: 20
<212> TYPE: DNA
```

```
<213> ORGANISM: Artificial Sequence
<220> FEATURE:
<223> OTHER INFORMATION: Primer

<400> SEQUENCE: 275
ggatctggrr trcttgaagg                                              20

<210> SEQ ID NO 276
<211> LENGTH: 20
<212> TYPE: DNA
<213> ORGANISM: Artificial Sequence
<220> FEATURE:
<223> OTHER INFORMATION: Primer

<400> SEQUENCE: 276
ggttctggaa sccttgargg                                              20

<210> SEQ ID NO 277
<211> LENGTH: 20
<212> TYPE: DNA
<213> ORGANISM: Artificial Sequence
<220> FEATURE:
<223> OTHER INFORMATION: Primer

<400> SEQUENCE: 277
ggryctgggg trcttgaagg                                              20

<210> SEQ ID NO 278
<211> LENGTH: 22
<212> TYPE: DNA
<213> ORGANISM: Artificial Sequence
<220> FEATURE:
<223> OTHER INFORMATION: Primer

<400> SEQUENCE: 278
ggatctgggg gaaagcttga ag                                           22

<210> SEQ ID NO 279
<211> LENGTH: 20
<212> TYPE: DNA
<213> ORGANISM: Artificial Sequence
<220> FEATURE:
<223> OTHER INFORMATION: Primer

<400> SEQUENCE: 279
ggttctggdg trctkgaagg                                              20

<210> SEQ ID NO 280
<211> LENGTH: 20
<212> TYPE: DNA
<213> ORGANISM: Artificial Sequence
<220> FEATURE:
<223> OTHER INFORMATION: Primer

<400> SEQUENCE: 280
ggatctggmw hgcyygaagg                                              20

<210> SEQ ID NO 281
<211> LENGTH: 20
<212> TYPE: DNA
<213> ORGANISM: Artificial Sequence
<220> FEATURE:
<223> OTHER INFORMATION: Primer

<400> SEQUENCE: 281
ggmgctggam awcttgaagg                                              20
```

<210> SEQ ID NO 282
<211> LENGTH: 24
<212> TYPE: DNA
<213> ORGANISM: Artificial Sequence
<220> FEATURE:
<223> OTHER INFORMATION: Primer

<400> SEQUENCE: 282
caagtytgkt kccrttkct cttg                                               24

<210> SEQ ID NO 283
<211> LENGTH: 24
<212> TYPE: DNA
<213> ORGANISM: Artificial Sequence
<220> FEATURE:
<223> OTHER INFORMATION: Primer

<400> SEQUENCE: 283
caagyytggt wccgtytgct cttr                                              24

<210> SEQ ID NO 284
<211> LENGTH: 24
<212> TYPE: DNA
<213> ORGANISM: Artificial Sequence
<220> FEATURE:
<223> OTHER INFORMATION: Primer

<400> SEQUENCE: 284
cmagtgtagt yccgyttgdt cttg                                              24

<210> SEQ ID NO 285
<211> LENGTH: 24
<212> TYPE: DNA
<213> ORGANISM: Artificial Sequence
<220> FEATURE:
<223> OTHER INFORMATION: Primer

<400> SEQUENCE: 285
caagtmtkgw wccrtttgct cttr                                              24

<210> SEQ ID NO 286
<211> LENGTH: 24
<212> TYPE: DNA
<213> ORGANISM: Artificial Sequence
<220> FEATURE:
<223> OTHER INFORMATION: Primer

<400> SEQUENCE: 286
caagkgtagt ttcgtttkct cttg                                              24

<210> SEQ ID NO 287
<211> LENGTH: 24
<212> TYPE: DNA
<213> ORGANISM: Artificial Sequence
<220> FEATURE:
<223> OTHER INFORMATION: Primer

<400> SEQUENCE: 287
caaktgtagt atyrtttgat cttg                                              24

<210> SEQ ID NO 288
<211> LENGTH: 24
<212> TYPE: DNA
<213> ORGANISM: Artificial Sequence
<220> FEATURE:

```
<223> OTHER INFORMATION: Primer

<400> SEQUENCE: 288
caagmktrgt kccgtttgct cttg                                               24

<210> SEQ ID NO 289
<211> LENGTH: 24
<212> TYPE: DNA
<213> ORGANISM: Artificial Sequence
<220> FEATURE:
<223> OTHER INFORMATION: Primer

<400> SEQUENCE: 289
caagtctggt tccgtctttt cttg                                               24

<210> SEQ ID NO 290
<211> LENGTH: 24
<212> TYPE: DNA
<213> ORGANISM: Artificial Sequence
<220> FEATURE:
<223> OTHER INFORMATION: Primer

<400> SEQUENCE: 290
caagtggtgt tccgtttgtt cttg                                               24

<210> SEQ ID NO 291
<211> LENGTH: 24
<212> TYPE: DNA
<213> ORGANISM: Artificial Sequence
<220> FEATURE:
<223> OTHER INFORMATION: Primer

<400> SEQUENCE: 291
caagtctatt tccatttgct cttg                                               24

<210> SEQ ID NO 292
<211> LENGTH: 24
<212> TYPE: DNA
<213> ORGANISM: Artificial Sequence
<220> FEATURE:
<223> OTHER INFORMATION: Primer

<400> SEQUENCE: 292
caagtctggt tccgttayct ctta                                               24

<210> SEQ ID NO 293
<211> LENGTH: 24
<212> TYPE: DNA
<213> ORGANISM: Artificial Sequence
<220> FEATURE:
<223> OTHER INFORMATION: Primer

<400> SEQUENCE: 293
caagtctggt tccatttgcc ctta                                               24

<210> SEQ ID NO 294
<211> LENGTH: 22
<212> TYPE: DNA
<213> ORGANISM: Artificial Sequence
<220> FEATURE:
<223> OTHER INFORMATION: Primer

<400> SEQUENCE: 294
ggcatttact tacrgtgstg at                                                 22
```

```
<210> SEQ ID NO 295
<211> LENGTH: 22
<212> TYPE: DNA
<213> ORGANISM: Artificial Sequence
<220> FEATURE:
<223> OTHER INFORMATION: Primer

<400> SEQUENCE: 295
ccatgatttg cagcaayagc at                                                22

<210> SEQ ID NO 296
<211> LENGTH: 22
<212> TYPE: DNA
<213> ORGANISM: Artificial Sequence
<220> FEATURE:
<223> OTHER INFORMATION: Primer

<400> SEQUENCE: 296
cgytagctgg gcttagrtat tc                                                22

<210> SEQ ID NO 297
<211> LENGTH: 23
<212> TYPE: DNA
<213> ORGANISM: Artificial Sequence
<220> FEATURE:
<223> OTHER INFORMATION: Primer

<400> SEQUENCE: 297
cgccgraact ttattcttga atg                                               23

<210> SEQ ID NO 298
<211> LENGTH: 24
<212> TYPE: DNA
<213> ORGANISM: Artificial Sequence
<220> FEATURE:
<223> OTHER INFORMATION: Primer

<400> SEQUENCE: 298
acttayggtg gtgattatay tatc                                              24

<210> SEQ ID NO 299
<211> LENGTH: 22
<212> TYPE: DNA
<213> ORGANISM: Artificial Sequence
<220> FEATURE:
<223> OTHER INFORMATION: Primer

<400> SEQUENCE: 299
tgcagcaaca gcattaktac yg                                                22

<210> SEQ ID NO 300
<211> LENGTH: 21
<212> TYPE: DNA
<213> ORGANISM: Artificial Sequence
<220> FEATURE:
<223> OTHER INFORMATION: Primer

<400> SEQUENCE: 300
gctgraggag tagctaatgg t                                                 21

<210> SEQ ID NO 301
<211> LENGTH: 21
<212> TYPE: DNA
<213> ORGANISM: Artificial Sequence
<220> FEATURE:
<223> OTHER INFORMATION: Primer
```

<400> SEQUENCE: 301
gcagcaggag tagctgatga t                              21

<210> SEQ ID NO 302
<211> LENGTH: 21
<212> TYPE: DNA
<213> ORGANISM: Artificial Sequence
<220> FEATURE:
<223> OTHER INFORMATION: Primer

<400> SEQUENCE: 302
mcgcagcagt accggttaaa g                              21

<210> SEQ ID NO 303
<211> LENGTH: 22
<212> TYPE: DNA
<213> ORGANISM: Artificial Sequence
<220> FEATURE:
<223> OTHER INFORMATION: Primer

<400> SEQUENCE: 303
caaccgcagc rwtaatgcta ac                             22

<210> SEQ ID NO 304
<211> LENGTH: 22
<212> TYPE: DNA
<213> ORGANISM: Artificial Sequence
<220> FEATURE:
<223> OTHER INFORMATION: Primer

<400> SEQUENCE: 304
cctcccgtat ctaccactga ac                             22

<210> SEQ ID NO 305
<211> LENGTH: 20
<212> TYPE: DNA
<213> ORGANISM: Artificial Sequence
<220> FEATURE:
<223> OTHER INFORMATION: Primer

<400> SEQUENCE: 305
tgcaggagca gataatggta                                20

<210> SEQ ID NO 306
<211> LENGTH: 20
<212> TYPE: DNA
<213> ORGANISM: Artificial Sequence
<220> FEATURE:
<223> OTHER INFORMATION: Primer

<400> SEQUENCE: 306
gccggcagta atagtaacag                                20

<210> SEQ ID NO 307
<211> LENGTH: 23
<212> TYPE: DNA
<213> ORGANISM: Artificial Sequence
<220> FEATURE:
<223> OTHER INFORMATION: Primer

<400> SEQUENCE: 307
ggtgcaagcc aagtaacata tac                            23

<210> SEQ ID NO 308
<211> LENGTH: 25

```
<212> TYPE: DNA
<213> ORGANISM: Artificial Sequence
<220> FEATURE:
<223> OTHER INFORMATION: Primer

<400> SEQUENCE: 308
aggtacaaat caagtaacat atacc                                          25

<210> SEQ ID NO 309
<211> LENGTH: 19
<212> TYPE: DNA
<213> ORGANISM: Artificial Sequence
<220> FEATURE:
<223> OTHER INFORMATION: Primer

<400> SEQUENCE: 309
aaaccgcctt ccgtttctg                                                 19

<210> SEQ ID NO 310
<211> LENGTH: 19
<212> TYPE: DNA
<213> ORGANISM: Artificial Sequence
<220> FEATURE:
<223> OTHER INFORMATION: Primer

<400> SEQUENCE: 310
aatccacctg ccgcttctg                                                 19

<210> SEQ ID NO 311
<211> LENGTH: 22
<212> TYPE: DNA
<213> ORGANISM: Artificial Sequence
<220> FEATURE:
<223> OTHER INFORMATION: Primer

<400> SEQUENCE: 311
ggcdgtaggy catgtttatg ac                                             22

<210> SEQ ID NO 312
<211> LENGTH: 22
<212> TYPE: DNA
<213> ORGANISM: Artificial Sequence
<220> FEATURE:
<223> OTHER INFORMATION: Primer

<400> SEQUENCE: 312
agctgtgggc cacgtctatg ac                                             22

<210> SEQ ID NO 313
<211> LENGTH: 20
<212> TYPE: DNA
<213> ORGANISM: Artificial Sequence
<220> FEATURE:
<223> OTHER INFORMATION: Primer

<400> SEQUENCE: 313
ccgaaggcag gtgatctttg                                                20

<210> SEQ ID NO 314
<211> LENGTH: 20
<212> TYPE: DNA
<213> ORGANISM: Artificial Sequence
<220> FEATURE:
<223> OTHER INFORMATION: Primer

<400> SEQUENCE: 314
```

```
cagaaggcag gtggtccttg                                                 20

<210> SEQ ID NO 315
<211> LENGTH: 37
<212> TYPE: DNA
<213> ORGANISM: Artificial Sequence
<220> FEATURE:
<223> OTHER INFORMATION: Primer

<400> SEQUENCE: 315
acccaactga atggagccgg gtgagtaacg cgtggat                              37

<210> SEQ ID NO 316
<211> LENGTH: 41
<212> TYPE: DNA
<213> ORGANISM: Artificial Sequence
<220> FEATURE:
<223> OTHER INFORMATION: Primer

<400> SEQUENCE: 316
acgcacttga cttgtcttcc ctctcaggcc ggttacttat c                         41

<210> SEQ ID NO 317
<211> LENGTH: 37
<212> TYPE: DNA
<213> ORGANISM: Artificial Sequence
<220> FEATURE:
<223> OTHER INFORMATION: Primer

<400> SEQUENCE: 317
acccaactga atggagccgg tcacactgga actgaga                              37

<210> SEQ ID NO 318
<211> LENGTH: 39
<212> TYPE: DNA
<213> ORGANISM: Artificial Sequence
<220> FEATURE:
<223> OTHER INFORMATION: Primer

<400> SEQUENCE: 318
acgcacttga cttgtcttcg ctgctggcac gtaattagc                            39

<210> SEQ ID NO 319
<211> LENGTH: 35
<212> TYPE: DNA
<213> ORGANISM: Artificial Sequence
<220> FEATURE:
<223> OTHER INFORMATION: Primer

<400> SEQUENCE: 319
acccaactga atggagcgcg agcgttgttc gggat                                35

<210> SEQ ID NO 320
<211> LENGTH: 39
<212> TYPE: DNA
<213> ORGANISM: Artificial Sequence
<220> FEATURE:
<223> OTHER INFORMATION: Primer

<400> SEQUENCE: 320
acgcacttga cttgtcttca ctcagcgtca gtcttgacc                            39

<210> SEQ ID NO 321
<211> LENGTH: 39
<212> TYPE: DNA
<213> ORGANISM: Artificial Sequence
```

```
<220> FEATURE:
<223> OTHER INFORMATION: Primer

<400> SEQUENCE: 321
acccaactga atggagccgc tgtaaacgat gcacacttg                    39

<210> SEQ ID NO 322
<211> LENGTH: 39
<212> TYPE: DNA
<213> ORGANISM: Artificial Sequence
<220> FEATURE:
<223> OTHER INFORMATION: Primer

<400> SEQUENCE: 322
acgcacttga cttgtcttca caaccatgca gcacctgta                    39

<210> SEQ ID NO 323
<211> LENGTH: 35
<212> TYPE: DNA
<213> ORGANISM: Artificial Sequence
<220> FEATURE:
<223> OTHER INFORMATION: Primer

<400> SEQUENCE: 323
acccaactga atggagcgca acgagcgcaa ccctt                        35

<210> SEQ ID NO 324
<211> LENGTH: 43
<212> TYPE: DNA
<213> ORGANISM: Artificial Sequence
<220> FEATURE:
<223> OTHER INFORMATION: Primer

<400> SEQUENCE: 324
acgcacttga cttgtcttct acaaggcccg agaacgtatt cac               43

<210> SEQ ID NO 325
<211> LENGTH: 35
<212> TYPE: DNA
<213> ORGANISM: Artificial Sequence
<220> FEATURE:
<223> OTHER INFORMATION: Primer

<400> SEQUENCE: 325
acccaactga atggagcctg cgagttcgcg ggaga                        35

<210> SEQ ID NO 326
<211> LENGTH: 37
<212> TYPE: DNA
<213> ORGANISM: Artificial Sequence
<220> FEATURE:
<223> OTHER INFORMATION: Primer

<400> SEQUENCE: 326
acgcacttga cttgtcttct cctaggcatt caccata                      37

<210> SEQ ID NO 327
<211> LENGTH: 37
<212> TYPE: DNA
<213> ORGANISM: Artificial Sequence
<220> FEATURE:
<223> OTHER INFORMATION: Primer

<400> SEQUENCE: 327
acccaactga atggagcggg ttcgagtccc tyaacct                      37
```

<210> SEQ ID NO 328
<211> LENGTH: 40
<212> TYPE: DNA
<213> ORGANISM: Artificial Sequence
<220> FEATURE:
<223> OTHER INFORMATION: Primer

<400> SEQUENCE: 328
acccaactga atggagcttg gtttagagca tcggctttgc                     40

<210> SEQ ID NO 329
<211> LENGTH: 41
<212> TYPE: DNA
<213> ORGANISM: Artificial Sequence
<220> FEATURE:
<223> OTHER INFORMATION: Primer

<400> SEQUENCE: 329
acgcacttga cttgtcttcc cttgcacttt agcgaaacaa c                    41

<210> SEQ ID NO 330
<211> LENGTH: 41
<212> TYPE: DNA
<213> ORGANISM: Artificial Sequence
<220> FEATURE:
<223> OTHER INFORMATION: Primer

<400> SEQUENCE: 330
acgcacttga cttgtcttcc cttgtgcttt agtgaaacaa c                    41

<210> SEQ ID NO 331
<211> LENGTH: 42
<212> TYPE: DNA
<213> ORGANISM: Artificial Sequence
<220> FEATURE:
<223> OTHER INFORMATION: Primer

<400> SEQUENCE: 331
acgcacttga cttgtcttca cttgccatac gtaaacaacc gt                   42

<210> SEQ ID NO 332
<211> LENGTH: 45
<212> TYPE: DNA
<213> ORGANISM: Artificial Sequence
<220> FEATURE:
<223> OTHER INFORMATION: Primer

<400> SEQUENCE: 332
acgcacttga cttgtcttcc tcatgacttg tcacacgtaa acaac                45

<210> SEQ ID NO 333
<211> LENGTH: 41
<212> TYPE: DNA
<213> ORGANISM: Artificial Sequence
<220> FEATURE:
<223> OTHER INFORMATION: Primer

<400> SEQUENCE: 333
acgcacttga cttgtcttcg ttcaactcct cctggtccca a                    41

<210> SEQ ID NO 334
<211> LENGTH: 44
<212> TYPE: DNA
<213> ORGANISM: Artificial Sequence
<220> FEATURE:
<223> OTHER INFORMATION: Primer

<400> SEQUENCE: 334
acgcacttga cttgtcttca tcctatagat gcaatctctt gwcc                44

<210> SEQ ID NO 335
<211> LENGTH: 46
<212> TYPE: DNA
<213> ORGANISM: Artificial Sequence
<220> FEATURE:
<223> OTHER INFORMATION: Primer

<400> SEQUENCE: 335
acgcacttga cttgtcttct ttgcatgtaa tcaagtcttg gaattc              46

<210> SEQ ID NO 336
<211> LENGTH: 44
<212> TYPE: DNA
<213> ORGANISM: Artificial Sequence
<220> FEATURE:
<223> OTHER INFORMATION: Primer

<400> SEQUENCE: 336
acgcacttga cttgtcttct actttcacct ctagacattc ttgt                44

<210> SEQ ID NO 337
<211> LENGTH: 44
<212> TYPE: DNA
<213> ORGANISM: Artificial Sequence
<220> FEATURE:
<223> OTHER INFORMATION: Primer

<400> SEQUENCE: 337
acgcacttga cttgtcttct aggttgattc atgatcaggt cctt                44

<210> SEQ ID NO 338
<211> LENGTH: 40
<212> TYPE: DNA
<213> ORGANISM: Artificial Sequence
<220> FEATURE:
<223> OTHER INFORMATION: Primer

<400> SEQUENCE: 338
acgcacttga cttgtcttcc gattcggtca cggctcttac                     40

<210> SEQ ID NO 339
<211> LENGTH: 47
<212> TYPE: DNA
<213> ORGANISM: Artificial Sequence
<220> FEATURE:
<223> OTHER INFORMATION: Primer

<400> SEQUENCE: 339
acgcacttga cttgtcttcc cttatgattt agtaacacaa cgtaagt             47

<210> SEQ ID NO 340
<211> LENGTH: 44
<212> TYPE: DNA
<213> ORGANISM: Artificial Sequence
<220> FEATURE:
<223> OTHER INFORMATION: Primer

<400> SEQUENCE: 340
acgcacttga cttgtcttca agctagtaat gaatgtggga tgtt                44

<210> SEQ ID NO 341

```
<211> LENGTH: 39
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (38)..(38)
<223> OTHER INFORMATION: n is i

<400> SEQUENCE: 341
acccaactga atggagcgcw tctgatgatg ctgctggna                    39

<210> SEQ ID NO 342
<211> LENGTH: 41
<212> TYPE: DNA
<213> ORGANISM: Artificial Sequence
<220> FEATURE:
<223> OTHER INFORMATION: Primer

<400> SEQUENCE: 342
acgcacttga cttgtcttcg cattccaagy tcttcagctg t                 41

<210> SEQ ID NO 343
<211> LENGTH: 41
<212> TYPE: DNA
<213> ORGANISM: Artificial Sequence
<220> FEATURE:
<223> OTHER INFORMATION: Primer

<400> SEQUENCE: 343
acgcacttga cttgtcttcg cattccaagc tcttcagcwg t                 41

<210> SEQ ID NO 344
<211> LENGTH: 37
<212> TYPE: DNA
<213> ORGANISM: Artificial Sequence
<220> FEATURE:
<223> OTHER INFORMATION: Primer

<400> SEQUENCE: 344
acccaactga atggagcaca ccagcrtcrc tttcagg                      37

<210> SEQ ID NO 345
<211> LENGTH: 38
<212> TYPE: DNA
<213> ORGANISM: Artificial Sequence
<220> FEATURE:
<223> OTHER INFORMATION: Primer

<400> SEQUENCE: 345
acccaactga atggagcaca ccagcatcay takctgga                     38

<210> SEQ ID NO 346
<211> LENGTH: 38
<212> TYPE: DNA
<213> ORGANISM: Artificial Sequence
<220> FEATURE:
<223> OTHER INFORMATION: Primer

<400> SEQUENCE: 346
acccaactga atggagcaca ccagcatcat trgctgga                     38

<210> SEQ ID NO 347
<211> LENGTH: 44
<212> TYPE: DNA
<213> ORGANISM: Artificial Sequence
```

```
<220> FEATURE:
<223> OTHER INFORMATION: Primer

<400> SEQUENCE: 347
acgcacttga cttgtcttct tggaaagcac ctaaatttgc yctt         44

<210> SEQ ID NO 348
<211> LENGTH: 44
<212> TYPE: DNA
<213> ORGANISM: Artificial Sequence
<220> FEATURE:
<223> OTHER INFORMATION: Primer

<400> SEQUENCE: 348
acgcacttga cttgtcttct tgraaagcac caagatttgc tctt         44

<210> SEQ ID NO 349
<211> LENGTH: 44
<212> TYPE: DNA
<213> ORGANISM: Artificial Sequence
<220> FEATURE:
<223> OTHER INFORMATION: Primer

<400> SEQUENCE: 349
acgcacttga cttgtcttct tggaaagcac cyaaatttgc tctt         44

<210> SEQ ID NO 350
<211> LENGTH: 43
<212> TYPE: DNA
<213> ORGANISM: Artificial Sequence
<220> FEATURE:
<223> OTHER INFORMATION: Primer

<400> SEQUENCE: 350
acccaactga atggagccca gaacatacct tagaakctaa agc          43

<210> SEQ ID NO 351
<211> LENGTH: 42
<212> TYPE: DNA
<213> ORGANISM: Artificial Sequence
<220> FEATURE:
<223> OTHER INFORMATION: Primer

<400> SEQUENCE: 351
acccaactga atggagccag aacatacatt agaagccaaa gc           42

<210> SEQ ID NO 352
<211> LENGTH: 44
<212> TYPE: DNA
<213> ORGANISM: Artificial Sequence
<220> FEATURE:
<223> OTHER INFORMATION: Primer

<400> SEQUENCE: 352
acgcacttga cttgtcttcc cttgttgytt atgccataak ggtt         44

<210> SEQ ID NO 353
<211> LENGTH: 44
<212> TYPE: DNA
<213> ORGANISM: Artificial Sequence
<220> FEATURE:
<223> OTHER INFORMATION: Primer

<400> SEQUENCE: 353
acgcacttga cttgtcttcc cttgttgttt atgccahaag ggtt         44
```

<210> SEQ ID NO 354
<211> LENGTH: 41
<212> TYPE: DNA
<213> ORGANISM: Artificial Sequence
<220> FEATURE:
<223> OTHER INFORMATION: Primer

<400> SEQUENCE: 354
acccaactga atggagctgg aggagmctat tgaaagyaat g    41

<210> SEQ ID NO 355
<211> LENGTH: 41
<212> TYPE: DNA
<213> ORGANISM: Artificial Sequence
<220> FEATURE:
<223> OTHER INFORMATION: Primer

<400> SEQUENCE: 355
acccaactga atggagctga aggakactat tgaaagyaat g    41

<210> SEQ ID NO 356
<211> LENGTH: 44
<212> TYPE: DNA
<213> ORGANISM: Artificial Sequence
<220> FEATURE:
<223> OTHER INFORMATION: Primer

<400> SEQUENCE: 356
acgcacttga cttgtcttcg cgtgtagaat acatttgggt tagc    44

<210> SEQ ID NO 357
<211> LENGTH: 45
<212> TYPE: DNA
<213> ORGANISM: Artificial Sequence
<220> FEATURE:
<223> OTHER INFORMATION: Primer

<400> SEQUENCE: 357
acgcacttga cttgtcttcg acgtgtagaa tacatttggg tttgc    45

<210> SEQ ID NO 358
<211> LENGTH: 35
<212> TYPE: DNA
<213> ORGANISM: Artificial Sequence
<220> FEATURE:
<223> OTHER INFORMATION: Primer

<400> SEQUENCE: 358
acccaactga atggagccag ccgcatctgt aactg    35

<210> SEQ ID NO 359
<211> LENGTH: 36
<212> TYPE: DNA
<213> ORGANISM: Artificial Sequence
<220> FEATURE:
<223> OTHER INFORMATION: Primer

<400> SEQUENCE: 359
acccaactga atggagctca gttcccattg aaactg    36

<210> SEQ ID NO 360
<211> LENGTH: 35
<212> TYPE: DNA
<213> ORGANISM: Artificial Sequence
<220> FEATURE:
<223> OTHER INFORMATION: Primer

<400> SEQUENCE: 360
acccaactga atggagctty agcygcatct gagac					35

<210> SEQ ID NO 361
<211> LENGTH: 35
<212> TYPE: DNA
<213> ORGANISM: Artificial Sequence
<220> FEATURE:
<223> OTHER INFORMATION: Primer

<400> SEQUENCE: 361
acccaactga atggagcttc agctgccwtt gagac					35

<210> SEQ ID NO 362
<211> LENGTH: 38
<212> TYPE: DNA
<213> ORGANISM: Artificial Sequence
<220> FEATURE:
<223> OTHER INFORMATION: Primer

<400> SEQUENCE: 362
acgcacttga cttgtcttcc aggyagcaag gtatcaga				38

<210> SEQ ID NO 363
<211> LENGTH: 38
<212> TYPE: DNA
<213> ORGANISM: Artificial Sequence
<220> FEATURE:
<223> OTHER INFORMATION: Primer

<400> SEQUENCE: 363
acgcacttga cttgtcttcc rggtagyggg gtatcaga				38

<210> SEQ ID NO 364
<211> LENGTH: 38
<212> TYPE: DNA
<213> ORGANISM: Artificial Sequence
<220> FEATURE:
<223> OTHER INFORMATION: Primer

<400> SEQUENCE: 364
acgcacttga cttgtcttca acaggtrgaa aggyagca				38

<210> SEQ ID NO 365
<211> LENGTH: 40
<212> TYPE: DNA
<213> ORGANISM: Artificial Sequence
<220> FEATURE:
<223> OTHER INFORMATION: Primer

<400> SEQUENCE: 365
acccaactga atggagccgc aagcaatctt tcagytgtgt				40

<210> SEQ ID NO 366
<211> LENGTH: 40
<212> TYPE: DNA
<213> ORGANISM: Artificial Sequence
<220> FEATURE:
<223> OTHER INFORMATION: Primer

<400> SEQUENCE: 366
acccaactga atggagcctc aaccaatctt tcagcygtgt				40

<210> SEQ ID NO 367

```
<211> LENGTH: 41
<212> TYPE: DNA
<213> ORGANISM: Artificial Sequence
<220> FEATURE:
<223> OTHER INFORMATION: Primer

<400> SEQUENCE: 367
acccaactga atggagcctt caagcaatct ttcacatgtg t               41

<210> SEQ ID NO 368
<211> LENGTH: 42
<212> TYPE: DNA
<213> ORGANISM: Artificial Sequence
<220> FEATURE:
<223> OTHER INFORMATION: Primer

<400> SEQUENCE: 368
acccaactga atggagccct caattaatct ttcagatgtg ct              42

<210> SEQ ID NO 369
<211> LENGTH: 40
<212> TYPE: DNA
<213> ORGANISM: Artificial Sequence
<220> FEATURE:
<223> OTHER INFORMATION: Primer

<400> SEQUENCE: 369
acccaactga atggagcttc aagcaatctt tcggctgtgt                 40

<210> SEQ ID NO 370
<211> LENGTH: 40
<212> TYPE: DNA
<213> ORGANISM: Artificial Sequence
<220> FEATURE:
<223> OTHER INFORMATION: Primer

<400> SEQUENCE: 370
acccaactga atggagcctc cattactctt tcggctgtgt                 40

<210> SEQ ID NO 371
<211> LENGTH: 44
<212> TYPE: DNA
<213> ORGANISM: Artificial Sequence
<220> FEATURE:
<223> OTHER INFORMATION: Primer

<400> SEQUENCE: 371
acgcacttga cttgtcttcr yagckcttga atcrtcytyt aagg            44

<210> SEQ ID NO 372
<211> LENGTH: 44
<212> TYPE: DNA
<213> ORGANISM: Artificial Sequence
<220> FEATURE:
<223> OTHER INFORMATION: Primer

<400> SEQUENCE: 372
acgcacttga cttgtcttca agcaatgctt gaatcstmtt ctga            44

<210> SEQ ID NO 373
<211> LENGTH: 42
<212> TYPE: DNA
<213> ORGANISM: Artificial Sequence
<220> FEATURE:
<223> OTHER INFORMATION: Primer

<400> SEQUENCE: 373
```
acgcacttga cttgtcttca agcaaagctt gaatcgtctt cc    42

<210> SEQ ID NO 374
<211> LENGTH: 41
<212> TYPE: DNA
<213> ORGANISM: Artificial Sequence
<220> FEATURE:
<223> OTHER INFORMATION: Primer

<400> SEQUENCE: 374
acccaactga atggagcggg agagtaacgg agaracwaag g    41

<210> SEQ ID NO 375
<211> LENGTH: 42
<212> TYPE: DNA
<213> ORGANISM: Artificial Sequence
<220> FEATURE:
<223> OTHER INFORMATION: Primer

<400> SEQUENCE: 375
acgcacttga cttgtcttcc tggcaccacc aataccataa cc    42

<210> SEQ ID NO 376
<211> LENGTH: 41
<212> TYPE: DNA
<213> ORGANISM: Artificial Sequence
<220> FEATURE:
<223> OTHER INFORMATION: Primer

<400> SEQUENCE: 376
acgcacttga cttgtcttcc tggcaccacc aataccrtac c    41

<210> SEQ ID NO 377
<211> LENGTH: 46
<212> TYPE: DNA
<213> ORGANISM: Artificial Sequence
<220> FEATURE:
<223> OTHER INFORMATION: Primer

<400> SEQUENCE: 377
acccaactga atggagcgag gattttatct ttgtattgta gctaac    46

<210> SEQ ID NO 378
<211> LENGTH: 42
<212> TYPE: DNA
<213> ORGANISM: Artificial Sequence
<220> FEATURE:
<223> OTHER INFORMATION: Primer

<400> SEQUENCE: 378
acgcacttga cttgtcttct gtaaggtcca gccgaactga ct    42

<210> SEQ ID NO 379
<211> LENGTH: 42
<212> TYPE: DNA
<213> ORGANISM: Artificial Sequence
<220> FEATURE:
<223> OTHER INFORMATION: Primer

<400> SEQUENCE: 379
acccaactga atggagccag gattagatac cctggtagtc ca    42

<210> SEQ ID NO 380
<211> LENGTH: 38
<212> TYPE: DNA

```
<213> ORGANISM: Artificial Sequence
<220> FEATURE:
<223> OTHER INFORMATION: Primer

<400> SEQUENCE: 380
acgcacttga cttgtcttca cgacacgagc tgacgaca                                38

<210> SEQ ID NO 381
<211> LENGTH: 47
<212> TYPE: DNA
<213> ORGANISM: Artificial Sequence
<220> FEATURE:
<223> OTHER INFORMATION: Primer

<400> SEQUENCE: 381
acccaactga atggagcttt aataatgctg gtcaagtatg gaatcat                      47

<210> SEQ ID NO 382
<211> LENGTH: 43
<212> TYPE: DNA
<213> ORGANISM: Artificial Sequence
<220> FEATURE:
<223> OTHER INFORMATION: Primer

<400> SEQUENCE: 382
acgcacttga cttgtcttca agcrtgytcc catacatcca tag                          43

<210> SEQ ID NO 383
<211> LENGTH: 41
<212> TYPE: DNA
<213> ORGANISM: Artificial Sequence
<220> FEATURE:
<223> OTHER INFORMATION: Primer

<400> SEQUENCE: 383
acccaactga atggagcgty gaacttaaag gaacttccga t                            41

<210> SEQ ID NO 384
<211> LENGTH: 41
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (18)..(18)
<223> OTHER INFORMATION: n is a, c, g, or t

<400> SEQUENCE: 384
acccaactga atggagcntt gagctwaaag gaacwtctga t                            41

<210> SEQ ID NO 385
<211> LENGTH: 40
<212> TYPE: DNA
<213> ORGANISM: Artificial Sequence
<220> FEATURE:
<223> OTHER INFORMATION: Primer

<400> SEQUENCE: 385
acccaactga atggagcgtt gagcttaaag grgttkctga                              40

<210> SEQ ID NO 386
<211> LENGTH: 40
<212> TYPE: DNA
<213> ORGANISM: Artificial Sequence
<220> FEATURE:
<223> OTHER INFORMATION: Primer
```

-continued

<400> SEQUENCE: 386
acccaactga atggagcggt gagcttaaag gggattttga                                    40

<210> SEQ ID NO 387
<211> LENGTH: 41
<212> TYPE: DNA
<213> ORGANISM: Artificial Sequence
<220> FEATURE:
<223> OTHER INFORMATION: Primer

<400> SEQUENCE: 387
acccaactga atggagcgtt gagcttaaag gcctttctga g                                  41

<210> SEQ ID NO 388
<211> LENGTH: 40
<212> TYPE: DNA
<213> ORGANISM: Artificial Sequence
<220> FEATURE:
<223> OTHER INFORMATION: Primer

<400> SEQUENCE: 388
acgcacttga cttgtcttcc cgmctmcaag acttccttca                                    40

<210> SEQ ID NO 389
<211> LENGTH: 40
<212> TYPE: DNA
<213> ORGANISM: Artificial Sequence
<220> FEATURE:
<223> OTHER INFORMATION: Primer

<400> SEQUENCE: 389
acgcacttga cttgtcttcc cgcctacaag atttcctgga                                    40

<210> SEQ ID NO 390
<211> LENGTH: 43
<212> TYPE: DNA
<213> ORGANISM: Artificial Sequence
<220> FEATURE:
<223> OTHER INFORMATION: Primer

<400> SEQUENCE: 390
acgcacttga cttgtcttcc caccaacaag acttccttct agt                                43

<210> SEQ ID NO 391
<211> LENGTH: 43
<212> TYPE: DNA
<213> ORGANISM: Artificial Sequence
<220> FEATURE:
<223> OTHER INFORMATION: Primer

<400> SEQUENCE: 391
acgcacttga cttgtcttcc caccaactag acttccttta aac                                43

<210> SEQ ID NO 392
<211> LENGTH: 43
<212> TYPE: DNA
<213> ORGANISM: Artificial Sequence
<220> FEATURE:
<223> OTHER INFORMATION: Primer

<400> SEQUENCE: 392
acgcacttga cttgtcttcc caccaacaag atttccttcg aac                                43

<210> SEQ ID NO 393

<211> LENGTH: 43
<212> TYPE: DNA
<213> ORGANISM: Artificial Sequence
<220> FEATURE:
<223> OTHER INFORMATION: Primer

<400> SEQUENCE: 393
acgcacttga cttgtcttcc attagctact tttccttcaa gag           43

<210> SEQ ID NO 394
<211> LENGTH: 43
<212> TYPE: DNA
<213> ORGANISM: Artificial Sequence
<220> FEATURE:
<223> OTHER INFORMATION: Primer

<400> SEQUENCE: 394
acgcacttga cttgtcttcc attagctaga gttccttcaa gag           43

<210> SEQ ID NO 395
<211> LENGTH: 43
<212> TYPE: DNA
<213> ORGANISM: Artificial Sequence
<220> FEATURE:
<223> OTHER INFORMATION: Primer

<400> SEQUENCE: 395
acgcacttga cttgtcttct cagcagytag agttccttca aga           43

<210> SEQ ID NO 396
<211> LENGTH: 43
<212> TYPE: DNA
<213> ORGANISM: Artificial Sequence
<220> FEATURE:
<223> OTHER INFORMATION: Primer

<400> SEQUENCE: 396
acccaactga atggagctca ggraaagatg ggaatrcatc tgc           43

<210> SEQ ID NO 397
<211> LENGTH: 46
<212> TYPE: DNA
<213> ORGANISM: Artificial Sequence
<220> FEATURE:
<223> OTHER INFORMATION: Primer

<400> SEQUENCE: 397
acgcacttga cttgtcttcg rcttgtaagc tctttaactg mattag        46

<210> SEQ ID NO 398
<211> LENGTH: 36
<212> TYPE: DNA
<213> ORGANISM: Artificial Sequence
<220> FEATURE:
<223> OTHER INFORMATION: Primer

<400> SEQUENCE: 398
acccaactga atggagcgcc yatgacygga ttcaaa                   36

<210> SEQ ID NO 399
<211> LENGTH: 38
<212> TYPE: DNA
<213> ORGANISM: Artificial Sequence
<220> FEATURE:
<223> OTHER INFORMATION: Primer

<400> SEQUENCE: 399
acccaactga atggagctty gcacctatga ctggrttt   38

<210> SEQ ID NO 400
<211> LENGTH: 39
<212> TYPE: DNA
<213> ORGANISM: Artificial Sequence
<220> FEATURE:
<223> OTHER INFORMATION: Primer

<400> SEQUENCE: 400
acgcacttga cttgtcttcg gyttccatgt tgcttgaay   39

<210> SEQ ID NO 401
<211> LENGTH: 38
<212> TYPE: DNA
<213> ORGANISM: Artificial Sequence
<220> FEATURE:
<223> OTHER INFORMATION: Primer

<400> SEQUENCE: 401
acccaactga atggagctga rgctatccat ccaagrcc   38

<210> SEQ ID NO 402
<211> LENGTH: 39
<212> TYPE: DNA
<213> ORGANISM: Artificial Sequence
<220> FEATURE:
<223> OTHER INFORMATION: Primer

<400> SEQUENCE: 402
acccaactga atggagcgaa gctgtccatc caagattag   39

<210> SEQ ID NO 403
<211> LENGTH: 43
<212> TYPE: DNA
<213> ORGANISM: Artificial Sequence
<220> FEATURE:
<223> OTHER INFORMATION: Primer

<400> SEQUENCE: 403
acgcacttga cttgtcttcc ggtttagctt ggaatacaga tga   43

<210> SEQ ID NO 404
<211> LENGTH: 43
<212> TYPE: DNA
<213> ORGANISM: Artificial Sequence
<220> FEATURE:
<223> OTHER INFORMATION: Primer

<400> SEQUENCE: 404
acgcacttga cttgtcttcc ggttttgcct ggaataaaga tga   43

<210> SEQ ID NO 405
<211> LENGTH: 42
<212> TYPE: DNA
<213> ORGANISM: Artificial Sequence
<220> FEATURE:
<223> OTHER INFORMATION: Primer

<400> SEQUENCE: 405
acgcacttga cttgtcttcg gcytagcttg gaayatagat ga   42

<210> SEQ ID NO 406
<211> LENGTH: 38
<212> TYPE: DNA

<213> ORGANISM: Artificial Sequence
<220> FEATURE:
<223> OTHER INFORMATION: Primer

<400> SEQUENCE: 406
acccaactga atggagcgca atmggaaayt caacattc                38

<210> SEQ ID NO 407
<211> LENGTH: 42
<212> TYPE: DNA
<213> ORGANISM: Artificial Sequence
<220> FEATURE:
<223> OTHER INFORMATION: Primer

<400> SEQUENCE: 407
acgcacttga cttgtcttcc rcttgcaaat gggtctattc ct            42

<210> SEQ ID NO 408
<211> LENGTH: 37
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (20)..(20)
<223> OTHER INFORMATION: n is i

<400> SEQUENCE: 408
acccaactga atggagcggn tctggaayac ttgaagg                  37

<210> SEQ ID NO 409
<211> LENGTH: 37
<212> TYPE: DNA
<213> ORGANISM: Artificial Sequence
<220> FEATURE:
<223> OTHER INFORMATION: Primer

<400> SEQUENCE: 409
acccaactga atggagcgga tctggrrtrc ttgaagg                  37

<210> SEQ ID NO 410
<211> LENGTH: 37
<212> TYPE: DNA
<213> ORGANISM: Artificial Sequence
<220> FEATURE:
<223> OTHER INFORMATION: Primer

<400> SEQUENCE: 410
acccaactga atggagcggt tctggaascc ttgargg                  37

<210> SEQ ID NO 411
<211> LENGTH: 37
<212> TYPE: DNA
<213> ORGANISM: Artificial Sequence
<220> FEATURE:
<223> OTHER INFORMATION: Primer

<400> SEQUENCE: 411
acccaactga atggagcggr yctggggtrc ttgaagg                  37

<210> SEQ ID NO 412
<211> LENGTH: 39
<212> TYPE: DNA
<213> ORGANISM: Artificial Sequence
<220> FEATURE:
<223> OTHER INFORMATION: Primer

```
<400> SEQUENCE: 412
acccaactga atggagcgga tctgggggaa agcttgaag                              39

<210> SEQ ID NO 413
<211> LENGTH: 37
<212> TYPE: DNA
<213> ORGANISM: Artificial Sequence
<220> FEATURE:
<223> OTHER INFORMATION: Primer

<400> SEQUENCE: 413
acccaactga atggagcggt tctggdgtrc tkgaagg                                37

<210> SEQ ID NO 414
<211> LENGTH: 37
<212> TYPE: DNA
<213> ORGANISM: Artificial Sequence
<220> FEATURE:
<223> OTHER INFORMATION: Primer

<400> SEQUENCE: 414
acccaactga atggagcgga tctggmwhgc yygaagg                                37

<210> SEQ ID NO 415
<211> LENGTH: 37
<212> TYPE: DNA
<213> ORGANISM: Artificial Sequence
<220> FEATURE:
<223> OTHER INFORMATION: Primer

<400> SEQUENCE: 415
acccaactga atggagcggm gctggamawc ttgaagg                                37

<210> SEQ ID NO 416
<211> LENGTH: 43
<212> TYPE: DNA
<213> ORGANISM: Artificial Sequence
<220> FEATURE:
<223> OTHER INFORMATION: Primer

<400> SEQUENCE: 416
acgcacttga cttgtcttcc aagtytgktk ccrttttkctc ttg                        43

<210> SEQ ID NO 417
<211> LENGTH: 43
<212> TYPE: DNA
<213> ORGANISM: Artificial Sequence
<220> FEATURE:
<223> OTHER INFORMATION: Primer

<400> SEQUENCE: 417
acgcacttga cttgtcttcc aagyytggtw ccgtytgctc ttr                         43

<210> SEQ ID NO 418
<211> LENGTH: 43
<212> TYPE: DNA
<213> ORGANISM: Artificial Sequence
<220> FEATURE:
<223> OTHER INFORMATION: Primer

<400> SEQUENCE: 418
acgcacttga cttgtcttcc magtgtagty ccgyttgdtc ttg                         43

<210> SEQ ID NO 419
```

```
<211> LENGTH: 43
<212> TYPE: DNA
<213> ORGANISM: Artificial Sequence
<220> FEATURE:
<223> OTHER INFORMATION: Primer

<400> SEQUENCE: 419
acgcacttga cttgtcttcc aagtmtkgww ccrtttgctc ttr        43

<210> SEQ ID NO 420
<211> LENGTH: 43
<212> TYPE: DNA
<213> ORGANISM: Artificial Sequence
<220> FEATURE:
<223> OTHER INFORMATION: Primer

<400> SEQUENCE: 420
acgcacttga cttgtcttcc aagkgtagtt tcgtttkctc ttg        43

<210> SEQ ID NO 421
<211> LENGTH: 43
<212> TYPE: DNA
<213> ORGANISM: Artificial Sequence
<220> FEATURE:
<223> OTHER INFORMATION: Primer

<400> SEQUENCE: 421
acgcacttga cttgtcttcc aaktgtagta tyrtttgatc ttg        43

<210> SEQ ID NO 422
<211> LENGTH: 43
<212> TYPE: DNA
<213> ORGANISM: Artificial Sequence
<220> FEATURE:
<223> OTHER INFORMATION: Primer

<400> SEQUENCE: 422
acgcacttga cttgtcttcc aagmktrgtk ccgtttgctc ttg        43

<210> SEQ ID NO 423
<211> LENGTH: 43
<212> TYPE: DNA
<213> ORGANISM: Artificial Sequence
<220> FEATURE:
<223> OTHER INFORMATION: Primer

<400> SEQUENCE: 423
acgcacttga cttgtcttcc aagtctggtt ccgtcttttc ttg        43

<210> SEQ ID NO 424
<211> LENGTH: 43
<212> TYPE: DNA
<213> ORGANISM: Artificial Sequence
<220> FEATURE:
<223> OTHER INFORMATION: Primer

<400> SEQUENCE: 424
acgcacttga cttgtcttcc aagtggtgtt ccgtttgttc ttg        43

<210> SEQ ID NO 425
<211> LENGTH: 43
<212> TYPE: DNA
<213> ORGANISM: Artificial Sequence
<220> FEATURE:
<223> OTHER INFORMATION: Primer

<400> SEQUENCE: 425
```
acgcacttga cttgtcttcc aagtctattt ccatttgctc ttg                43

<210> SEQ ID NO 426
<211> LENGTH: 43
<212> TYPE: DNA
<213> ORGANISM: Artificial Sequence
<220> FEATURE:
<223> OTHER INFORMATION: Primer

<400> SEQUENCE: 426
acgcacttga cttgtcttcc aagtctggtt ccgttayctc tta                43

<210> SEQ ID NO 427
<211> LENGTH: 43
<212> TYPE: DNA
<213> ORGANISM: Artificial Sequence
<220> FEATURE:
<223> OTHER INFORMATION: Primer

<400> SEQUENCE: 427
acgcacttga cttgtcttcc aagtctggtt ccatttgccc tta                43

<210> SEQ ID NO 428
<211> LENGTH: 41
<212> TYPE: DNA
<213> ORGANISM: Artificial Sequence
<220> FEATURE:
<223> OTHER INFORMATION: Primer

<400> SEQUENCE: 428
acccaactga atggagctgt aattgcagaa acaccttttg a                  41

<210> SEQ ID NO 429
<211> LENGTH: 39
<212> TYPE: DNA
<213> ORGANISM: Artificial Sequence
<220> FEATURE:
<223> OTHER INFORMATION: Primer

<400> SEQUENCE: 429
acgcacttga cttgtcttcg ctgcttttga gatgtgtcc                     39

<210> SEQ ID NO 430
<211> LENGTH: 43
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (26)..(26)
<223> OTHER INFORMATION: n is i

<400> SEQUENCE: 430
acccaactga atggagcggc taaatnagta gttgcaaayg aca                43

<210> SEQ ID NO 431
<211> LENGTH: 36
<212> TYPE: DNA
<213> ORGANISM: Artificial Sequence
<220> FEATURE:
<223> OTHER INFORMATION: Primer

<400> SEQUENCE: 431
acgcacttga cttgtcttcg cttctgttgc caggtg                        36

<210> SEQ ID NO 432
<211> LENGTH: 38
<212> TYPE: DNA
<213> ORGANISM: Artificial Sequence
<220> FEATURE:
<223> OTHER INFORMATION: Primer

<400> SEQUENCE: 432
acccaactga atggagcacc gtccaaagct gataggtc                                38

<210> SEQ ID NO 433
<211> LENGTH: 41
<212> TYPE: DNA
<213> ORGANISM: Artificial Sequence
<220> FEATURE:
<223> OTHER INFORMATION: Primer

<400> SEQUENCE: 433
acgcacttga cttgtcttcc gaaactgcga atggctcatt a                            41

<210> SEQ ID NO 434
<211> LENGTH: 39
<212> TYPE: DNA
<213> ORGANISM: Artificial Sequence
<220> FEATURE:
<223> OTHER INFORMATION: Primer

<400> SEQUENCE: 434
acccaactga atggagcggc atttacttac rgtgstgat                               39

<210> SEQ ID NO 435
<211> LENGTH: 41
<212> TYPE: DNA
<213> ORGANISM: Artificial Sequence
<220> FEATURE:
<223> OTHER INFORMATION: Primer

<400> SEQUENCE: 435
acgcacttga cttgtcttcc catgatttgc agcaayagca t                            41

<210> SEQ ID NO 436
<211> LENGTH: 39
<212> TYPE: DNA
<213> ORGANISM: Artificial Sequence
<220> FEATURE:
<223> OTHER INFORMATION: Primer

<400> SEQUENCE: 436
acccaactga atggagccgy tagctgggct tagrtattc                               39

<210> SEQ ID NO 437
<211> LENGTH: 42
<212> TYPE: DNA
<213> ORGANISM: Artificial Sequence
<220> FEATURE:
<223> OTHER INFORMATION: Primer

<400> SEQUENCE: 437
acgcacttga cttgtcttcc gccgraactt tattcttgaa tg                           42

<210> SEQ ID NO 438
<211> LENGTH: 41
<212> TYPE: DNA
<213> ORGANISM: Artificial Sequence
<220> FEATURE:
<223> OTHER INFORMATION: Primer

<400> SEQUENCE: 438
acccaactga atggagcact tayggtggtg attataytat c                   41

<210> SEQ ID NO 439
<211> LENGTH: 41
<212> TYPE: DNA
<213> ORGANISM: Artificial Sequence
<220> FEATURE:
<223> OTHER INFORMATION: Primer

<400> SEQUENCE: 439
acgcacttga cttgtcttct gcagcaacag cattaktacy g                   41

<210> SEQ ID NO 440
<211> LENGTH: 38
<212> TYPE: DNA
<213> ORGANISM: Artificial Sequence
<220> FEATURE:
<223> OTHER INFORMATION: Primer

<400> SEQUENCE: 440
acccaactga atggagcgct graggagtag ctaatggt                       38

<210> SEQ ID NO 441
<211> LENGTH: 38
<212> TYPE: DNA
<213> ORGANISM: Artificial Sequence
<220> FEATURE:
<223> OTHER INFORMATION: Primer

<400> SEQUENCE: 441
acccaactga atggagcgca gcaggagtag ctgatgat                       38

<210> SEQ ID NO 442
<211> LENGTH: 40
<212> TYPE: DNA
<213> ORGANISM: Artificial Sequence
<220> FEATURE:
<223> OTHER INFORMATION: Primer

<400> SEQUENCE: 442
acgcacttga cttgtcttcm cgcagcagta ccggttaaag                     40

<210> SEQ ID NO 443
<211> LENGTH: 39
<212> TYPE: DNA
<213> ORGANISM: Artificial Sequence
<220> FEATURE:
<223> OTHER INFORMATION: Primer

<400> SEQUENCE: 443
acccaactga atggagccaa ccgcagcrwt aatgctaac                      39

<210> SEQ ID NO 444
<211> LENGTH: 41
<212> TYPE: DNA
<213> ORGANISM: Artificial Sequence
<220> FEATURE:
<223> OTHER INFORMATION: Primer

<400> SEQUENCE: 444
acgcacttga cttgtcttcc ctcccgtatc taccactgaa c                   41

<210> SEQ ID NO 445

```
<211> LENGTH: 37
<212> TYPE: DNA
<213> ORGANISM: Artificial Sequence
<220> FEATURE:
<223> OTHER INFORMATION: Primer

<400> SEQUENCE: 445
acccaactga atggagctgc aggagcagat aatggta                         37

<210> SEQ ID NO 446
<211> LENGTH: 39
<212> TYPE: DNA
<213> ORGANISM: Artificial Sequence
<220> FEATURE:
<223> OTHER INFORMATION: Primer

<400> SEQUENCE: 446
acgcacttga cttgtcttcg ccggcagtaa tagtaacag                       39

<210> SEQ ID NO 447
<211> LENGTH: 40
<212> TYPE: DNA
<213> ORGANISM: Artificial Sequence
<220> FEATURE:
<223> OTHER INFORMATION: Primer

<400> SEQUENCE: 447
acccaactga atggagcggt gcaagccaag taacatatac                      40

<210> SEQ ID NO 448
<211> LENGTH: 42
<212> TYPE: DNA
<213> ORGANISM: Artificial Sequence
<220> FEATURE:
<223> OTHER INFORMATION: Primer

<400> SEQUENCE: 448
acccaactga atggagcagg tacaaatcaa gtaacatata cc                   42

<210> SEQ ID NO 449
<211> LENGTH: 38
<212> TYPE: DNA
<213> ORGANISM: Artificial Sequence
<220> FEATURE:
<223> OTHER INFORMATION: Primer

<400> SEQUENCE: 449
acgcacttga cttgtcttca aaccgccttc cgtttctg                        38

<210> SEQ ID NO 450
<211> LENGTH: 38
<212> TYPE: DNA
<213> ORGANISM: Artificial Sequence
<220> FEATURE:
<223> OTHER INFORMATION: Primer

<400> SEQUENCE: 450
acgcacttga cttgtcttca atccacctgc cgcttctg                        38

<210> SEQ ID NO 451
<211> LENGTH: 39
<212> TYPE: DNA
<213> ORGANISM: Artificial Sequence
<220> FEATURE:
<223> OTHER INFORMATION: Primer

<400> SEQUENCE: 451
```
acccaactga atggagcggc dgtaggycat gtttatgac    39

<210> SEQ ID NO 452
<211> LENGTH: 39
<212> TYPE: DNA
<213> ORGANISM: Artificial Sequence
<220> FEATURE:
<223> OTHER INFORMATION: Primer

<400> SEQUENCE: 452
acccaactga atggagcagc tgtgggccac gtctatgac    39

<210> SEQ ID NO 453
<211> LENGTH: 39
<212> TYPE: DNA
<213> ORGANISM: Artificial Sequence
<220> FEATURE:
<223> OTHER INFORMATION: Primer

<400> SEQUENCE: 453
acgcacttga cttgtcttcc cgaaggcagg tgatctttg    39

<210> SEQ ID NO 454
<211> LENGTH: 39
<212> TYPE: DNA
<213> ORGANISM: Artificial Sequence
<220> FEATURE:
<223> OTHER INFORMATION: Primer

<400> SEQUENCE: 454
acgcacttga cttgtcttcc agaaggcagg tggtccttg    39

<210> SEQ ID NO 455
<211> LENGTH: 41
<212> TYPE: DNA
<213> ORGANISM: Artificial Sequence
<220> FEATURE:
<223> OTHER INFORMATION: Primer

<400> SEQUENCE: 455
acccaactga atggagccct gccaaatatg atgacatcaa g    41

<210> SEQ ID NO 456
<211> LENGTH: 38
<212> TYPE: DNA
<213> ORGANISM: Artificial Sequence
<220> FEATURE:
<223> OTHER INFORMATION: Primer

<400> SEQUENCE: 456
acgcacttga cttgtcttcg tggtcgttga gggcaatg    38

<210> SEQ ID NO 457
<211> LENGTH: 38
<212> TYPE: DNA
<213> ORGANISM: Artificial Sequence
<220> FEATURE:
<223> OTHER INFORMATION: Primer

<400> SEQUENCE: 457
acccaactga atggagcacc agargaagcc atacaaac    38

<210> SEQ ID NO 458
<211> LENGTH: 40
<212> TYPE: DNA

```
<213> ORGANISM: Artificial Sequence
<220> FEATURE:
<223> OTHER INFORMATION: Primer

<400> SEQUENCE: 458
acccaactga atggagctga cacttcaagc aatgttcgta                    40

<210> SEQ ID NO 459
<211> LENGTH: 35
<212> TYPE: DNA
<213> ORGANISM: Artificial Sequence
<220> FEATURE:
<223> OTHER INFORMATION: Primer

<400> SEQUENCE: 459
acccaactga atggagcaac gccgaacttg gtgtg                         35

<210> SEQ ID NO 460
<211> LENGTH: 36
<212> TYPE: DNA
<213> ORGANISM: Artificial Sequence
<220> FEATURE:
<223> OTHER INFORMATION: Primer

<400> SEQUENCE: 460
acccaactga atggagcaac accgaaccag aggaag                        36

<210> SEQ ID NO 461
<211> LENGTH: 42
<212> TYPE: DNA
<213> ORGANISM: Artificial Sequence
<220> FEATURE:
<223> OTHER INFORMATION: Primer

<400> SEQUENCE: 461
acgcacttga cttgtcttct gacacttcaa gcaatgttcg ta                 42

<210> SEQ ID NO 462
<211> LENGTH: 37
<212> TYPE: DNA
<213> ORGANISM: Artificial Sequence
<220> FEATURE:
<223> OTHER INFORMATION: Primer

<400> SEQUENCE: 462
acgcacttga cttgtcttca acgccgaact tggtgtg                       37

<210> SEQ ID NO 463
<211> LENGTH: 38
<212> TYPE: DNA
<213> ORGANISM: Artificial Sequence
<220> FEATURE:
<223> OTHER INFORMATION: Primer

<400> SEQUENCE: 463
acgcacttga cttgtcttca acaccgaacc agaggaag                      38

<210> SEQ ID NO 464
<211> LENGTH: 40
<212> TYPE: DNA
<213> ORGANISM: Artificial Sequence
<220> FEATURE:
<223> OTHER INFORMATION: Primer

<400> SEQUENCE: 464
acgcacttga cttgtcttcs ctgaytgcca rtggaatgaa                    40
```

<210> SEQ ID NO 465
<211> LENGTH: 43
<212> TYPE: DNA
<213> ORGANISM: Artificial Sequence
<220> FEATURE:
<223> OTHER INFORMATION: Primer

<400> SEQUENCE: 465
acgcacttga cttgtcttca tgtgctgtta ttgctaccta ctg        43

<210> SEQ ID NO 466
<211> LENGTH: 40
<212> TYPE: DNA
<213> ORGANISM: Artificial Sequence
<220> FEATURE:
<223> OTHER INFORMATION: Primer

<400> SEQUENCE: 466
acccaactga atggagctag cgttggtatt aagtggttgt        40

<210> SEQ ID NO 467
<211> LENGTH: 40
<212> TYPE: DNA
<213> ORGANISM: Artificial Sequence
<220> FEATURE:
<223> OTHER INFORMATION: Primer

<400> SEQUENCE: 467
acgcacttga cttgtcttct caaatccagc aaagccatca        40

<210> SEQ ID NO 468
<211> LENGTH: 40
<212> TYPE: DNA
<213> ORGANISM: Artificial Sequence
<220> FEATURE:
<223> OTHER INFORMATION: Primer

<400> SEQUENCE: 468
acccaactga atggagcaag accaatyctg tcacctctga        40

<210> SEQ ID NO 469
<211> LENGTH: 42
<212> TYPE: DNA
<213> ORGANISM: Artificial Sequence
<220> FEATURE:
<223> OTHER INFORMATION: Primer

<400> SEQUENCE: 469
acgcacttga cttgtcttct agcgttggta ttaagtggtt gt        42

<210> SEQ ID NO 470
<211> LENGTH: 40
<212> TYPE: DNA
<213> ORGANISM: Artificial Sequence
<220> FEATURE:
<223> OTHER INFORMATION: Primer

<400> SEQUENCE: 470
acccaactga atggagcgaa aggagtgcgg gtaataggtt        40

<210> SEQ ID NO 471
<211> LENGTH: 42
<212> TYPE: DNA
<213> ORGANISM: Artificial Sequence
<220> FEATURE:

<223> OTHER INFORMATION: Primer

<400> SEQUENCE: 471
acgcacttga cttgtcttca agaccaatyc tgtcacctct ga         42

<210> SEQ ID NO 472
<211> LENGTH: 36
<212> TYPE: DNA
<213> ORGANISM: Artificial Sequence
<220> FEATURE:
<223> OTHER INFORMATION: Primer

<400> SEQUENCE: 472
acccaactga atggagccat tggacggcat cacgat               36

<210> SEQ ID NO 473
<211> LENGTH: 42
<212> TYPE: DNA
<213> ORGANISM: Artificial Sequence
<220> FEATURE:
<223> OTHER INFORMATION: Primer

<400> SEQUENCE: 473
acgcacttga cttgtcttcg aaaggagtgc gggtaatagg tt         42

<210> SEQ ID NO 474
<211> LENGTH: 46
<212> TYPE: DNA
<213> ORGANISM: Artificial Sequence
<220> FEATURE:
<223> OTHER INFORMATION: Primer

<400> SEQUENCE: 474
acccaactga atggagccta agccataagc cctttctcta acttgt     46

<210> SEQ ID NO 475
<211> LENGTH: 38
<212> TYPE: DNA
<213> ORGANISM: Artificial Sequence
<220> FEATURE:
<223> OTHER INFORMATION: Primer

<400> SEQUENCE: 475
acgcacttga cttgtcttcc attggacggc atcacgat              38

<210> SEQ ID NO 476
<211> LENGTH: 13
<212> TYPE: DNA
<213> ORGANISM: Artificial Sequence
<220> FEATURE:
<223> OTHER INFORMATION: Primer

<400> SEQUENCE: 476
atggccctat cat                                         13

<210> SEQ ID NO 477
<211> LENGTH: 13
<212> TYPE: DNA
<213> ORGANISM: Artificial Sequence
<220> FEATURE:
<223> OTHER INFORMATION: Primer

<400> SEQUENCE: 477
atggctttat aat                                         13

SYSTEMS AND METHODS FOR THE DETECTION OF INFECTIOUS DISEASES

CROSS REFERENCE TO RELATED APPLICATIONS

This application claims priority to U.S. Provisional Patent Application No. 62/293,873, filed Feb. 11, 2016, the contents of which are incorporated herein by reference in their entirety.

REFERENCE TO SEQUENCE LISTING SUBMITTED ELECTRONICALLY

The official copy of the sequence listing is submitted electronically via EFS-Web as an ASCII-formatted sequence listing with a file named "91482_201_Sequence_Listing.txt" created on Feb. 9, 2017, and having a size of 85 kilobytes, and is filed concurrently with the specification. The sequence listing contained in this ASCII-formatted document is part of the specification and is herein incorporated by reference in its entirety.

TECHNICAL FIELD

The present invention relates to the field of detection of *Borrelia* species that cause Lyme Disease and tick-borne relapsing fever in samples from a subject.

BACKGROUND

Lyme disease, also known as Lyme borreliosis, is caused by infection with the bacterial spirochete *Borrelia burgdorferi*, which is transmitted by the bite of *Ixodes* ticks. *Borrelia burgdorferi*, *Borrelia garinii* and *Borrelia afzelii* cause Lyme disease in Eurasia and *Borrelia burgdorferi* and *Borrelia mayonii* cause Lyme disease in the United States and Canada. *B. garinii* has been found in pelagic bird colonies off the coast of North America, so there may be potential for infection by this agent in North America. The four Lyme disease agents *Borrelia burgdorferi*, *Borrelia mayonii*, *Borrelia garinii* and *Borrelia afzelii* are referred to as *Borrelia burgdorferi* sensu lato, that is, "in the broad sense." The North American genospecies *Borrelia burgdorferi* is called *Borrelia burgdorferi* sensu stricto, "in the strict sense."

Lyme disease is characterized by three stages: 1) early localized Lyme disease; 2) early disseminated Lyme disease; and 3) late disseminated Lyme disease. A subject may be suspected of having Lyme disease where symptoms are consistent with those of Lyme disease and where an *Ixodes* tick bite is known or may have occurred. A characteristic rash called erythema migrans occurs in 70-80% of Lyme disease patients at the site of an infected tick bite.

Early localized Lyme disease is characterized by erythema migrans. Early disseminated Lyme disease typically occurs days to weeks after the initial bite by an infected tick and possible signs include secondary erythema migrans, early neuroborreliosis (cranial nerve palsy, meningitis, or radiculoneuropathy) or, uncommonly, Lyme carditis (atrioventricular node conduction block). Non-specific symptoms such as malaise, fever, headache, and muscle and joint pains may be present. Late disseminated Lyme disease occurs months to years after the initial bite by an infected tick. The most common manifestation of late disseminated Lyme disease in North America is Lyme arthritis, which is characterized by intermittent attacks in large joints, particularly the knees. Rarely, late neuroborreliosis develops, with manifestations including encephalopathy, encephalomyelitis, and/or peripheral neuropathy. Wormser, G. P., et al. Clin Infect Dis 2006; 43:1089-1134.

Lyme arthritis is a late manifestation of Lyme disease affecting up to 60% of untreated patients in the United States. Ten percent of patients treated with antibiotics continue to suffer from recurrent bouts of Lyme arthritis, Steere, A. C. and L. Glickstein, Nat Rev Immunol, 2004. 4(2): p. 143-52. Cartilage loss and subsequent bone destruction which are features of osteoarthritis and rheumatoid arthritis also occur in advanced cases of Lyme arthritis, Lawson, J. P. et al., Radiology, 1985, 154(1):37-43. Lyme arthritis develops when the bacteria invade joint tissue, most commonly the knee, and trigger inflammation as part of a strong host immune response. Despite this vigorous immune response, *Borrelia* are able to persist in joints which are thought to be a protective niche for the bacteria due to limited perfusion, Liang, F. T., et al., Am J Pathol, 2004, 165(3):977-85.

The detection and management of the disease is complicated by several factors, limiting the ability of clinical medicine to rapidly identify patients and subsequently employ appropriate therapy. Important complicating factors in the diagnosis of Lyme borreliosis infection include:

1. Co-infection: *Ixodes* ticks may transmit multiple pathogens while taking a blood meal, which may result in co-infection and confounding symptoms and test results;
2. Unspecific testing: multiple *Borrelia* species are now known and other unknown *Borrelias* likely exist, all of which may cause false positives on Lyme disease diagnostic tests; and
3. Limited sensitivity: *Borrelia* infections result in typically low-level bacteremia, and therefore limited target material may be present in clinical samples.

Another complicating factor is the difficulty of detecting active infection with the causative agent of Lyme disease in cases where symptoms are present long after potential exposure to infected ticks. There is a continuing need for compositions and methods for the diagnosis of Lyme disease that address these challenges to rapid detection and treatment.

SUMMARY

The present invention is directed to a method of detecting one or more *Borrelia* species causing Lyme Disease or tick-borne relapsing fever (TBRF) within a sample from a subject, the method comprising: a) subjecting DNA and/or RNA from the sample to a PCR amplification reaction using primer pairs targeting at least one region of *Borrelia* 16S rRNA and at least one region of flaB, ospA, ospB, ospC, glpQ, 16S-23S intergenic spacer (IGS1), 5S-23S intergenic spacer (IGS2), bbk32, dbpA, dbpB, and/or p66; and b) analyzing amplification products resulting from the PCR amplification reaction to detect the one or more *Borrelia* species.

In certain aspects, the primer pairs targeting at least one region of *Borrelia* 16S rRNA contain sequences selected from the group consisting of SEQ ID NOS: 1-10. In other aspects, RNA from the sample is subject to the PCR amplification reaction with the primer pairs targeting at least one region of *Borrelia* 16S rRNA.

In yet other aspects, the primer pairs targeting at least one region of flaB, ospA, ospB, ospC, glpQ, 16S-23S intergenic spacer (IGS), 5S-23S intergenic spacer (IGS2), bbk32, dbpA, dbpB, and/or p66 contain sequences selected from the group consisting of SEQ ID NOS: 11-48, SEQ ID NOS: 60-77, SEQ ID NOS: 97-100, and SEQ ID NOS: 219-293.

In one embodiment, the PCR amplification reaction is a multiplex amplification reaction. In another embodiment, the amplification products are analyzed by size determination with agarose gel electrophoresis.

In some embodiments, the amplification products are analyzed by next-generation sequencing (NGS) to determine the sequence of each amplification product. In one embodiment, the primer pairs comprise a universal tail sequence.

In certain aspects, the sequence of each amplification product is mapped to a reference library of known *Borrelia* sequences to detect the one or more *Borrelia* species. In other aspects, the one or more *Borrelia* species are selected from the group consisting of *Borrelia afzelii, Borrelia americana, Borrelia andersonii, Borrelia anserina, Borrelia baltazardii, Borrelia bavariensis, Borrelia bissettii, Borrelia brasiliensis, Borrelia burgdorferi, Borrelia californiensis, Borrelia carolinensis, Borrelia caucasica, Borrelia coriaceae, Borrelia crocidurae, Borrelia dugesii, Borrelia duttonii, Borrelia garinii, Borrelia graingeri, Borrelia harveyi, Borrelia hermsii, Borrelia hispanica, Borrelia japonica, Borrelia kurtenbachii, Borrelia latyschewii, Borrelia lonestari, Borrelia lusitaniae, Borrelia mayonii, Borrelia mazzottii, Borrelia merionesi, Borrelia microti, Borrelia miyamotoi, Borrelia parkeri, Borrelia persica, Borrelia queenslandica, Borrelia recurrentis, Borrelia sinica, Borrelia spielmanii, Borrelia tanukii, Borrelia theileri, Borrelia tillae, Borrelia turcica, Borrelia turdi, Borrelia turicatae, Borrelia valaisiana, Borrelia venezuelensis, Borrelia vincentii,* and *Candidatus Borrelia texasensis*. In one aspect, the one or more *Borrelia* species are *Borrelia burgdorferi, Borrelia garinii, Borrelia mayonii,* and/or *Borrelia afzelii*.

In some embodiments, the method further comprises detecting in the sample a *Babesia* species, an *Ehrlichia* species, a *Bartonella* species, *Francisella tularensis, Yersinia pestis, Staphylococcus aureus, Anaplasma phagocytophilum*, Enterovirus, Powassan and deer tick virus, *Rickettsia* species, and/or *Influenza* by subjecting DNA and/or RNA from the sample to a PCR amplification reaction using primer pairs containing sequences selected from the group consisting of SEQ ID NOS: 49-59, SEQ ID NOS: 78-96, SEQ ID NOS: 105-108, and SEQ ID NOS: 294-314.

In other aspects, the sample is whole blood, serum, plasma, buffy coat or connective tissue.

In some embodiments, the subject is an animal. In one embodiment, the animal is a human. In another embodiment, the template is RNA.

In some embodiments, the present invention is directed to a kit for detection of one or more *Borrelia* species causing Lyme Disease or TBRF, the kit comprising: primer pairs targeting at least one region of *Borrelia* 16S rRNA and at least one region of flaB, ospA, ospB, ospC, glpQ, 16S-23S intergenic spacer (IGS1), 5S-23S intergenic spacer (IGS2), bbk32, dbpA, dbpB, and/or p66.

In one embodiment, the primer pairs in the kit targeting at least one region of *Borrelia* 16S rRNA contain sequences selected from the group consisting of SEQ ID NOS: 1-10.

In certain aspects, the primer pairs in the kit targeting at least one region of flaB, ospA, ospB, ospC, glpQ, 16S-23S intergenic spacer (IGS), 5S-23S intergenic spacer (IGS2), bbk32, dbpA, dbpB, and/or p66 contain sequences selected from the group consisting of SEQ ID NOS: 11-48, SEQ ID NOS: 60-77, SEQ ID NOS: 97-100, and SEQ ID NOS: 219-293.

In other aspects, the kit further comprises primer pairs containing sequences selected from the group consisting of SEQ ID NOS: 49-59, SEQ ID NOS: 78-96, SEQ ID NOS: 105-108, and SEQ ID NOS: 294-314.for detecting a *Babesia* species, an *Ehrlichia* species, a *Bartonella* species, *Francisella tularensis, Yersinia pestis, Staphylococcus aureus, Anaplasma phagocytophilum*, Enterovirus, Powassan and deer tick virus, *Rickettsia* species, and/or *Influenza*.

In yet other aspects, the primer pairs in the kit comprise a universal tail sequence. In one aspect, the kit further comprises a nucleotide polymerase, buffer, diluent, and/or excipient.

In one aspect, the kit further comprises one or more primers comprising a sequence selected from SEQ ID NOS: 109 and 110 for amplifying human GAPDH as an internal control.

BRIEF DESCRIPTION OF THE DRAWINGS

FIG. 6 depicts mapping of *Borrelia* 16S rDNA sequence reads against 185 unique DNA sequences to identify *Borrelia* species that cause Lyme Disease and *Borrelia* species that do not cause Lyme Disease. The arrows depict forward and reverse primers that produce amplicons covering the majority of the *Borrelia* 16S rDNA sequence.

DETAILED DESCRIPTION

Figure 1:
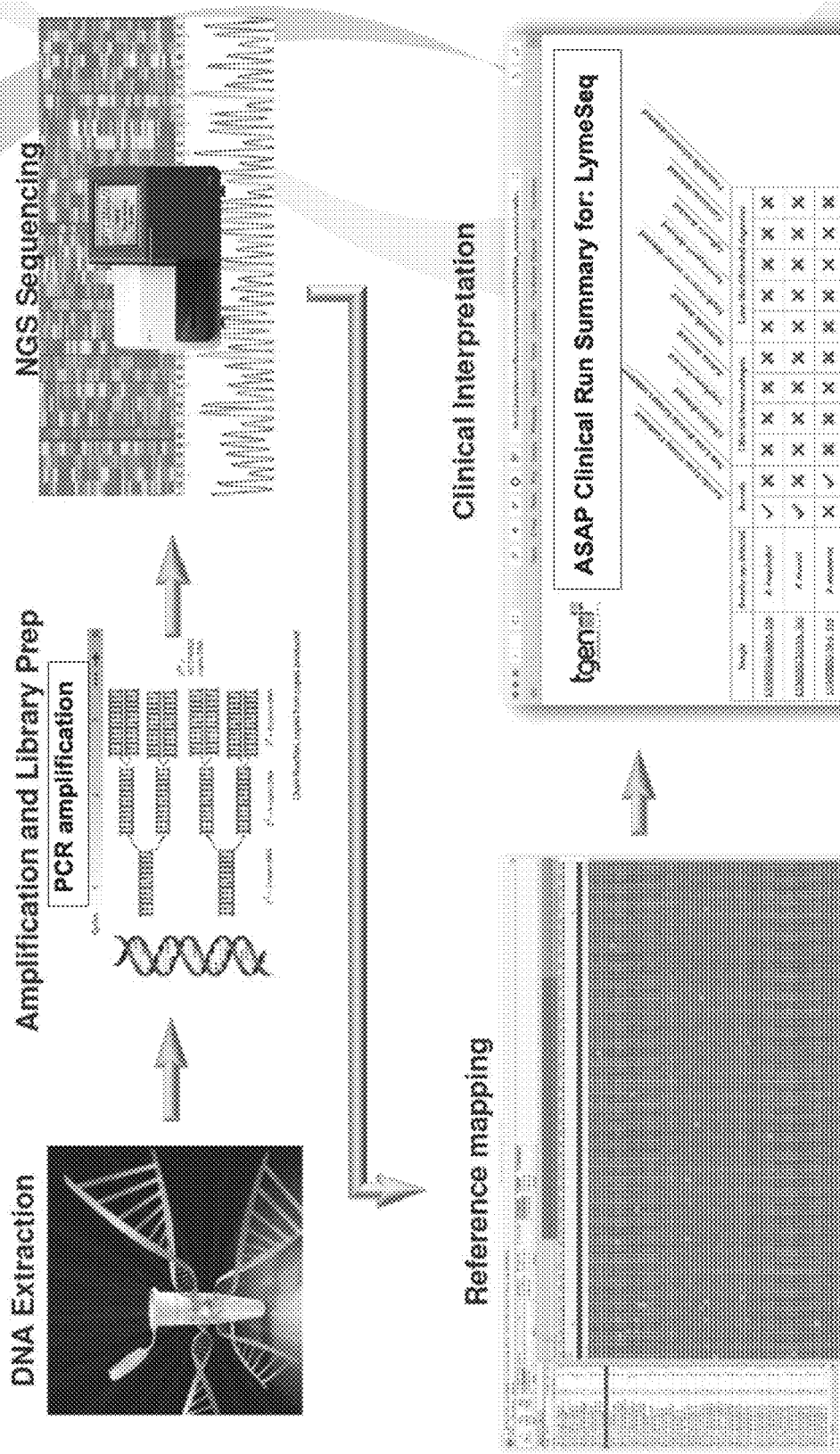
FIG. 1 depicts a workflow for the LymeSeq Lyme Disease Next-Generation Sequencing Diagnostic Assay.

The present invention provides a method of detecting and characterizing one or more *Borrelia* species causing Lyme Disease or TBRF within a sample from a subject and addresses the challenges of co-infection that may confound test results, unspecific testing causing false positives on Lyme disease diagnostic tests, and the limited sensitivity available with other methods of detection.

The present invention overcomes these challenges by providing a method A method of detecting one or more *Borrelia* species causing Lyme Disease or tick-borne relapsing fever (TBRF) within a sample from a subject, the method comprising: a) subjecting DNA and/or RNA from the sample to a PCR amplification reaction using primer pairs targeting at least one region specific to the *Borrelia* genus, at least one region specific to *Borrelia* burgdorferi, and/or at least one non-Lyme *Borrelia* spp. region; and b) analyzing amplification products resulting from the PCR amplification reaction to detect the one or more *Borrelia* species.

In some embodiments, the primer pairs of the present invention target at least one region of an outer surface protein gene of *Borrelia burgdorferi*. The *Borrelia burgdorferi* outer surface proteins include ospA, ospB, ospD, ospC, bba64, ospF, bbk32, dbpA, dbpB, and vlsE. *Borrelia burgdorferi* outer surface proteins play role in persistence within ticks (ospA, ospB, ospD), mammalian host transmission (ospC, bba64), host cell adhesion (ospF, bbk32, dbpA, dbpB), and in evasion of the host immune system (vlsE). OspC triggers innate immune system via signaling through TLR1, TLR2 and TLR6 receptors. See Oosting, Marije et al. (2016) "Innate immunity networks during infection with *Borrelia burgdorferi*," Critical Reviews in Microbiology 42 (2): 233-244.

In certain aspects, the primer pairs of the present invention target at least one region of an intergenic spacer (IGS) region. An IGS region is a region of non-coding DNA between genes and includes the spacer DNA between the many tandemly repeated copies of the ribosomal RNA genes. In one aspect, the IGS region is the region between the 16S and the 23S genes (i.e., 16S-23S intergenic spacer (IGS1)) and/or the region between the 5S and the 23S genes (i.e., 5S-23S intergenic spacer (IGS2)).

In other aspects, the primer pairs of the present invention target at least one region of a porin gene in *Borrelia burgdorferi*. In some embodiments, the porin gene is selected from the group consisting of p66, p13 and oms28. In one aspect, the porin gene is p66.

In yet other aspects, the primer pairs of the present invention target at least one region of a glycerophosphodiester phosphodiesterase gene (glpQ) from *Borrelia* spp.

In some embodiments, the primer pairs of the present invention target at least one region of ospA, ospC, CRASP (complement regulator-acquiring surface protein) including CRASP-1 (cspA), CRASP-2 (cspZ), CRASP-3 (erpP), CRASP-4 (erpC), CRASP-5 (erpA), Erp (OspEF-related protein) A, C, and P, bbk32, dbp (decorin-binding proteins) A and B, bgp (*Borrelia* glycosaminoglycan-binding protein), revA, revB, bb0347, erpX, p66, bbb07, ospC, vlsE, lmp1, and/or ospF family (ospF and G, erpK and L). See Coburn, J., et al. (2013) "Illuminating the roles of the *Borrelia burgdorferi* adhesins," Trends in Microbiology, 21(8), 372-379.

As used herein, "amplification reaction" refers to a method of detecting target nucleic acid by in vitro amplification of DNA or RNA.

As used herein, "polymerase chain reaction (PCR)" refers to the amplification of a specific DNA sequence, termed target or template sequence, that is present in a mixture, by adding two or more short oligonucleotides, also called primers, that are specific for the terminal or outer limits of the template sequence. The template-primers mixture is subjected to repeated cycles of heating to separate (melt) the double-stranded DNA and cooling in the presence of nucleotides and DNA polymerase such that the template sequence is copied at each cycle.

The term "primer" refers to DNA oligonucleotides complementary to a region of DNA and serves as the initiation of amplification reaction from the 5' to 3' direction.

The term "primer pair" refers to the forward and reverse primers in an amplification reaction leading to amplification of a double-stranded DNA region of the target.

The term "target" refers to a nucleic acid region bound by a primer pair that is amplified through an amplification reaction. The PCR "product" or "amplicon" is the amplified nucleic acid resulting from PCR of a set of primer pairs.

The term "multiplex amplification reaction" herein refers to the detection of more than one template in a mixture by the addition of more than one set of oligonucleotide primers.

As described in greater detail herein, some embodiments of the invention may include amplicon-based sequencing of the one or more markers to make the aforementioned determinations. Some embodiments of the invention include systems and methods of preparing samples for one or more downstream processes that can be used for assessing one or more markers for any of the previously mentioned purposes. Some embodiments of the invention may comprise a universal indexing sequencing strategy for use in downstream sequencing platform processes. By way of example only, some embodiments of the invention comprise a universal indexing sequencing strategy that can be used to amplify multiple genomic regions (e.g., markers, as described below) from a DNA sample simultaneously in a single reaction for the sequencing of one or more amplicons. One or more embodiments of the invention can be used with any desired sequencing platform, such as the ILLUMINA® Next Generation Sequencing (e.g., MiSEQ) platform, Life Technologies' Ion Torrent System, or any other sequencing system now known or developed in the future.

Some embodiments may be configured to enable relatively simple, rapid (e.g., microorganism-culture independent), inexpensive, and efficient preparation of samples for use on, in, and/or with downstream sequencing platforms. For example, some embodiments may use a sequence coupled to one or more oligonucleotides/primers (as used herein, oligonucleotides and primers are used interchangeably). More specifically, one or more amplicons per sample can be generated using a hybrid oligonucleotide that is designed for amplification of a marker and incorporation of at least one universal tail sequence into the resulting amplicon. As a result, additional steps that may be conventionally required to prepare samples for sequencing can be limited or removed entirely. Further information regarding the universal tail, amplicon-based sequencing strategy can be found in PCT/US2014/064890, which is hereby incorporated by reference in its entirety for all purposes.

In some embodiments, the methodology may include performing downstream sequencing on one or more amplicons. For example, in order to minimize and/or eliminate the need for cultures of microorganisms or large inputs of nucleic acids, methodologies of the instant invention may include an initial PCR step to create amplicons that correspond to the one or more pre-selected markers. As such, some embodiments require only limited amounts of starting material are necessary and the starting material need not be of high quality (e.g., genomic DNA, crude DNA extracts, single stranded DNA, RNA, cDNA, etc.). In contrast, many conventional sample preparation systems may require relatively large amounts of starting material of relatively high quality, which can limit the use of some conventional systems.

Some embodiments of the invention can be used for and/or in complement with high-throughput amplicon sequencing of markers, which can be very useful for a variety of molecular genetic genotyping/predicted-phenotyping applications, including clinical sample analysis. For example, use of the systems and methods of the invention can be employed with sequencing platforms to provide rapid, high-yield sequence data, which can enable the sequencing of multiple markers/amplicons from many samples in a relatively short period of time. Specifically, in some embodiments, amplicons can be selected and PCR reactions can be designed to provide information that can be used to make clinically relevant determinations after sequencing of the amplicons.

In some preferred aspects, the methodology may include creating a series of oligonucleotides designed to provide multiplexed amplification of one or more markers to produce the desired amplicons. In particular, the one or more markers and amplicons thereof can be selected/amplified to provide users with clinically relevant information related to identification of one or more potentially infectious microorganisms and/or viruses and phenotypic and genotypic information about the microorganisms and/or viruses (e.g., *Borrelia* strain identity and 16S-23S intergenic spacer (IGS) sequence variance). After production of the amplicons (e.g., via PCR amplification), which may include the universal tail sequences, the method may include processing the resulting amplicons for downstream sequencing and thereafter sequencing the processed amplicons. After processing and analysis of the resulting sequencing data, one of skill in the art can make any necessary determinations regarding the identification of one or more microorganisms and/or viruses that may have been contained within the sample and predicted-phenotypic and/or genotypic information revealed.

Generally, some embodiments of the present invention can be used to detect, identify, assess, sequence, or otherwise evaluate a marker. A marker may be any molecular structure produced by a cell, expressed inside the cell, accessible on the cell surface or secreted by the cell. A marker may be any protein, carbohydrate, fatty acid, nucleic acid, catalytic site, or any combination of these such as an enzyme, glycoprotein, cell membrane, virus, a particular cell, or other uni- or multimolecular structure. A marker may be represented by a sequence of a nucleic acid or any other molecules derived from the nucleic acid. Examples of such nucleic acids include miRNA, tRNA, siRNA, mRNA, cDNA, genomic DNA sequences, single-stranded DNA, or complementary sequences thereof. Alternatively, a marker may be represented by a protein sequence. The concept of a marker is not limited to the exact nucleic acid sequence or protein sequence or products thereof; rather it encompasses all molecules that may be detected by a method of assessing the marker. Without being limited by the theory, the detection, identification, assessment, sequencing, or any other evaluation of the marker may encompass an assessment of a change in copy number (e.g., copy number of a gene or other forms of nucleic acid) or in the detection of one or more translocations. Moreover, in some embodiments, the marker may be relevant to a particular phenotype or genotype. By way of example only, in some embodiments, the marker may be related to phenotypes including antibiotic resistance, virulence, or any other phenotype.

Therefore, examples of molecules encompassed by a marker represented by a particular sequence further include alleles of the gene used as a marker. An allele includes any form of a particular nucleic acid that may be recognized as a form of the particular nucleic acid on account of its location, sequence, or any other characteristic that may identify it as being a form of the particular gene. Alleles include but need not be limited to forms of a gene that include point mutations, silent mutations, deletions, frameshift mutations, single nucleotide polymorphisms (SNPs), inversions, translocations, heterochromatic insertions, and differentially methylated sequences relative to a reference gene, whether alone or in combination. An allele of a gene may or may not produce a functional protein; may produce a protein with altered function, localization, stability, dimerization, or protein-protein interaction; may have overexpression, underexpression or no expression; may have altered temporal or spatial expression specificity; or may have altered copy number (e.g., greater or less numbers of copies of the allele). An allele may also be called a mutation or a mutant. An allele may be compared to another allele that may be termed a wild type form of an allele. In some cases, the wild type allele is more common than the mutant.

In some aspects, the markers may include one or more sets of amplifiable nucleic acids that can provide diagnostic information about the microorganisms and/or viruses. For example, the markers may include amplifiable nucleic acid sequences that can be used to assess the presence and/or absence of one or more microorganism and/or virus that may have the potential to cause a diseased state in the subject. In some embodiments, the markers may include amplifiable nucleic acid sequences that can be used to identify one or more of the following exemplary microorganisms and/or viruses: *Borrelia* spp. (including but not limited to *Borrelia afzelii, Borrelia americana, Borrelia andersonii, Borrelia anserina, Borrelia baltazardii, Borrelia bavariensis, Borrelia bissettii, Borrelia brasiliensis, Borrelia burgdorferi, Borrelia californiensis, Borrelia carolinensis, Borrelia caucasica, Borrelia coriaceae, Borrelia crocidurae, Borrelia dugesii, Borrelia duttonii, Borrelia garinii, Borrelia graingeri, Borrelia harveyi, Borrelia hermsii, Borrelia hispanica, Borrelia japonica, Borrelia kurtenbachii, Borrelia latyschewii, Borrelia lonestari, Borrelia lusitaniae, Borrelia mayonii, Borrelia mazzottii, Borrelia merionesi, Borrelia microti, Borrelia miyamotoi, Borrelia parkeri, Borrelia persica, Borrelia queenslandica, Borrelia recurrentis, Borrelia sinica, Borrelia spielmanii, Borrelia tanukii, Borrelia theileri, Borrelia tillae, Borrelia turcica, Borrelia turdi, Borrelia turicatae, Borrelia valaisiana, Borrelia venezuelensis, Borrelia vincentii*, and *Candidatus Borrelia texasensis*), *Anaplasma phagocytophilum, Ehrlichia* spp., *Staphylococcus aureus, Yersinia pestis, Francisella tularensis, Bartonella* spp., *Babesia* spp., *Influenza* virus, and Enterovirus.

In some embodiments, the methods may include the use of one or more than one marker per microorganism or virus. Moreover, in some embodiments, one or more of the microorganisms and/or viruses may not be considered pathogenic to certain subjects, but the methodology employed herein can still rely on detection of pathogenic and non-pathogenic microorganisms and/or viruses for differential diagnoses/diagnostics. In some embodiments, the oligonucleotides (with or without the universal tail sequences detailed herein) listed in Table 1, Table 2, and Table 3 can be used with embodiments of the invention to amplify one or more markers from the microorganisms and/or viruses to provide diagnostic/identification information to the user.

Moreover, in some embodiments, one or more the markers associated with the plurality of microorganisms and/or viruses can be amplified in a multiplex manner. For example, in some aspects, nucleic acids can be obtained from the sample and the oligonucleotides used to amplify one or more of the markers used to identify/diagnose can be added to a single mixture to produce a plurality of amplicons in a single reaction mixture. In other aspects, the oligonucleotides can be added to multiple mixtures to provide for the creation of multiple amplicons in multiple mixtures.

Moreover, in some embodiments, one or more the markers can be amplified in a multiplex manner. For example, in some aspects, nucleic acids can be obtained from the sample and the oligonucleotides used to amplify one or more of the markers used to identify the strain of the microorganism or virus can be added to a single mixture to produce a plurality of amplicons in a single reaction mixture. In other aspects, the oligonucleotides can be added to multiple mixtures to provide for the creation of multiple amplicons in multiple mixtures. In some aspects, amplification of the markers used to identify microorganisms and/or viruses/diagnose an infection can also occur in a multiplex manner such that some or all of the amplicons are generated in a single reaction for a particular sample. In other aspects, amplification of the markers used to identify microorganisms and/or viruses/diagnose an infection can occur in multiple reaction vessels. Overall, as described in greater detail below, regardless of the multiplex nature of some embodiments of the invention, after amplification of the markers, the method may include processing and sequencing the resulting amplicons to provide information related to the identification, characterization, and strain identity of one or more microorganisms and/or viruses that may be present within the sample.

Some embodiments of the invention may comprise the use of one or more methods of amplifying a nucleic acid-based starting material (i.e., a template, including genomic DNA, crude DNA extract, single-stranded DNA, double-stranded DNA, cDNA, RNA, or any other single-stranded or double-stranded nucleic acids). Nucleic acids may be selectively and specifically amplified from a template nucleic acid contained in a sample. In some nucleic acid amplification methods, the copies are generated exponentially. Examples of nucleic acid amplification methods known in the art include: polymerase chain reaction (PCR), ligase chain reaction (LCR), self-sustained sequence replication (3SR), nucleic acid sequence based amplification (NASBA), strand displacement amplification (SDA), amplification with Qβ replicase, whole genome amplification with enzymes such as φ29, whole genome PCR, in vitro transcription with T7 RNA polymerase or any other RNA polymerase, or any other method by which copies of a desired sequence are generated.

In addition to genomic DNA, any polynucleotide sequence can be amplified with an appropriate set of primer molecules. In particular, the amplified segments created by the PCR process itself are, themselves, efficient templates for subsequent PCR amplifications.

PCR generally involves the mixing of a nucleic acid sample, two or more primers or oligonucleotides (primers and oligonucleotides are used interchangeably herein) that are designed to recognize the template DNA, a DNA polymerase, which may be a thermostable DNA polymerase such as Taq or Pfu, and deoxyribose nucleoside triphosphates (dNTP's). In some embodiments, the DNA polymerase used can comprise a high fidelity Taq polymerase such that the error rate of incorrect incorporation of dNTPs is less than one per 1,000 base pairs. Reverse transcription PCR, quantitative reverse transcription PCR, and quantitative real time reverse transcription PCR are other specific examples of PCR. In general, the reaction mixture is subjected to temperature cycles comprising a denaturation stage (typically 80-100° C.), an annealing stage with a temperature that is selected based on the melting temperature (Tm) of the primers and the degeneracy of the primers, and an extension stage (for example 40-75° C.). In real-time PCR analysis, additional reagents, methods, optical detection systems, and devices known in the art are used that allow a measurement of the magnitude of fluorescence in proportion to concentration of amplified template. In such analyses, incorporation of fluorescent dye into the amplified strands may be detected or measured.

Either primers or primers along with probes allow a quantification of the amount of specific template DNA present in the initial sample. In addition, RNA may be detected by PCR analysis by first creating a DNA template from RNA through a reverse transcriptase enzyme (i.e., the creation of cDNA). The marker expression may be detected by quantitative PCR analysis facilitating genotyping analysis of the samples.

"Amplification" is a special case of nucleic acid replication involving template specificity. Amplification may be a template-specific replication or a non-template-specific replication (i.e., replication may be specific template-dependent or not). Template specificity is here distinguished from fidelity of replication (synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out. The amplification process may result in the production of one or more amplicons.

The term "template" refers to nucleic acid originating from a sample that is analyzed for the presence of one or more markers. In contrast, "background template" or "control" is used in reference to nucleic acid other than sample template that may or may not be present in a sample. Background template is most often inadvertent. It may be the result of carryover, or it may be due to the presence of nucleic acid contaminants sought to be purified out of the sample. For example, nucleic acids from organisms other than those to be detected may be present as background in a test sample.

In addition to primers and probes, template specificity is also achieved in some amplification techniques by the choice of enzyme. Amplification enzymes are enzymes that, under the conditions in which they are used, will process only specific sequences of nucleic acid in a heterogeneous mixture of nucleic acid. Other nucleic acid sequences will not be replicated by this amplification enzyme. Similarly, in the case of T7 RNA polymerase, this amplification enzyme has a stringent specificity for its own promoters (Chamberlin et al. (1970) Nature (228):227). In the case of T4 DNA ligase, the enzyme will not ligate the two oligonucleotides or polynucleotides, where there is a mismatch between the oligonucleotide or polynucleotide substrate and the template at the ligation junction (Wu and Wallace (1989) Genomics (4):560). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.) (1989) PCR Technology, Stockton Press).

The term "amplifiable nucleic acid" refers to nucleic acids that may be amplified by any amplification method. It is contemplated that "amplifiable nucleic acid" will usually comprise "sample template." The terms "PCR product," "PCR fragment," "amplification product," and "amplicon" refer to the resultant mixture of compounds after two or more cycles of the PCR steps of denaturation, annealing and extension. These terms encompass the case where there has been amplification of one or more segments of one or more target sequences.

In some forms of PCR assays, quantification of a target in an unknown sample is often required. Such quantification may be determined in reference to the quantity of a control sample. The control sample starting material/template may be co-amplified in the same tube in a multiplex assay or may be amplified in a separate tube. Generally, the control sample contains template at a known concentration. The control sample template may be a plasmid construct comprising only one copy of the amplification region to be used as quantification reference. To calculate the quantity of a target in an unknown sample, various mathematical models are established. Calculations are based on the comparison of the distinct cycle determined by various methods, e.g., crossing points ($C_P$) and cycle threshold values ($C_t$) at a constant level of fluorescence; or $C_P$ acquisition according to established mathematic algorithm.

Some embodiments of the invention may comprise a multiplex assay. As used herein, the term "multiplex" refers to the production of more than one amplicon, PCR product, PCR fragment, amplification product, etc. in a single reaction vessel. In other words, multiplex is to be construed as the amplification of more than one marker-specific sequences within a PCR reaction or assay within the same PCR assay mixture (e.g., more than one amplicon is produced within a single vessel that contains all of the reagents necessary to perform a PCR reaction). In some embodiments, a step prior to performing the PCR (or RT-PCR, quantitative RT-PCR, etc.) reaction can occur such that sets of primers and/or primers and probes are designed, produced, and optimized within a given set of reaction conditions to ensure proper amplicon production during the performance of the PCR.

The algorithm for $C_t$ values in real time-PCR calculates the cycle at which each PCR amplification reaches a significant threshold. The calculated $C_t$ value is proportional to the number of marker copies present in the sample, and the $C_t$ value is a precise quantitative measurement of the copies of the marker found in any sample. In other words, $C_t$ values represent the presence of respective marker that the primer sets are designed to recognize. If the marker is missing in a sample, there should be no amplification in the Real Time-PCR reaction.

Alternatively, the $C_P$ value may be utilized. A $C_P$ value represents the cycle at which the increase of fluorescence is highest and where the logarithmic phase of a PCR begins. The LIGHTCYCLER® 480 Software calculates the second derivatives of entire amplification curves and determines where this value is at its maximum. By using the second-derivative algorithm, data obtained are more reliable and reproducible, even if fluorescence is relatively low.

The various and non-limiting embodiments of the PCR-based method detecting marker expression level as described herein may comprise one or more probes and/or primers. Generally, the probe or primer contains a sequence complementary to a sequence specific to a region of the nucleic acid of the marker gene. A sequence having less than 60% 70%, 80%, 90%, 95%, 99% or 100% identity to the identified gene sequence may also be used for probe or primer design if it is capable of binding to its complementary sequence of the desired target sequence in marker nucleic acid.

Some embodiments of the invention may include a method of comparing a marker in a sample relative to one or more control samples. A control may be any sample with a previously determined level of expression. A control may comprise material within the sample or material from sources other than the sample. Alternatively, the expression of a marker in a sample may be compared to a control that has a level of expression predetermined to signal or not signal a cellular or physiological characteristic. This level of expression may be derived from a single source of material including the sample itself or from a set of sources.

The sample in this method is preferably a biological sample from a subject. The term "sample" or "biological sample" is used in its broadest sense. Depending upon the embodiment of the invention, for example, a sample may comprise a bodily fluid including whole blood, serum, plasma, urine, saliva, cerebral spinal fluid, semen, vaginal fluid, pulmonary fluid, tears, perspiration, mucus and the like; an extract from a cell, chromosome, organelle, or membrane isolated from a cell; a cell; genomic DNA, RNA, or cDNA, in solution or bound to a substrate; a tissue; a tissue print, or any other material isolated in whole or in part from a living subject or organism. Biological samples may also include sections of tissues such as biopsy and autopsy samples, and frozen sections taken for histologic purposes such as blood, plasma, serum, sputum, stool, tears, mucus, hair, skin, and the like. Biological samples also include explants and primary and/or transformed cell cultures derived from patient tissues.

In some embodiments, sample or biological sample may include a bodily tissue, fluid, or any other specimen that may be obtained from a living organism that may comprise additional living organisms. By way of example only, in some embodiments, sample or biological sample may include a specimen from a first organism (e.g., a human) that may further comprise an additional organism (e.g., bacteria, including pathogenic or non-pathogenic/commensal bacteria, viruses, parasites, fungi, including pathogenic or non-pathogenic fungi, etc.). In some embodiments of the invention, the additional organism may be separately cultured after isolation of the sample to provide additional starting materials for downstream analyses. In some embodiments, the sample or biological sample may comprise a direct portion of the additional, non-human organism and the host organism (e.g., a biopsy or sputum sample that contains human cells and bacteria).

With respect to use of the sample or biological sample, embodiments of the claimed methodology provide improvements compared to conventional methodologies. Specifically, conventional methodologies of identifying and characterizing microorganisms include the need for morphological identification and culture growth. As such, conventional methodologies may take an extended period of time to identify the microorganism and may then require further time to identify whether the microorganism possesses and certain markers. Some embodiments of the invention can provide a user with information about any microorganisms and/or viruses present in a sample without the need for additional culturing because of the reliance of nucleic acid amplification and sequencing. In other words, direct extraction of nucleic acids coupled with amplification of the desired markers and downstream sequencing can reduce significantly the time required to obtain diagnostic and strain identifying information.

The invention may further comprise the step of sequencing the amplicon. Methods of sequencing include but need not be limited to any form of DNA sequencing including Sanger, next-generation sequencing, pyrosequencing, SOLiD sequencing, massively parallel sequencing, pooled, and barcoded DNA sequencing or any other sequencing method now known or yet to be disclosed.

In Sanger Sequencing, a single-stranded DNA template, a primer, a DNA polymerase, nucleotides and a label such as a radioactive label conjugated with the nucleotide base or a fluorescent label conjugated to the primer, and one chain terminator base comprising a dideoxynucleotide (ddATP, ddGTP, ddCTP, or ddTTP, are added to each of four reaction (one reaction for each of the chain terminator bases). The sequence may be determined by electrophoresis of the resulting strands. In dye terminator sequencing, each of the chain termination bases is labeled with a fluorescent label of a different wavelength that allows the sequencing to be performed in a single reaction.

In pyrosequencing, the addition of a base to a single-stranded template to be sequenced by a polymerase results in the release of a pyrophosphate upon nucleotide incorporation. An ATP sulfuryrlase enzyme converts pyrophosphate into ATP that in turn catalyzes the conversion of luciferin to oxyluciferin which results in the generation of visible light that is then detected by a camera or other sensor capable of capturing visible light.

In SOLiD sequencing, the molecule to be sequenced is fragmented and used to prepare a population of clonal magnetic beads (in which each bead is conjugated to a plurality of copies of a single fragment) with an adaptor sequence and alternatively a barcode sequence. The beads are bound to a glass surface. Sequencing is then performed through 2-base encoding.

In massively parallel sequencing, randomly fragmented targeted nucleic acids and/or amplicons are attached to a surface. The fragments/amplicons are extended and bridge amplified to create a flow cell with clusters, each with a plurality of copies of a single fragment sequence. The templates are sequenced by synthesizing the fragments in parallel. Bases are indicated by the release of a fluorescent dye correlating to the addition of the particular base to the fragment.

Nucleic acid sequences may be identified by the IUAPC letter code which is as follows: A—Adenine base; C—Cytosine base; G—guanine base; T or U—thymine or uracil base; I—inosine base. M—A or C; R-A or G; W-A or T; S-C or G; Y-C or T; K-G or T; V-A or C or G; H-A or C or T; D-A or G or T; B-C or G or T; N or X-A or C or G or T. Note that T or U may be used interchangeably depending on whether the nucleic acid is DNA or RNA. A sequence having less than 60%, 70%, 80%, 90%, 95%, 99% or 100% identity to the identifying sequence may still be encompassed by the invention if it is able of binding to its complimentary sequence and/or facilitating nucleic acid amplification of a desired target sequence. In some embodiments, as previously mentioned, the method may include the use of massively parallel sequencing, as detailed in U.S. Pat. Nos. 8,431,348 and 7,754,429, which are hereby incorporated by reference in their entirety.

Some embodiments of the invention comprise multiple steps and/or processes that are carried out to execute the universal tail indexing strategy to prepare amplicons corresponding to desired markers for sequencing. In some embodiments, one or more makers for a given sample or template can be selected, as described above. Some embodiments of the invention can be used in conjunction with an analysis of one or more markers (e.g., genes/alleles) associated with a particular phenotype (e.g., virulence).

After selection of the markers, marker-specific primers/oligonucleotides can be designed for the amplification of the markers to produce the desired amplicons, as detailed above. As is known in the art, a forward and a reverse marker-specific primer can be designed to amplify the marker from a nucleic acid sample. In some embodiments, the forward and reverse primers can be designed to produce an amplicon (e.g., some or all of the sequence of the marker) of a desired length. For example, the length of the amplicon may comprise approximately 50 base pairs (bp), 100 bp, 150 bp, 200 bp, 250 bp, 300 bp, 350 bp, 400 bp, 450 bp, 500 bp, 1,000 bp, or any size amplicon greater in size or therebetween.

As previously mentioned, some embodiments of the invention may include a multiplex PCR reaction. For example, marker-specific primers can be designed for multiple markers or multiple regions of the same marker such that multiple amplicons of between about 50 bp and 1,000 bp are being produced within a single PCR reaction vessel. In other words, the forward and reverse primers can be designed to function within a given set of temperature parameters such that more than one amplicon can be successfully amplified from a given template within a single PCR reaction mixture. As such, multiple amplicons can be prepared using the universal tail indexing strategy for sequencing preparation.

In some embodiments, the forward and reverse primers that have been designed for each of the markers can be modified to include a universal tail. For example, the universal tail sequences can be relatively or completely unique sequences of nucleotides that are coupled to the 5' ends of some or all of the forward and reverse marker-specific primers. In some aspects, the universal tail sequences can be selected such that there is little to no overlap in sequence between portions of the markers that are being amplified and the universal tail sequences. Moreover, the universal tail sequences can comprise a length between ten and twenty nucleotides in length. In some embodiments, the universal tail sequences can be any other length, as desired by the user to meet the needs and requirements of the reaction. As such, the universal tail sequences can exhibit a relatively negligible impact on binding of the forward and reverse marker-specific primers to the template sequence to enable amplification. Moreover, as a result of being included on the 5' end of the forward and reverse marker-specific primers, the universal tail sequences will form a portion of the resulting amplicons. In addition, in some aspects of the invention, the sequences selected for the universal tail sequences can be at least partially correlated with the chemical composition of the template nucleic acids. For example, in some aspects, the sequences selected for the universal tail sequences can be at least partially correlated with the G-C content of the organism from which the template is isolated.

In some aspects, some or all of the universal tail sequences can be at least partially unique. In some embodiments, each of the 5' ends of all of the forward marker-specific primers within a given PCR assay mixture can comprise the same or a similar universal tail sequence (e.g., a first universal tail sequence or UT1). Similarly, each of the 5' ends of all of the reverse marker-specific primers within the same PCR assay mixture can comprise a second universal tail sequence (UT2) that differs from the first universal tail sequence. As such, each respective sample from which a template sequence is used in the multiplex PCR assay will have two unique universal tail sequences. Accordingly, each forward and reverse marker-specific primer within a multiplex PCR mixture will include a unique universal tail sequence. For example, if the PCR includes 35 different samples, 35 universal tail sequences can be employed for the forward primers in each of the 35 unique reactions (i.e., not including technical replicates) and 35 universal tail sequences can be employed for the reverse primers in each of the 35 unique reactions (i.e., not including technical replicates). Overall, the forward and reverse marker-specific primers that each comprise the universal tail sequences can comprise a generally short length (e.g., 25-50 bp), which can facilitate simultaneous amplification of multiple targets in a single reaction.

In addition, some embodiments of the invention may comprise performing quantitative PCR to optimize the multiplex PCR assay. For example, after design of the forward and reverse marker-specific primers that each include a universal tail sequence, the contemplated multiplex PCR assays can be performed using quantitative PCR (e.g., using DNA as a template) to assess relative quantities of the amplicons produced. Accordingly, the sequence coverage of each amplicon is considered to be equal if the quantities of the amplicons produced by the multiplex quantitative PCR appear to be equal. If the quantities of the amplicons produced by the multiplex quantitative PCR do not appear to be equal, the forward and/or reverse marker-specific primers can be altered and re-optimized until adequate quantities of amplicons are produced.

After design and adequate optimization of the multiplex PCR assay comprising multiple forward and reverse marker-specific primers that each includes universal tail sequences, the multiplex PCR can be performed to obtain the amplicons associated with the above-described markers. In some embodiments, template that has been previously isolated from a sample can be used for the amplification of the amplicons. In some aspects, multiple PCR reaction replicates can be performed for each sample template and one or more control templates.

In some embodiments, after successful production of the amplicons during the multiplex PCR assay, the resulting amplicons can be further processed to provide sequencing-ready amplicons. For example, some embodiments of the invention may comprise an indexing extension step. In some aspects, the indexing extension step may comprise extending the optimized multiplex amplicons using a set of indexing and common primers that recognize the respective universal tail sequences used for the particular group of amplicons in a minimal cycle PCR assay (e.g., 5-10 total cycles). In particular, each multiplex set of amplicons to be sequenced can be extended with a different set of index oligonucleotides and common oligonucleotides that recognize UT1 and UT2, respectively. In some aspects, the index sequence of the index oligonucleotides can be custom designed to allow for the selection of an index sequence from potentially thousands of different index sequences.

After this step, the resulting products include a set of amplicons for each sample/template that comprise the same index and any necessary sequences that may be required for a particular sequencing platform (e.g., platform sequences associated with the ILLUMINA® Next Generation sequencing platform). Thereafter, the resulting extension-reaction products can be quantified, pooled, and sequenced using a desired platform. In some aspects, the inclusion of the universal tail sequences on the index and common primers can coincide with the use of genomic and index read primers in the mixture of sequencing primer reagents. For example, some embodiments of the invention are capable of pooling multiple amplicons with multiple indices in a single sequencing run to provide 40,000×-95,000× coverage across the amplicons. In other embodiments, the systems and methods associated with the invention can be configured to provide any level of sequencing coverage that is desirable to the user (e.g., higher or lower that the coverage levels discussed above). In some embodiments, after sequencing and generation of the sequence data, the resulting data can be demultiplexed and the sequence files can be aligned to the appropriate references sequences for subsequent sequence analyses.

Embodiments of the invention offer additional advantages relative to conventional systems. For example, some embodiments of the invention comprise the use of PCR before sequencing such that only limited amounts of starting material are necessary and the starting material need not be of high quality (e.g., genomic DNA, crude DNA extracts, single stranded DNA, RNA, cDNA, etc.). In contrast, many conventional sample preparation systems may require relatively large amounts of starting material of relatively high quality, which can limit the use of these systems. Moreover, the inclusion of non-desirable template materials can also interfere in one or more downstream processes in conventional systems and methods. For example, if an investigation is being conducted that focuses on one or more organisms that may be associated with another organism (e.g., bacteria associated with a human); the sampling of the target organism may result in template contamination from the host organism.

In particular, in some aspects, obtaining samples of pathogenic or commensal bacteria from, on, or within a human may also result in the collection of human tissue. As such, when isolating the template, human nucleic acids may contaminate the bacterial template. Some embodiments of the invention are configured such that the contaminating template (e.g., from a human) would not interfere with downstream processes, including sequencing. For example, some embodiments of the invention operate such that only a limited amount of starting template (e.g., 500 femtograms or greater) can be used. Moreover, some embodiments are also configured such that the starting material (e.g., template contaminated with foreign nucleic acids) can still produce the required amplicons for sequencing in the presence of more than a 1,000-fold excess of contaminating template with no discernible inhibition of the multiplex PCR.

In certain aspects, the present invention provides an assay that works with as little as about 1 pg, about 900 fg, about 800 fg, about 700 fg, about 600 fg, about 500 fg, about 400 fg, about 300 fg, about 200 fg, or about 100 fg of genomic DNA.

The following examples are given for purely illustrative and non-limiting purposes of the present invention.

EXAMPLES

Example 1

Multiplex Assays for LymeSeq Lyme Disease Next-Generation Sequencing Diagnostic Assay In one aspect, the LymeSeq Lyme Disease Next-Generation Sequencing Diagnostic Assay involves the steps of DNA or RNA extraction, amplification and library preparation, next-generation sequencing (NGS sequencing), reference mapping, and clinical interpretation as shown in FIG. 1. Amplification and library preparation can be efficiently carried out with multiplex assays of various configurations.

In one aspect, the LymeSeq Lyme Disease Next-Generation Sequencing Diagnostic Assay comprises the configuration of multiplex assays with the following primers identified in Table 1 without universal tails and in Table 2 and Table 3 with universal tails.

Multiplex 1 assays: 16S-1_UT, 16S-2_UT, 16S-3_UT, 16S-4_UT. 16S-5_UT, Ana-msp2_UT1, bbk32_UT, dbpA_UT, dbpB_UT, Ehrl-16S_UT, Ehrl-sodB UT, EV-D68 UT, flaB UT1, flaB UT2, Ft-G UT, glpQ_UT1, IGS-5S-23S-TK_UT, IGS1-Bunikis_UT1, IGS2-Derdakova_UT, ospA-Rudenko_UT, ospB_UT1, ospB_UT2, ospC-Bunikis_UT1, ospD_UT1, p66_UT1, parA_UT1, Yp3a_UT, Yppla_UT, H3N2_UT, Bart-ssrA_UT1, Babe-18S_UT1, IPC-gapDH_UT1, and Sa_M4_UT1.

When this configuration of the multiplex assays is used, an amplification reaction mixture is prepared. After the amplification reactions are complete next-generation sequencing is carried out to determine the sequences of the amplicons. The sequences may be analyzed with reference mapping and further analyzed to arrive at a clinical interpretation.

Figure 2:
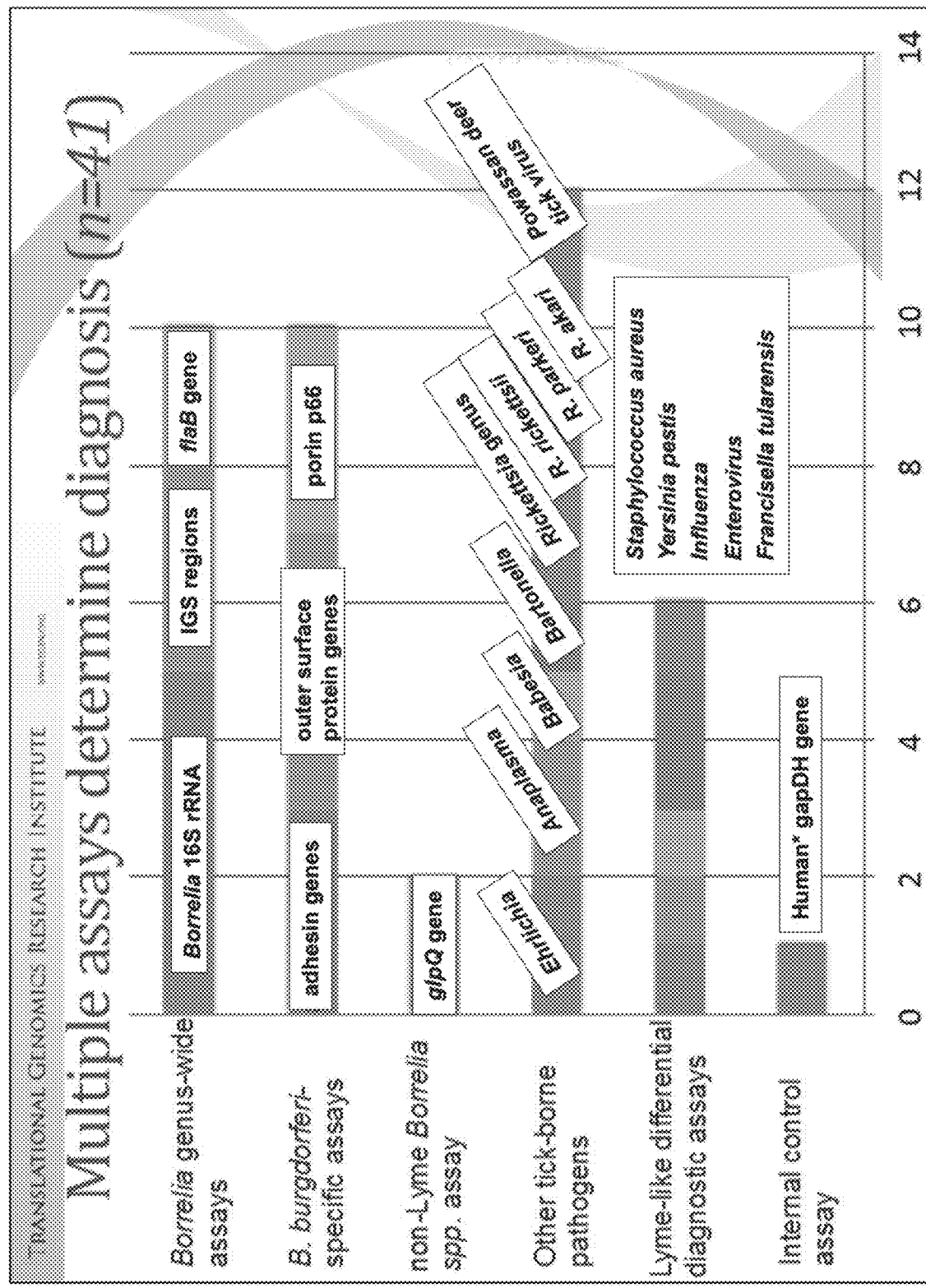
FIG. 2 depicts a configuration of multiplex assays used with the LymeSeq Lyme Disease Next-Generation Sequencing Diagnostic Assay to rapidly and accurately diagnose Lyme Disease.

As shown in FIG. 2, the configuration of Multiplex 1 assays includes:

1) *Borrelia* genus-wide assays targeting the *Borrelia* 16S rRNA, the 16S-23S intergenic spacer (IGS), and the flaB gene (flagella subunit B);

2) *Borrelia burgdorferi* sensu lato-specific assays targeting the adhesin genes (e.g., bbk32, dbpA, and dbpB) outer surface protein genes (e.g. ospA, ospB, and ospC), and p66 porin genes;

3) a non-Lyme *Borrelia* spp. assay targeting the glpQ gene;

4) assays specific to other tick-borne pathogens including *Erlichia* spp., *Anaplasma phagocytophilum*, *Babesia* spp., *Bartonella* spp., Powassan and deer tick viruses, and *Rickettsia* spp.;

5) Lyme-like differential diagnostic assays specific to *Staphylococcus aureus*, *Yersinia pestis*, *Influenza* virus, Enterovirus, and *Francisella tularensis*; and 6) an internal control assay targeting the human GAPDH gene.

Figure 3:
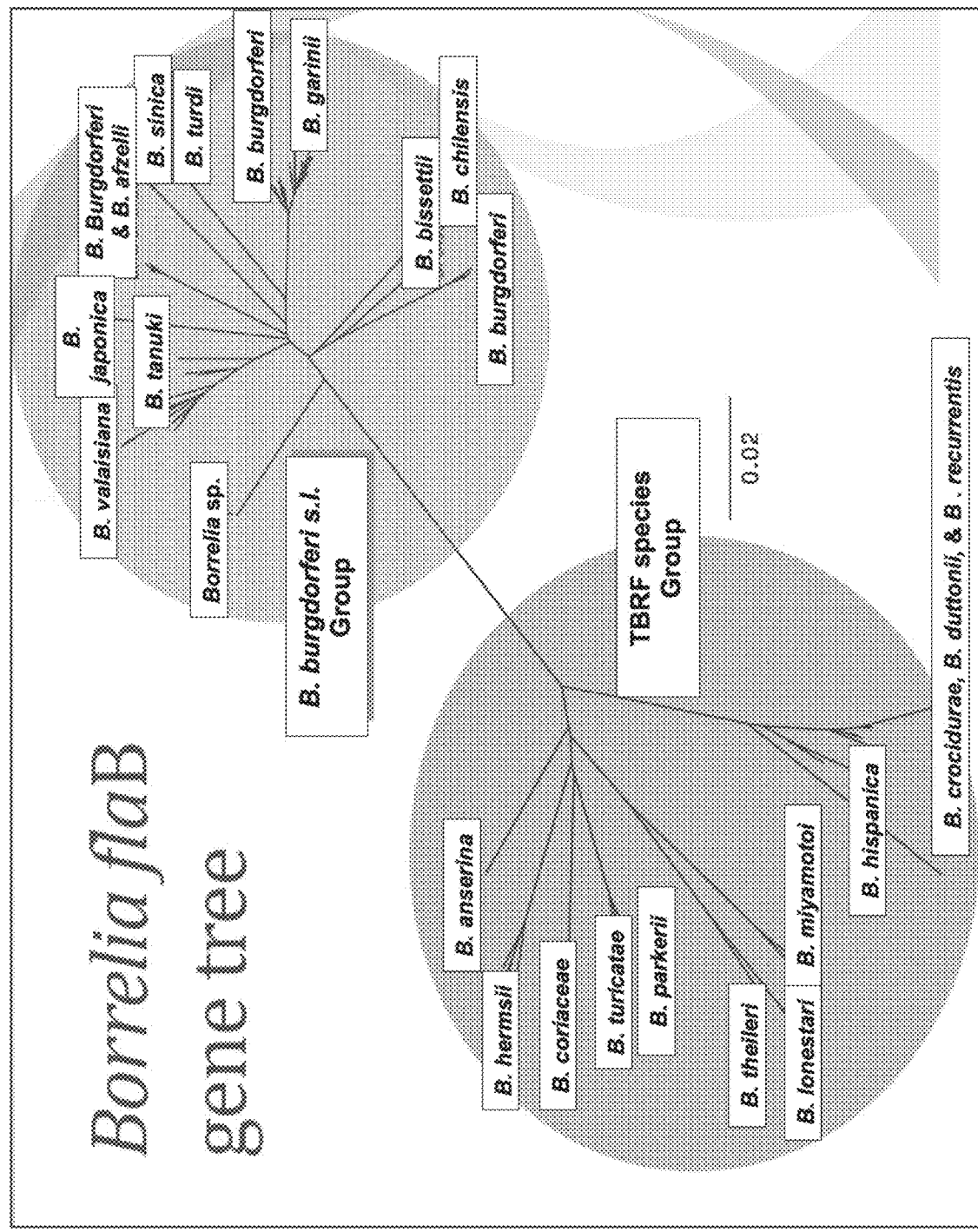
FIG. 3 depicts the *Borrelia* flaB gene tree with the *Borrelia* species in the *Borrelia burdorferi* sensu lato group clustering together and the *Borrelia* species in the tick-borne relapsing fever (TBRF) species group clustering together.
Figure 4:
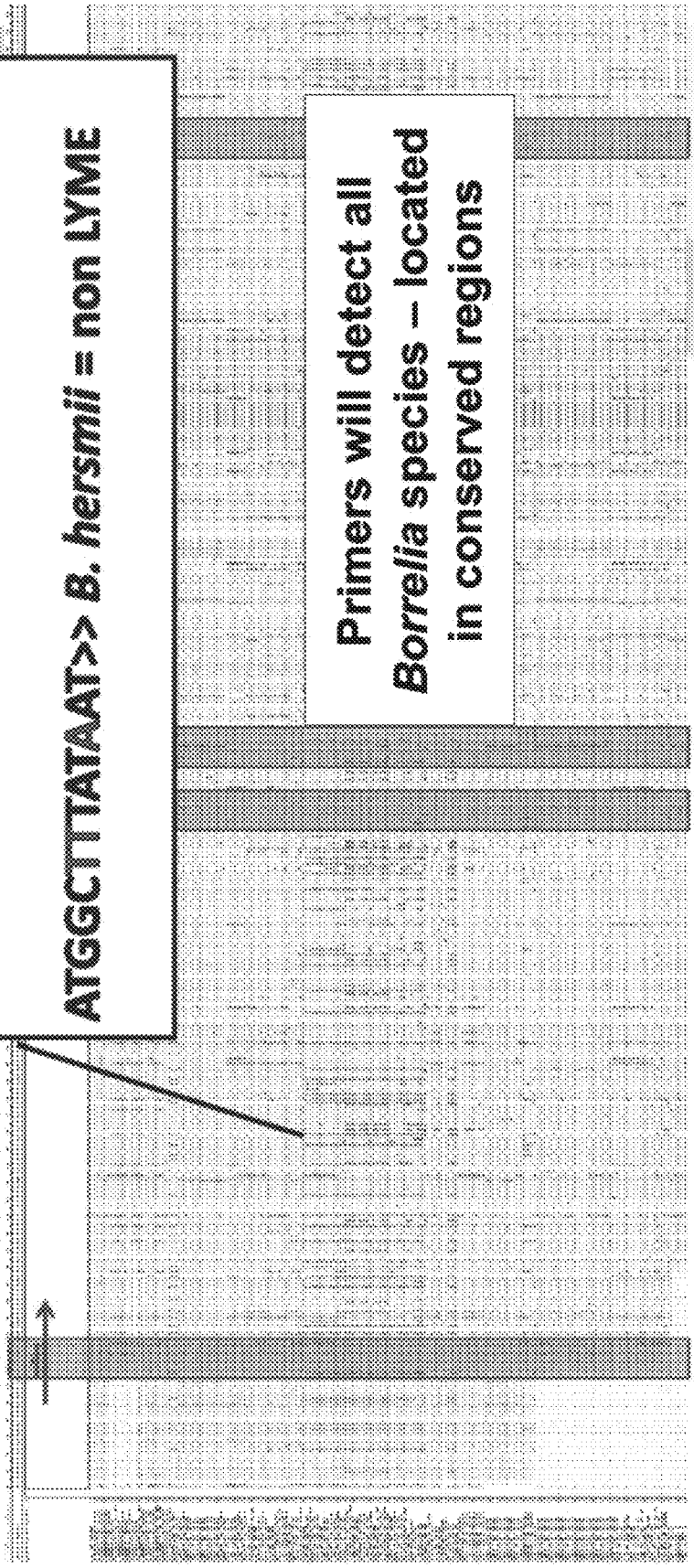
FIG. 4 depicts mapping of flaB sequence reads against 482 unique DNA sequences to identify *Borrelia* species that cause Lyme Disease and *Borrelia* species that do not cause Lyme Disease. For example, the sequence ATGGCCCTAT-CAT (SEQ ID NO: 476) is specific to *Borrelia burdorferi* while the sequence ATGGCTTTATAAT (SEQ ID NO: 477) is specific to *Borrelia hersmii*.
Figure 5:
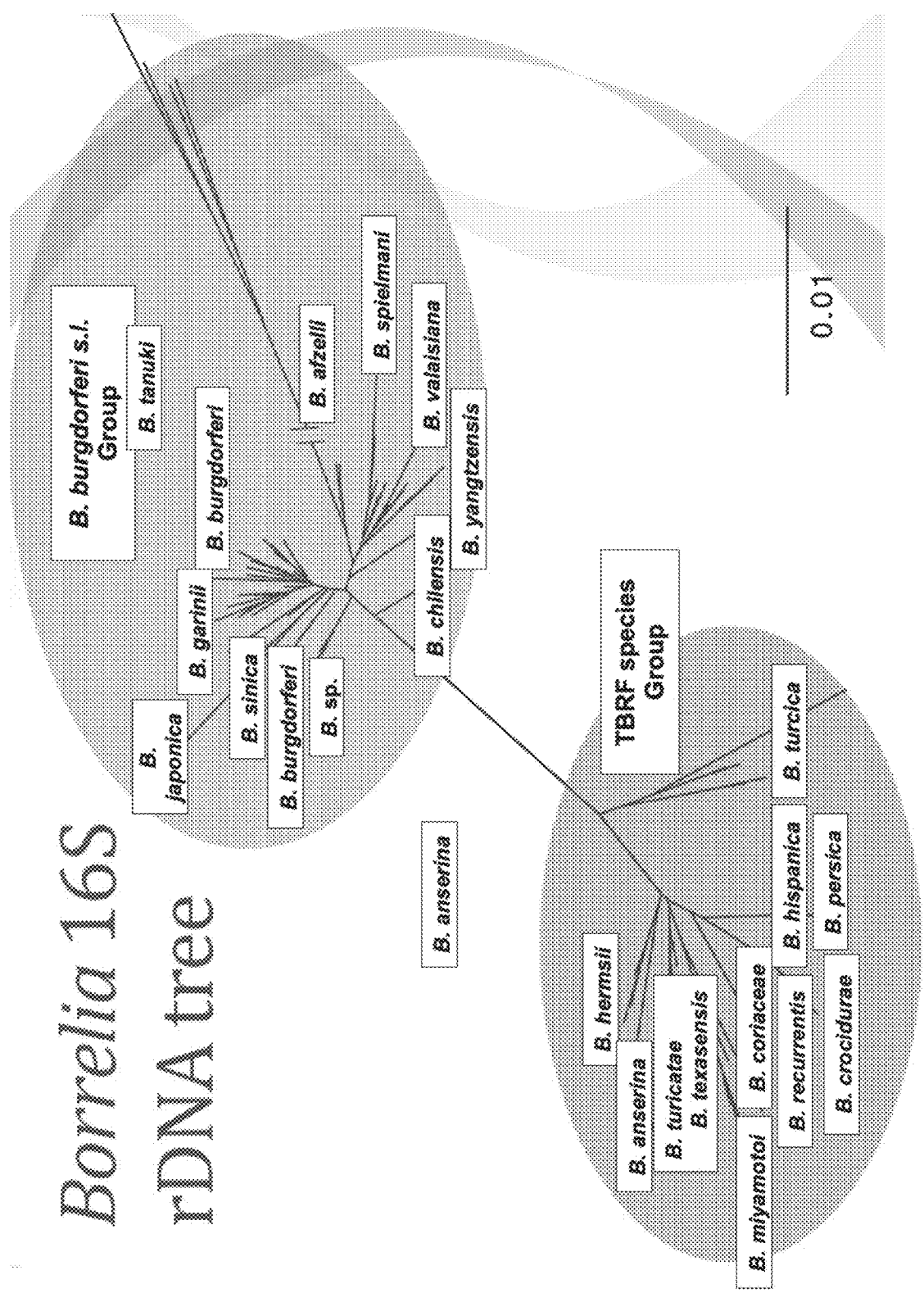
FIG. 5 depicts the *Borrelia* 16S rDNA tree with the *Borrelia* species in the *Borrelia burdorferi* sensu lato group clustering together and the *Borrelia* species in the tick-borne relapsing fever (TBRF) species group clustering together.

The amplification and sequencing of regions of the flaB gene allows for the differentiation of the tick-borne relapsing fever (TBRF) species group from the *Borrelia burgdorferi* sensu lato group as shown in FIG. 3. The primers of the multiplex assays are designed to detect all *Borrelia* species and are located in conserved regions. Comparison of the sequenced amplicons from a sample are compared to an alignment of 482 known unique flaB gene DNA sequences to determine the presence or absence of particular *Borrelia* species that contribute to disease states such as Lyme disease and relapsing fever (see FIG. 4). Similarly, sequencing of amplicons from five assays covering the majority of the gene sequence of the *Borrelia* 16S rDNA and comparison of the sequences detected in a sample to an alignment of 185 known unique DNA sequences facilitates detection of *Borrelia* species in the TBRF species group and in the *Borrelia burgdorferi* sensu lato (Lyme) group (see FIG. 5 and FIG. 6).

Example 2

Sensitivity Results with LymeSeq Lyme Disease Next-Generation Sequencing Diagnostic Assay Eight strains of *Borrelia burgdorferi* sensu lato were serially diluted and the DNA extracted from each diluted strain. After amplification using primers from Table 3 and next-generation sequencing the results showed that each strain was properly identified and the number of sequence reads mapping to the 16S rRNA reference correlated with the dilution factor of each sample.

Example 3

Detection of *Borrelia* Species in DNA Extracted from *Ixodes pacificus*

Seventy-four Western black-legged tick (*Ixodes pacificus*) samples were collected form the San Francisco Bay area and the DNA of each sample was extracted and analyzed as described in Example 1 with the following primers from Table 2:

16S_UT, IGS2-5S-23S-TK_UT, IGS1-Bunikis_UT1, bbk32_UT, dbpA_UT, dbpB_UT, flaB_UT1, flaB_UT2, glpQ_UT1, ospA-Rudenko_UT, ospB_UT2, ospC-Bunikis_UT1, ospD_UT1, p66_UT1, parA_UT1, IPC-gapDH_UT1, Ana-msp2_UT1, Ehrl-16S_UT, Ehrl-sodB_UT, EV-D68_UT, Ft-G_UT, Yp3a_UT, Yppla_UT, H3N2_UT, Bart-ssrA_UT1, Babe-18S_UT1, Sa_M4_UT1.

After the amplicons were sequenced and analyzed with the LymeSeq Lyme Disease Next-Generation Sequencing Diagnostic Assay twenty-seven samples were found to contain genomic DNA from *Borrelia burgdorferi* sensu law, eight samples contains genomic DNA from *B. miyamotoi*, one sample contained genomic DNA from *Bartonella* spp., and one sample contained genomic DNA from *Anaplasma phagocytophilum*.

Example 4

Investigation of Tick-Borne Relapsing Fever Outbreak with LymeSeq Lyme Disease Next-Generation Sequencing Diagnostic Assay

*Borrelia hermsii* is one of the species causing tick-borne relapsing fever (TBRF) in infected patients. An outbreak of TBRF was investigated in Northern Arizona (see Jones, J M et al., "Tick-Borne Relapsing Fever Outbreak among a High School Football Team at an Outdoor Education Camping trip, Arizona, 2014," *Am. J. Trop. Med. Hyg.* 95(3), 2016, pp. 546-550). Blood was collected from several patients who were febrile after recent tick exposure. Eight blood samples were analyzed with the LymeSeq Lyme Disease Next-Generation Sequencing Diagnostic Assay as described in Example 1, and the assay indicated that seven of the eight were positive for *Borrelia hermsii*. TBRF was confirmed in several of these patients by spirochetemia detection on blood smear and/or by culturing blood samples from the patients and isolating *Borrelia hermsii*.

Example 5

Figure 7:
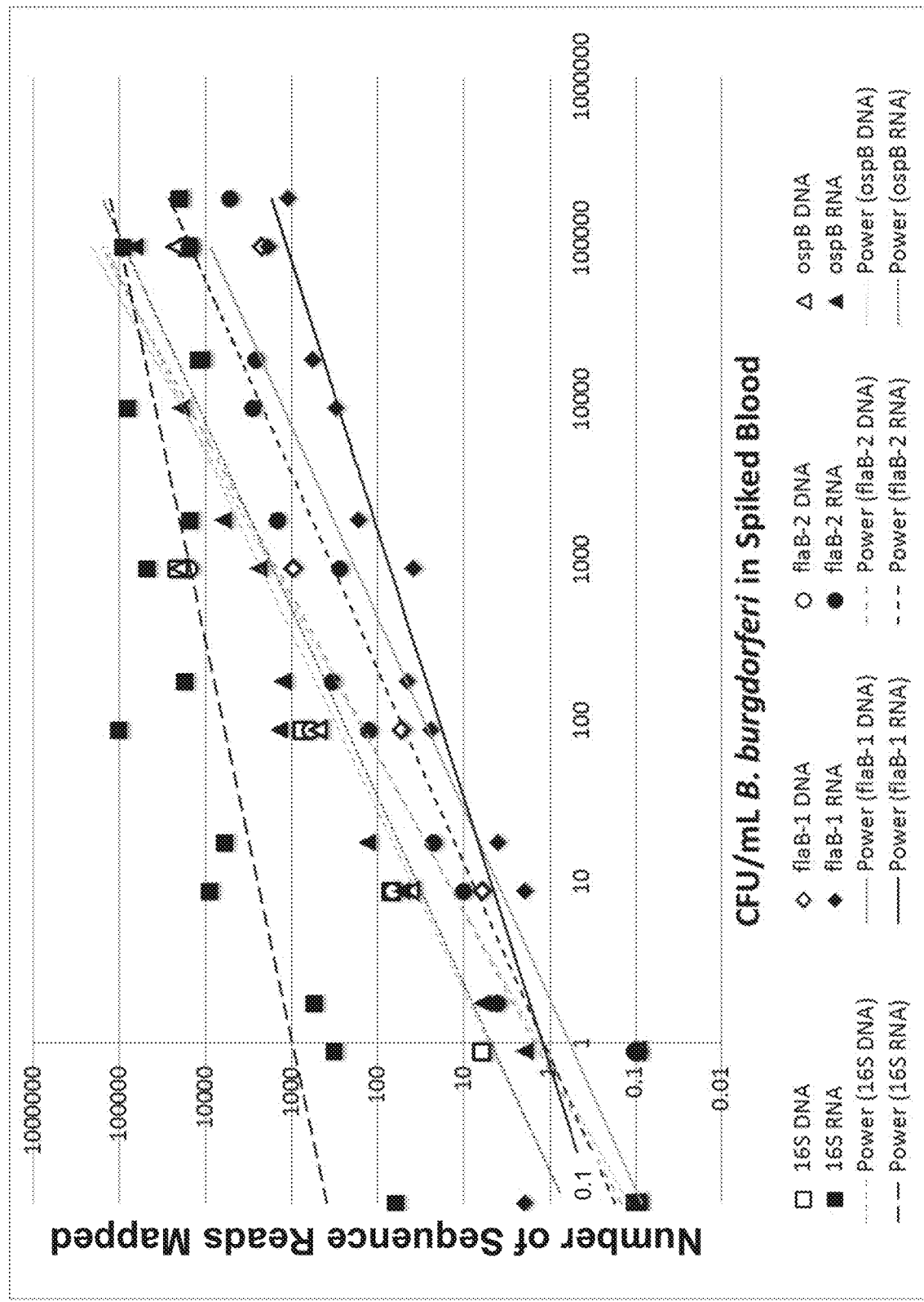
FIG. 7 depicts colony forming units (CFU) of *Borrelia burgdorferi* in spiked blood samples plotted against the number of sequence reads for 16S rRNA, flaB-1, flaB-2, and ospB after analysis of either extracted RNA or extracted DNA from the samples. Trendlines are indicated with solid or dashed lines.

Analysis of DNA Versus RNA with Lymeseq Lyme Disease Next-Generation Sequencing Diagnostic Assay in Spiked Blood Samples and TBRF Outbreak Blood Samples Blood samples were spiked with *Borrelia burgdorferi* and subsequently analyzed with the LymeSeq Lyme Disease Next-Generation Sequencing Diagnostic Assay. Amplicon sequencing allows for analysis of extracted RNA as well as DNA. Both DNA and RNA were extracted from the spiked blood samples and analyzed as described in Example 1. The colony forming units (CFU) of *Borrelia burgdorferi* were counted in each spiked blood sample and plotted against the number of sequence reads for 16S rRNA, flaB-1, flaB-2, and ospB from each sample of extracted RNA or DNA (see FIG. 7). The results showed evidence of 16S rRNA in blood at a relatively high level even when very few *Borrelia burgdorferi* CFUs were present suggesting that extraction and analysis of RNA samples increased the sensitivity of the LymeSeq Lyme Disease Next-Generation Sequencing Diagnostic Assay as compared to extraction and analysis of DNA samples.

In another experiment, eight blood samples known to contain *Borrelia hermsii* were analyzed with the LymeSeq Lyme Disease Next-Generation Sequencing Diagnostic Assay. DNA and RNA from each sample were analyzed. The assay confirmed the presence of *Borrelia hermsii* in all eight samples. In addition, the sequence reads from the extracted RNA samples were generally greater than those from the corresponding extracted DNA samples. For instance, in one example the extracted DNA produced only 200 sequence reads while the corresponding extracted RNA produced 200,000 sequence reads. These results confirmed the enhanced sensitivity of the assay when used to analyze RNA samples.

Unless defined otherwise, all technical and scientific terms herein have the same meaning as commonly understood by one of ordinary skill in the art to which this invention belongs. All publications, patents, and patent publications cited are incorporated by reference herein in their entirety for all purposes.

It is understood that the disclosed invention is not limited to the particular methodology, protocols and materials described as these can vary. It is also understood that the terminology used herein is for the purposes of describing particular embodiments only and is not intended to limit the scope of the present invention which will be limited only by the appended claims.

Those skilled in the art will recognize, or be able to ascertain using no more than routine experimentation, many equivalents to the specific embodiments of the invention described herein. Such equivalents are intended to be encompassed by the following claims.

TABLE 1

Universal tail targets and assays for LymeSeq Lyme Disease Next-Generation Sequencing Diagnostic Assay. The primers listed do not include the universal tails (UT).

| Target Purpose | Target Taxon | Target Gene/ Region | UT Assay Type | Assay | Primer | Sequence without UT | SEQ ID NO: |
|---|---|---|---|---|---|---|---|
| Species ID | Borrelia spp. | 16S-set of 5 assays to cover whole gene | Sequence-based | 16S-1_UT | 16S-1_UT_F | CGGGTGAGTAAC GCGTGGAT | 1 |
| | | | Also good RNA target | | 16S-1_UT_R | CCTCTCAGGCCG GTTACTTATC | 2 |
| | | | | 16S-2_UT | 16S-2_UT_F | CGGTCACACTGG AACTGAGA | 3 |
| | | | | | 16S-2_UT_R | GCTGCTGGCACG TAATTAGC | 4 |
| | | | | 16S-3_UT | 16S-3_UT_F | GCGAGCGTTGTTC GGGAT | 5 |
| | | | | | 16S-3_UT_R | ACTCAGCGTCAG TCTTGACC | 6 |
| | | | | 16S-4_UT | 16S-4_UT_F | CGCTGTAAACGA TGCACACTTG | 7 |
| | | | | | 16S-4_UT_R | ACAACCATGCAG CACCTGTA | 8 |
| | | | | 16S-5_UT | 16S-5_UT_F | GCAACGAGCGCA ACCCTT | 9 |
| | | | | | 16S-5_UT_R | TACAAGGCCCGA GAACGTATTCAC | 10 |
| Species ID | Borrelia spp. | IGS2 5S-23S | Sequence-based | IGS2-5S-23S-TK_UT | IGS-5S-23S-TK_UT_F | GAGTTCGCGGGA GAGTAGGTTATT GCC | 11 |
| | | rrfA-rrlB | Also good RNA target | | IGS-5S-23S-TK_UT_R | TCAGGGTACTTA GATGKTTCACTTC C | 12 |

TABLE 1-continued

Universal tail targets and assays for LymeSeq Lyme Disease Next-Generation Sequencing Diagnostic Assay. The primers listed do not include the universal tails (UT).

| Target Purpose | Target Taxon | Target Gene/ Region | UT Assay Type | Assay | Primer | Sequence without UT | SEQ ID NO: |
|---|---|---|---|---|---|---|---|
| | | | | IGS2-5S-23S-Postic_UT | IGS-5S-23S-Postic_UT_F | CTGCGAGTTCGC GGGAGA | 13 |
| | | | | | IGS-5S-23S-Postic_UT_R | TCCTAGGCATTCA CCATA | 14 |
| | | | | IGS2-Derdakova_UT | IGS2-Derdakova_UT_F | CGACCTTCTTCGC CTTAAAGC | 15 |
| | | | | | IGS2-Derdakova_UT_R | AGCTCTTATTCGC TGATGGTA | 16 |
| | | | | IGS1-Bunikis_UT1 | IGS1-Bunikis_UT1_F | GTATGTTTAGTGA GGGGGGTG | 17 |
| | | | | | IGS1-Bunikis_UT1_R | GGATCATAGCTC AGGTGGTTAG | 18 |
| | | | | IGS1-Bunikis_UT2 | IGS1-Bunikis_UT2_F | AGGGGGGTGAAG TCGTAACAAG | 19 |
| | | | | | IGS1-Bunikis_UT2_R | GTCTGATAAACCT GAGGTCGA | 20 |
| Species ID | Borrelia spp. | IGS1 | Sequence-based | | | | |
| | | rrs-rrlA | Also good RNA target | rrs-rrlA_UT1 | rrs-rrlA_UT1_F1 | GGGGTTCGAGTCC CTYAACCT | 219 |
| Species ID | Borrelia spp. | IGS rrs-rrlA 16S-23S IGS | | | rrs-rrlA_UT1_F2 | TTGGTTTAGAGCA TCGGCTTTGC | 220 |
| | | | | | rrs-rrlA_UT1_R1 | CCTTGCACTTTAG CGAAACAAC | 221 |
| | | | | | rrs-rrlA_UT1_R2 | CCTTGTGCTTTAG TGAAACAAC | 222 |
| | | | | | rrs-rrlA_UT1_R3 | ACTTGCCATACGT AAACACCGT | 223 |
| | | | | | rrs-rrlA_UT1_R4 | CTCATGACTTGTC ACACGTAAACAA C | 224 |

TABLE 1-continued

Universal tail targets and assays for LymeSeq Lyme Disease Next-Generation Sequencing Diagnostic Assay. The primers listed do not include the universal tails (UT).

| Target Purpose | Target Taxon | Target Gene/ Region | UT Assay Type | Assay | Primer | Sequence without UT | SEQ ID NO: |
|---|---|---|---|---|---|---|---|
| | | | | | rrs-rrlA_UT1_R5 | GTTCAACTCCTCC TGGTCCCAA | 225 |
| | | | | | rrs-rrlA_UT1_R6 | ATCCTATAGATGC AATCTCTGWCC | 226 |
| | | | | | rrs-rrlA_UT1_R7 | TTTGCATGTAATC AAGTCTTGGAATT C | 227 |
| | | | | | rrs-rrlA_UT1_R8 | TACTTTCACCTCT AGACATTCTTGT | 228 |
| | | | | | rrs-rrlA_UT1_R9 | TAGGTTGATTCAT GATCAGGTCCTT | 229 |
| | | | | | rrs-rrlA_UT1_R10 | CGATTCGGTCAC GGCTCTTAC | 230 |
| | | | | | rrs-rrlA_UT1_R11 | CCTTATGATTTAG TAACAACGTA AGT | 231 |
| | | | | | rrs-rrlA_UT1_R12 | AAGCTAGTAATG AATGTGGGATGT T | 232 |
| Species ID | Borrelia spp. | flaB | Sequence-based | flaB_UT1 | flaB_UT1_F | GCWTCTGATGAT GCTGCTGGIA | 21 |
| | | | | | flaB_UT1_R1 | GCATTCCAAGYT CTTCAGCTGT | 22 |
| | | | | | flaB_UT1_R2 | GCATTCCAAGCTC TTCAGCWGT | 23 |
| | | | | flaB_UT2 | flaB_UT2_F1 | ACACCAGCRTCR CTTTCAGG | 24 |
| | | | | | flaB_UT2_F2 | ACACCAGCATCA YTAKCTGGA | 25 |
| | | | | | flaB_UT2_F3 | ACACCAGCATCA TTRGCTGGA | 26 |

TABLE 1-continued

Universal tail targets and assays for LymeSeq Lyme Disease Next-Generation Sequencing Diagnostic Assay. The primers listed do not include the universal tails (UT).

| Target Purpose | Target Taxon | Target Gene/ Region | UT Assay Type | Assay | Primer | Sequence without UT | SEQ ID NO: |
|---|---|---|---|---|---|---|---|
| | | | | | flaB_UT2_R1 | TTGGAAAGCACC TAAATTTGCYCTT | 27 |
| | | | | | flaB_UT2_R2 | TTGRAAAGCACC AAGATTTGCTCTT | 28 |
| | | | | | flaB_UT2_R3 | TTGGAAAGCACC YAAATTTGCTCTT | 29 |
| Species ID | non-Burgdorferi Borrelia spp. | glpQ | Sequence-based | glpQ_UT1 | glpQ_UT1_F1 | CCAGAACATACC TTAGAAKCTAAA GC | 30 |
| | | | | | glpQ_UT1_F2 | CAGAACATACAT TAGAAGCCAAAG C | 31 |
| | | | | | glpQ_UT1_R1 | CCTTGTTGYTTAT GCCATAAKGGTT | 32 |
| | | | | | glpQ_UT1_R2 | CCTTGTTGTTTAT GCCAHAAGGGTT | 33 |
| | | | | glpQ-Halp_UT2 | glpQ-Halp_UT2_F1 | CCAGAACATACC TTAGAAKCTAAA GC | 34 |
| | | | | | glpQ-Halp_UT2_F2 | CAGAACATACAT TAGAAGCCAAAG C | 35 |
| | | | | | glpQ-Halp_UT2_R1 | CACATTAGCAGA AATCAAATCAC | 36 |
| | | | | | glpQ-Halp_UT2_R2 | GATCAAATCTTTC GCTAAGRCTTAG TG | 37 |
| | | | | | glpQ-Halp_UT2_R3 | GATCAAATCTTTC ACTGAGACTTAG TG | 38 |

TABLE 1-continued

Universal tail targets and assays for LymeSeq Lyme Disease Next-Generation Sequencing Diagnostic Assay. The primers listed do not include the universal tails (UT).

| Target Purpose | Target Taxon | Target Gene/ Region | Assay | UT Assay Type | Primer | Sequence without UT | SEQ ID NO: |
|---|---|---|---|---|---|---|---|
| | | | | | glpQ-Halp_UT2_R4 | GATCAAATCTTTC ACTAAGCTTAA TG | 39 |
| | | | | | glpQ-Halp_UT2_R5 | GGGTATCCARGG TCCAAT | 40 |
| Species ID | B. burgdorferi sensu stricto | bbk32 | bbk32_UT | presence/absence | bbk32_UT_F1 | TGGAGGAGMCTA TTGAAAGYAATG | 41 |
| | | | | Also good RNA target | bbk32_UT_F2 | TGAAGGAKACTA TTGAAAGYAATG | 42 |
| | | | | | bbk32_UT_R1 | GCGTGTAGAATA CATTTGGGTTAGC | 43 |
| | | | | | bbk32_UT_R2 | GACGTGTAGAAT ACATTTGGGTTTG C | 44 |
| Species ID | B. burgdorferi | dbpA | dbpA_UT | presence/absence | dbpA_UT_F | AACAATGTAAAT TTTGCTGCCTTT | 45 |
| | | | | Also good RNA target | dbpA_UT_R | CCTGAGACCTCA AGCATCAT | 46 |
| Species ID | B. burgdorferi | dbpB | dbpB_UT | presence/absence | dbpB_UT_F | CGGTTCCAAGGT AACAAGTG | 47 |
| | | | | Also good RNA target | dbpB_UT_R | TAATCCAATACTA CATCGACCAAT A | 48 |
| Species ID | B. burgdorferi | dbpA | dbpA_UT2 | presence/absence | dbpA_UT2_F1 | CAGCCGCATCTGT AACTG | 233 |
| | | | | | dbpA_UT2_F2 | TCAGTTCCATTG AAACTG | 234 |
| | | | | | dbpA_UT2_F3 | TTYAGCYGCATCT GAGAC | 235 |
| | | | | | dbpA_UT2_F4 | TTCAGCTGCCWT TGAGAC | 236 |

TABLE 1-continued

Universal tail targets and assays for LymeSeq Lyme Disease Next-Generation Sequencing Diagnostic Assay. The primers listed do not include the universal tails (UT).

| Target Purpose | Target Taxon | Target Gene/ Region | UT Assay Type | Assay | Primer | Sequence without UT | SEQ ID NO: |
|---|---|---|---|---|---|---|---|
| | | | | | dbpA_UT2_R1 | CAGGYAGCAAGG TATCAGA | 237 |
| | | | | | dbpA_UT2_R2 | CRGGTAGYGGGG TATCAGA | 238 |
| | | | | | dbpA_UT2_R3 | AACAGGTRGAAAA GGYAGCA | 239 |
| | | | | | dbpB_UT2_F1 | CGCAAGCAATCT TTCAGYTGTGT | 240 |
| Species ID | B. burgdorferi | dbpB | presence/absence | dbpB_UT2 | dbpB_UT2_F2 | CTCAACCAATCTT TCAGCYGTGT | 241 |
| | | | | | dbpB_UT2_F3 | CTTCAAGCAATCT TTCACATGTGT | 242 |
| | | | | | dbpB_UT2_F4 | CCTCAATTAATCT TTCAGATGTGCT | 243 |
| | | | | | dbpB_UT2_F5 | TTCAAGCAATCTT TCGGCTGTGT | 244 |
| | | | | | dbpB_UT2_F6 | CTCCATTACTCTT TCGGCTGTGT | 245 |
| | | | | | dbpB_UT2_R1 | RYAGCKCCTTGAA TCRTCYTYTAAGG | 246 |
| | | | | | dbpB_UT2_R2 | AAGCAATGCTTG AATCSTMTTCTGA | 247 |
| | | | | | dbpB_UT2_R3 | AGCAAAGCTTG AATCGTCTTCC | 248 |
| Species ID | Anaplasma phagocyto- philum | msp2 (major surface protein) | presence/absence | Ana-msp2_UT1 | Ana- msp2_UT1_F | AGTTTGACTGGA ACACWCCTGATC | 49 |
| | | AY151054 | | | Ana- msp2_UT1_R | CTCGTAACCAATC TCAAGCTCAAC | 50 |

TABLE 1-continued

Universal tail targets and assays for LymeSeq Lyme Disease Next-Generation Sequencing Diagnostic Assay. The primers listed do not include the universal tails (UT).

| Target Purpose | Target Taxon | Target Gene/ Region | UT Assay Type | Assay | Primer | Sequence without UT | SEQ ID NO: |
|---|---|---|---|---|---|---|---|
| Species ID | Anaplasma phagocyto- philum | msp2 (major surface protein) | presence/absence | Ana-msp2_UT2 | Ana- msp2_UT2_F | GGGAGAGTAACG GAGARACWAAG G | 51 |
| | | | | | Ana- msp2_UT2_R1 | CTGGCACCACCA ATACCATAACC | 52 |
| | | | | | Ana- msp2_UT2_R2 | CTGGCACCACCA ATACCRTACC | 53 |
| | | | | | Ana- msp2_UT2_F | GGGAGAGTAACG GAGARACWAAG G | 54 |
| | | | | | Ana- msp2_UT1_R | CTCCTAACCAATC TCAAGCTCAAC | 55 |
| Species ID | Ehrlichia genus | 16S | presence indicates genus present | Ehrl-16S_UT | Ehrl-16S_UT_F | GAGGATTTTATCT TTGTATTGTAGCT AAC | 56 |
| | | | sequence tells species | | Ehrl-16S_UT_R | TGTAAGGTCCAG CCGAACTGACT | 57 |
| Species ID | Ehrlichia genus | sodB | presence/absence | Ehrl-sodB_UT | Ehrl- sodB_UT_F | TTTAATAATGCTG GTCAAGTATGGA ATCAT | 58 |
| | | | sequence-based to tell species | | Ehrl- sodB_UT_R | AAGCRTGYTCCC ATACATCCATAG | 59 |
| Species ID | B. burgdorferi | ospB | presence/absence | ospB_UT_1 | ospB_UT_F1 | TGCCGTGACAGA AGACTC | 60 |
| | | | | | ospB_UT_R1 | CAGCAGAAACTG TTAATTTTACTTT ACTC | 61 |
| | | | presence/absence | ospB_UT_2 | ospB_UT_F2 | TGCCGTGACAGA AGACTC | 62 |
| | | | | | ospB_UT_R2 | AATCAGCAGAAA CTGTTAATTTTAC TTTAC | 63 |

TABLE 1-continued

Universal tail targets and assays for LymeSeq Lyme Disease Next-Generation Sequencing Diagnostic Assay. The primers listed do not include the universal tails (UT).

| Target Purpose | Target Taxon | Target Gene/ Region | UT Assay Type | Assay | Primer | Sequence without UT | SEQ ID NO: |
|---|---|---|---|---|---|---|---|
| Species ID | B. burgdorferi | ospB | presence/absence | ospB_UT3 | ospB_UT3_F1 | GTYGAACTTAAA GGAACTTCCGAT | 249 |
| | | | | | ospB_UT3_F2 | NTTGAGCTWAAA GGAACWTCTGAT | 250 |
| | | | | | ospB_UT3_F3 | GTTGAGCTTAAA GGRGTTKCTGA | 251 |
| | | | | | ospB_UT3_F4 | GGTGAGCTTAAA GGGGATTTTGA | 252 |
| | | | | | ospB_UT3_F5 | GTTGAGCTTAAA GGCCTTTCTGAG | 253 |
| | | | | | ospB_UT3_R1 | CCGMCTMCAAGA CTTCCTTCA | 254 |
| | | | | | ospB_UT3_R2 | CCGCCTACAAGA TTTCCTGGA | 255 |
| | | | | | ospB_UT3_R3 | CCACCAACAAGA CTTCCTTCTAGT | 256 |
| | | | | | ospB_UT3_R4 | CCACCAACTAGA CTTCCTTAAAC | 257 |
| | | | | | ospB_UT3_R5 | CCACCAACAAGA TTTCCTTCGAAC | 258 |
| | | | | | ospB_UT3_R6 | CATTAGCTACTTT TCCTTCAAGAG | 259 |
| | | | | | ospB_UT3_R7 | CATTAGCTAGAG TTCCTTCAAGAG | 260 |
| | | | | | ospB_UT3_R8 | TCAGCAGYTAGA GTTCCTTCAAGA | 261 |
| Species ID | B. burgdorferi | ospC-TG | presence/absence | ospC-TG_UT1 | ospC-TG_UT1_F | TCAGGRAAAGAT GGGAATRCATCT GC | 262 |
| | | | | | ospC-TG_UT1_R | GRCTTGTAAGCTC TTTAACTGMATT AG | 263 |

TABLE 1-continued

Universal tail targets and assays for LymeSeq Lyme Disease Next-Generation Sequencing Diagnostic Assay. The primers listed do not include the universal tails (UT).

| Target Purpose | Target Taxon | Target Gene/ Region | UT Assay Type | Assay | Primer | Sequence without UT | SEQ ID NO: |
|---|---|---|---|---|---|---|---|
| Species ID | B. burgdorferi | p66 | presence/absence | p66_UT3 | p66_UT3_F1 | GCCYATGACYGG ATTCAAA | 264 |
| | | | | | p66_UT3_F2 | TTYGCACCTATGA CTGGRTTT | 265 |
| | | | | | p66_UT3_R | GGYTTCCATGTTG CTTGAAY | 266 |
| | | | | p66_UT4 | p66_UT4_F1 | TGARGCTATCCAT CCAAGRCC | 267 |
| | | | | | p66_UT4_F2 | GAAGCTGTCCAT CCAAGATTAG | 268 |
| | | | | | p66_UT4_R1 | CGGTTTAGCTTGG AATACAGATGA | 269 |
| | | | | | p66_UT4_R2 | CGGTTTGCCTGG AATAAAGATGA | 270 |
| | | | | | p66_UT4_R3 | GGCYTAGCTTGG AAYATAGATGA | 271 |
| | | | | p66_UT5 | p66_UT5_F | GCAATMGAAAY TCAACATTC | 272 |
| | | | | | p66_UT5_R | CRCTTGCAAATG GGTCTATTCCT | 273 |
| Species ID | B. burgdorferi | ospA | ospA | ospA_UT1 | ospA_UT1_F1 | GGITCTGGAAYAC TTGAAGG | 274 |
| | | | | | ospA_UT1_F2 | GGATCTGGRRTRC TTGAAGG | 275 |
| | | | | | ospA_UT1_F3 | GGTTCTGGAASCC TTGARGG | 276 |
| | | | | | ospA_UT1_F4 | GGRYCTGGGGTR CTTGAAGG | 277 |
| | | | | | ospA_UT1_F5 | GGATCTGGGGGA AAGCTGAAG | 278 |

TABLE 1-continued

Universal tail targets and assays for LymeSeq Lyme Disease Next-Generation Sequencing Diagnostic Assay. The primers listed do not include the universal tails (UT).

| Target Purpose | Target Taxon | Target Gene/ Region | UT Assay Type | Assay | Primer | Sequence without UT | SEQ ID NO: |
|---|---|---|---|---|---|---|---|
| | | | | | ospA_UT1_F6 | GGTTCTGGDGTRCTKGAAGG | 279 |
| | | | | | ospA_UT1_F7 | GGATCTGGMWHGCYYGAAGG | 280 |
| | | | | | ospA_UT1_F8 | GGMGCTGGAMAWCTTGAAGG | 281 |
| | | | | | ospA_UT1_R1 | CAAGTYTGKTKCCRTTTKCTCTTG | 282 |
| | | | | | ospA_UT1_R2 | CAAGYYTGTWCCGYYTGCTCTTR | 283 |
| | | | | | ospA_UT1_R3 | CMAGTGTAGTYCCGYTTGDTCTTG | 284 |
| | | | | | ospA_UT1_R4 | CAAGTMTKGWWCCRTTTGCTCTTR | 285 |
| | | | | | ospA_UT1_R5 | CAAGKGTAGTTTCGTTTKCTCTTG | 286 |
| | | | | | ospA_UT1_R6 | CAAKTGTAGTATYRTTTGATCTTG | 287 |
| | | | | | ospA_UT1_R7 | CAAGMKTRGTKCCGTTTGCTCTTG | 288 |
| | | | | | ospA_UT1_R8 | CAAGTCTGGTTCCGTCTTTCTTG | 289 |
| | | | | | ospA_UT1_R9 | CAAGTGGTGTTCCGTTTGTTCTTG | 290 |
| | | | | | ospA_UT1_R10 | CAAGTCTATTTCCATTTGCTCTTG | 291 |
| | | | | | ospA_UT1_R11 | CAAGTCTGGTTCCGTTAYCTCTTA | 292 |
| | | | | | ospA_UT1_R12 | CAAGTCTGGTTCCATTTGCCCTTA | 293 |

TABLE 1-continued

Universal tail targets and assays for LymeSeq Lyme Disease Next-Generation Sequencing Diagnostic Assay. The primers listed do not include the universal tails (UT).

| Target Purpose | Target Taxon | Target Gene/Region | UT Assay Type | Assay | Primer | Sequence without UT | SEQ ID NO: |
|---|---|---|---|---|---|---|---|
| Species ID | B. burgdorferi | ospC | presence/absence | ospC-Bunikis_UT1 | ospC-Bunikis_UT1_F | ATGAAAAAGAAT ACATTAAGTGC | 64 |
| Also typing info | | | and sequence-based | | ospC-Bunikis_UT1_R | ATTAATCTTATAA TATTGATTTTAAT TAAGG | 65 |
| | | | presence/absence | ospC-Bunikis_UT2 | ospC-Bunikis_UT2_F | TATTAATGACTTT ATTTTATTTATA TCT | 66 |
| | | | and sequence-based | | ospC-Bunikis_UT2_R | TTGATTTTAATTA AGGTTTTTTTGG | 67 |
| | | | presence/absence | ospC-Wang_UT1 | ospC-Wang_UT1_F | AAAGAATACATT AAGTGCGATATT | 68 |
| | | | and sequence-based | | ospC-Wang_UT1_R | GGGCTTGTAAGC TCTTTAACT | 69 |
| Species ID | B. burgdorferi | p66 | presence/absence | p66-Bunikis_UT1 | p66-Bunikis_UT1_F | GATTTTTCTATAT TTGGACACAT | 70 |
| | | | Also good RNA target | | p66-Bunikis_UT1_R | TGTAAATCTTATT AGTTTTTCAAG | 71 |
| | | | presence/absence | p66-Bunikis_UT2 | p66-Bunikis_UT2_F | CAAAAAAGAAAC ACCCTCAGATCC | 72 |
| | | | Also good RNA target | | p66-Bunikis_UT2_R | CCTGTTTTAAAT AAATTTTGTAGC ATC | 73 |
| | | | presence/absence | p66-Rudenko_UT1 | p66-Rudenko_UT1_F | CGAAGATACTAA ATCTGT | 74 |
| | | | Also good RNA target | | p66-Rudenko_UT1_R | GCTGCTTTTGAGA TGTGTCC | 75 |
| Species ID | B. burgdorferi | ospA | presence/absence | ospA-Rudenko_UT | ospA-Rudenko_UT_F | GAGCTTAAGGA ACTTCTGATAA | 76 |
| | | | | | ospA-Rudenko_UT_R | GTATTGTTGTACT GTAATTGT | 77 |

TABLE 1-continued

Universal tail targets and assays for LymeSeq Lyme Disease Next-Generation Sequencing Diagnostic Assay. The primers listed do not include the universal tails (UT).

| Target Purpose | Target Taxon | Target Gene/ Region | UT Assay Type | Assay | Primer | Sequence without UT | SEQ ID NO: |
|---|---|---|---|---|---|---|---|
| Differential diagnostic | Enterovirus strain D68 | VP1 | presence/absence | EV-D68_UT | EV-D68_UT_F1 | ACCAGARGAAGC CATACAAAC | 78 |
| | | | | | EV-D68_UT_F2 | TGACACTTCAAG CAATGTTCGTA | 79 |
| | | | | | EV-D68_UT_F3 | AACGCCGAACTT GGTGTG | 80 |
| | | | | | EV-D68_UT_F4 | AACACCGAACCA GAGGAAG | 81 |
| | | | | | EV-D68_UT_R1 | SCTGAYTGCCART GGAATGAA | 82 |
| | | | | | EV-D68_UT_R2 | ATGTGCTGTTATT GCTACCTACTG | 83 |
| | | | | | EV-D68_UT_R3 | ATTATTACTACTA CCATTCACTGCTA CA | 84 |
| | | | | | EV-D68_UT_R4 | TCAAATCCAGCA AAGCCATCA | 85 |
| | | | | | EV-D68_UT_R5 | AGAATACACTAG CATTACTACCTGA CT | 86 |
| Differential diagnostics | Staphylococcus aureus | | | Sa_M4_UT2 | Sa_M4_UT2_F | TAGCCTTGTGTATT AAGTGGTTGT | 87 |
| | | | | | Sa_M4_UT2_R | GTCATAGCATAG TTCGGGTCA | 88 |
| Differential diagnostics | Influenza | matrix gene | presence/absence | H3N2_UT | H3N_UT_F | AAGACCAATYCT GTCACCTCTGA | 89 |
| | | | RNA target | | H3N2_UT_R | CAAAGCGTCTAC GCTGCAGTCC | 90 |

TABLE 1-continued

Universal tail targets and assays for LymeSeq Lyme Disease Next-Generation Sequencing Diagnostic Assay. The primers listed do not include the universal tails (UT).

| Target Purpose | Target Taxon | Target Gene/Region | UT Assay Type | Assay | Primer | Sequence without UT | SEQ ID NO: |
|---|---|---|---|---|---|---|---|
| Differential diagnostics | Yersinia pestis | plasmid | | Yppla_UT | Yppla_UT_F | GAAAGGAGTGCG GGTAATAGTT | 91 |
| | | | | | Yppla_UT_R | GGCCTGCAAGTC CAATATATGG | 92 |
| | | chromosome | | Yp3a_UT | Yp3a_UT_F | CATTGGACGGCA TCACGAT | 93 |
| | | | | | Yp3a_UT_R | AGTTGGCCAGCG ATTCGA | 94 |
| Differential diagnostics | Francisella tularensis | | SNP | Ft-G_UT | Ft-G_UT_F | CTAAGCCATAAG CCCTTTCTCTAAC TTGT | 95 |
| | | | | | Ft-G_UT_R | AGCAATGACAAA GCTTGTTGAAAA AG | 96 |
| Species ID | Borrelia burgdorferi | porin gene | presence/absence | p66-borrelia_UT1 | p66_UT1_F | GTAATTGCAGAA ACACCTTTTGAAT | 97 |
| | | | | | p66_UT1_R | CTGCTTTTGAGAT GTGTCCAA | 98 |
| | | | presence/absence | p66-borrelia_UT2 | p66_UT2_F | TGTAATTGCAGA AACACCTTTTGA | 99 |
| | | | | | p66_UT2_R | GCTGCTTTTGAGA TGTGTCC | 100 |
| Species ID | | outer surface protein D | presence/absence | ospD-borrelia_UT1 | ospD_UT1_F | ATCAWMTGAGG CAAATAAAGTTG TAGA | 101 |
| | | | | | ospD_UT1_R | TGTTCTGCYGCTT TAGTAAGG | 102 |

TABLE 1-continued

Universal tail targets and assays for LymeSeq Lyme Disease Next-Generation Sequencing Diagnostic Assay. The primers listed do not include the universal tails (UT).

| Target Purpose | Target Taxon | Target Gene/ Region | UT Assay Type | Assay | Primer | Sequence without UT | SEQ ID NO: |
|---|---|---|---|---|---|---|---|
| Species ID | Borrelia burgdorferi | partitioning gene | presence/absence | parA_UT1 | parA_UT1_F | TTRACTTCTTCTA TYGCATCCATTA | 103 |
| | | | | | parA_UT1_R | TRTTCCTTCTCAT CCAATTCTATGT | 104 |
| Genus ID | Bartonella | ssrA | presence/absence | Bart-ssrA_UT1 | Bart-ssrA_UT1_F | GGCTAAATIAGTA GTTGCAAAYGAC A | 105 |
| | | | | | Bart-ssrA_UT1_R | GCTTCTGTTGCCA GGTG | 106 |
| Genus ID | Babesia | 18S | sequence-based | Babe-18S_UT1 | Babe-18S_UT1_F | ACCGTCCAAAGC TGATAGGTC | 107 |
| | | | | | Babe-18S_UT1_R | CGAAACTGCGAA TGGCTCATTA | 108 |
| Genus ID | Rickettsia | ompA | presence/absence | Rkttsia-ompA_UT1 | Rkttsia-ompA_UT1_F | GGCATTACTTAC RGTGSTGAT | 294 |
| | | | | | Rkttsia-ompA_UT1_R | CCATGATTTGCAG CAAYAGCAT | 295 |
| | | | | Rkttsia-ompA_UT2 | Rkttsia-ompA_UT2_F | CGYTAGCTGGGC TTAGRTATTC | 296 |
| | | | | | Rkttsia-ompA_UT2_R | CGCCGRAACTTTA TTCTTGAATG | 297 |
| | | | | Rkttsia-ompA_UT3 | Rkttsia-ompA_UT3_F | ACTTAYGGTGGT GATTATAYTATC | 298 |
| | | | | | Rkttsia-ompA_UT3_R | TGCAGCAACAGC ATTAKTACYG | 299 |
| | | | | Rkttsia-ompA_UT4 | Rkttsia-ompA_UT4_F1 | GCTGRAGGAGTA GCTAATGGT | 300 |
| | | | | | Rkttsia-ompA_UT4_F2 | GCAGCAGGAGTA GCTGATGAT | 301 |
| | | | | | Rkttsia-ompA_UT4_R | MCGCAGCAGTAC CGGTTAAAG | 302 |

TABLE 1-continued

Universal tail targets and assays for LymeSeq Lyme Disease Next-Generation Sequencing Diagnostic Assay. The primers listed do not include the universal tails (UT).

| Target Purpose | Target Taxon | Target Gene/ Region | UT Assay Type | Assay | Primer | Sequence without UT | SEQ ID NO: |
|---|---|---|---|---|---|---|---|
| | | | | | Rkttsia-ompA_UT5_F | CAACCGCAGCRW TAATGCTAAC | 303 |
| | | | | | Rkttsia-ompA_UT5_R | CCTCCCGTATCTA CCACTGAAC | 304 |
| | | | | Rkttsia-ompA_UT6 | Rkttsia-ompA_UT6_F | TGCAGGAGCAGA TAATGGTA | 305 |
| | | | | | Rkttsia-ompA_UT6_R | GCCCGCAGTAAT AGTAACAG | 306 |
| | | | | Rkttsia-ompA_UT7 | Rkttsia-ompA_UT7_F1 | GGTGCAAGCCAA GTAACATATAC | 307 |
| | | | | | Rkttsia-ompA_UT7_F2 | AGTACAAATCA AGTAACATATAC | 308 |
| | | | | | Rkttsia-ompA_UT7_R1 | AAACCGCCTTCC GTTTCTG | 309 |
| | | | | | Rkttsia-ompA_UT7_R2 | AATCCACCTGCC GCTTCTG | 310 |
| Genus ID | Powassan and deer tick viruses | | presence/absence | Powass_UT | Powass_UT_F1 | GGCDGTAGGYCA TGTTTATGAC | 311 |
| | | | | | Powass_UT_F2 | AGTGTGGGCCA CGTCTATGAC | 312 |
| | | | | | Powass_UT_R1 | CCGAAGGCAGGT GATCTTTG | 313 |
| | | | | | Powass_UT_R2 | CAGAAGGCAGGT GGTCCTTG | 314 |
| Internal control | Human | gapDH | presence/absence | IPC-gapDH_UT1 | IPC-gapDH_UT1_F | CCTGCCAAATAT GATGACATCAAG | 109 |
| | | | | | IPC-gapDH_UT1_R | GTGGTCGTTGAG GGCAATG | 110 |

TABLE 2

Primers for LymeSeq Lyme Disease Next-Generation Sequencing Diagnostic Assay with the universal tail targets. ACCCAACTGAATGGAGC (SEQ ID NO: 217) or ACGCACTTGACTTGTCTTC (SEQ ID NO: 218).

| Primer | Sequence with Universal Tail Target | SEQ ID NO: |
|---|---|---|
| 16S-1_UT_F | ACCCAACTGAATGGAGCCGGGTGAGTAACGCGTGGAT | 111 |
| 16S-1_UT_R | ACGCACTTGACTTGTCTTCCCTCTCAGGCCGGTTACTTATC | 112 |
| 16S-2_UT_F | ACCCAACTGAATGGAGCCGGTCACACTGGAACTGAGA | 113 |
| 16S-2_UT_R | ACGCACTTGACTTGTCTTCGCTGCTGGCACGTAATTAGC | 114 |
| 16S-3_UT_F | ACCCAACTGAATGGAGCGCGAGCGTTGTTCGGGAT | 115 |
| 16S-3_UT_R | ACGCACTTGACTTGTCTTCACTCAGCGTCAGTCTTGACC | 116 |
| 16S-4_UT_F | ACCCAACTGAATGGAGCCGCTGTAAACGATGCACACTTG | 117 |
| 16S-4_UT_R | ACGCACTTGACTTGTCTTCACAACCATGCAGCACCTGTA | 118 |
| 16S-5_UT_F | ACCCAACTGAATGGAGCGCAACGAGCGCAACCCTT | 119 |
| 16S-5_UT_R | ACGCACTTGACTTGTCTTCTACAAGGCCCGAGAACGTATTCAC | 120 |
| Ana-msp2_UT1_F | ACCCAACTGAATGGAGCAGTTTGACTGGAACACWCCTGATC | 121 |
| Ana-msp2_UT1_R | ACGCACTTGACTTGTCTTCCTCGTAACCAATCTCAAGCTCAAC | 122 |
| Ana-msp2_UT2_F | ACCCAACTGAATGGAGCGGGAGAGTAACGGAGARACWAAGG | 123 |
| Ana-msp2_UT2_R1 | ACGCACTTGACTTGTCTTCCTGGCACCACCAATACCATAACC | 124 |
| Ana-msp2_UT2_R2 | ACGCACTTGACTTGTCTTCCTGGCACCACCAATACCRTACC | 125 |
| Babe-18S_UT1_F | ACCCAACTGAATGGAGCACCGTCCAAAGCTGATAGGTC | 126 |
| Babe-18S_UT1_R | ACGCACTTGACTTGTCTTCCGAAACTGCGAATGGCTCATTA | 127 |
| Bart-ssrA_UT1_F | ACCCAACTGAATGGAGCGGCTAAATIAGTAGTTGCAAAYGACA | 128 |
| Bart-ssrA_UT1_R | ACGCACTTGACTTGTCTTCGCTTCTGTTGCCAGGTG | 129 |
| bbk32_UT_F1 | ACCCAACTGAATGGAGCTGGAGGAGMCTATTGAAAGYAATG | 130 |
| bbk32_UT_F2 | ACCCAACTGAATGGAGCTGAAGGAKACTATTGAAAGYAATG | 131 |
| bbk32_UT_R1 | ACGCACTTGACTTGTCTTCGCGTGTAGAATACATTTGGGTTAGC | 132 |
| bbk32_UT_R2 | ACGCACTTGACTTGTCTTCGACGTGTAGAATACATTTGGGTTTGC | 133 |
| dbpA_UT_F | ACCCAACTGAATGGAGCAACAATGTAAATTTTGCTGCCTTT | 134 |
| dbpA_UT_R | ACGCACTTGACTTGTCTTCCCTGAGACCTCAAGCATCAT | 135 |
| dbpB_UT_F | ACCCAACTGAATGGAGCCGGTTCCAAGGTAACAAGTG | 136 |
| dbpB_UT_R | ACGCACTTGACTTGTCTTCTAATCCAATACTACATGCGACCAATA | 137 |
| Ehrl-16S_UT_F | ACCCAACTGAATGGAGCGAGGATTTTATCTTTGTATTGTAGCTAAC | 138 |
| Ehrl-16S_UT_R | ACGCACTTGACTTGTCTTCTGTAAGGTCCAGCCGAACTGACT | 139 |
| Ehrl-sodB_UT_F | ACCCAACTGAATGGAGCTTTAATAATGCTGGTCAAGTATGGAATCAT | 140 |
| Ehrl-sodB_UT_R | ACGCACTTGACTTGTCTTCAAGCRTGYTCCCATACATCCATAG | 141 |
| EV-D68_UT_F1 | ACCCAACTGAATGGAGCACCAGARGAAGCCATACAAAC | 142 |
| EV-D68_UT_F2 | ACCCAACTGAATGGAGCTGACACTTCAAGCAATGTTCGTA | 143 |
| EV-D68_UT_F3 | ACCCAACTGAATGGAGCAACGCCGAACTTGGTGTG | 144 |
| EV-D68_UT_F4 | ACCCAACTGAATGGAGCAACACCGAACCAGAGGAAG | 145 |
| EV-D68_UT_R1 | ACGCACTTGACTTGTCTTCSCTGAYTGCCARTGGAATGAA | 146 |
| EV-D68_UT_R2 | ACGCACTTGACTTGTCTTCATGTGCTGTTATTGCTACCTACTG | 147 |

TABLE 2-continued

Primers for LymeSeq Lyme Disease Next-Generation Sequencing Diagnostic Assay with the universal tail targets. ACCCAACTGAATGGAGC (SEQ ID NO: 217) or ACGCACTTGACTTGTCTTC (SEQ ID NO: 218).

| Primer | Sequence with Universal Tail Target | SEQ ID NO: |
|---|---|---|
| EV-D68_UT_R3 | ACGCACTTGACTTGTCTTCATTATTACTACTACCATTCACTGCTACA | 148 |
| EV-D68_UT_R4 | ACGCACTTGACTTGTCTTCTCAAATCCAGCAAAGCCATCA | 149 |
| EV-D68_UT_R5 | ACGCACTTGACTTGTCTTCAGAATACACTAGCATTACTACCTGACT | 150 |
| flaB_UT1_F | ACCCAACTGAATGGAGCGCWTCTGATGATGCTGCTGGIA | 151 |
| flaB_UT1_R1 | ACGCACTTGACTTGTCTTCGCATTCCAAGYTCTTCAGCTGT | 152 |
| flaB_UT1_R2 | ACGCACTTGACTTGTCTTCGCATTCCAAGCTCTTCAGCWGT | 153 |
| flaB_UT2_F1 | ACCCAACTGAATGGAGCACACCAGCRTCRCTTTCAGG | 154 |
| flaB_UT2_F2 | ACCCAACTGAATGGAGCACACCAGCATCAYTAKCTGGA | 155 |
| flaB_UT2_F3 | ACCCAACTGAATGGAGCACACCAGCATCATTRGCTGGA | 156 |
| flaB_UT2_R1 | ACGCACTTGACTTGTCTTCTTGGAAAGCACCTAAATTTGCYCTT | 157 |
| flaB_UT2_R2 | ACGCACTTGACTTGTCTTCTTGRAAAGCACCAAGATTTGCTCTT | 158 |
| flaB_UT2_R3 | ACGCACTTGACTTGTCTTCTTGGAAAGCACCYAAATTTGCTCTT | 159 |
| Ft-G_UT_F | ACCCAACTGAATGGAGCCTAAGCCATAAGCCCTTTCTCTAACTTGT | 160 |
| Ft-G_UT_R | ACGCACTTGACTTGTCTTCAGCAATGACAAAGCTTGTTGAAAAAG | 161 |
| glpQ_UT1_F1 | ACCCAACTGAATGGAGCCCAGAACATACCTTAGAAKCTAAAGC | 162 |
| glpQ_UT1_F2 | ACCCAACTGAATGGAGCCAGAACATACATTAGAAGCCAAAGC | 163 |
| glpQ_UT1_R1 | ACGCACTTGACTTGTCTTCCCTTGTTGYTTATGCCATAAKGGTT | 164 |
| glpQ_UT1_R2 | ACGCACTTGACTTGTCTTCCCTTGTTGTTTATGCCAHAAGGGTT | 165 |
| glpQ-Halp_UT2_F1 | ACCCAACTGAATGGAGCCCAGAACATACCTTAGAAKCTAAAGC | 166 |
| glpQ-Halp_UT2_F2 | ACCCAACTGAATGGAGCCAGAACATACATTAGAAGCCAAAGC | 167 |
| glpQ-Halp_UT2_R1 | ACGCACTTGACTTGTCTTCCACATTAGCAGAAATCAAATCAC | 168 |
| glpQ-Halp_UT2_R2 | ACGCACTTGACTTGTCTTCGATCAAATCTTTCGCTAAGRCTTAGTG | 169 |
| glpQ-Halp_UT2_R3 | ACGCACTTGACTTGTCTTCGATCAAATCTTTCACTGAGACTTAGTG | 170 |
| glpQ-Halp_UT2_R4 | ACGCACTTGACTTGTCTTCGATCAAATCTTTCACTAAGGCTTAATG | 171 |
| glpQ-Halp_UT2_R5 | ACGCACTTGACTTGTCTTCGGGTATCCARGGTCCAAT | 172 |
| H3N2_UT_F | ACCCAACTGAATGGAGCAAGACCAATYCTGTCACCTCTGA | 173 |
| H3N2_UT_R | ACGCACTTGACTTGTCTTCCAAAGCGTCTACGCTGCAGTCC | 174 |
| IGS1-Bunikis_UT1_F | ACCCAACTGAATGGAGCGTATGTTTAGTGAGGGGGGTG | 175 |
| IGS1-Bunikis_UT1_R | ACGCACTTGACTTGTCTTCGGATCATAGCTCAGGTGGTTAG | 176 |
| IGS1-Bunikis_UT2_F | ACCCAACTGAATGGAGCAGGGGGGTGAAGTCGTAACAAG | 177 |
| IGS1-Bunikis_UT2_R | ACGCACTTGACTTGTCTTCGTCTGATAAACCTGAGGTCGGA | 178 |
| IGS2-Derdakova_UT_F | ACCCAACTGAATGGAGCCGACCTTCTTCGCCTTAAAGC | 179 |
| IGS2-Derdakova_UT_R | ACGCACTTGACTTGTCTTCAGCTCTTATTCGCTGATGGTA | 180 |
| IGS-5S-23S-Postic_UT_F | ACCCAACTGAATGGAGCCTGCGAGTTCGCGGGAGA | 181 |
| IGS-5S-23S-Postic_UT_R | ACGCACTTGACTTGTCTTCTCCTAGGCATTCACCATA | 182 |
| IGS-5S-23S-TK_UT_F | ACCCAACTGAATGGAGCGAGTTCGCGGGAGAGTAGGTTATTGCC | 183 |
| IGS-5S-23S-TK_UT_R | ACGCACTTGACTTGTCTTCTCAGGGTACTTAGATGKTTCACTTCC | 184 |

TABLE 2-continued

Primers for LymeSeq Lyme Disease Next-Generation Sequencing Diagnostic Assay with the universal tail targets. ACCCAACTGAATGGAGC (SEQ ID NO: 217) or ACGCACTTGACTTGTCTTC (SEQ ID NO: 218).

| Primer | Sequence with Universal Tail Target | SEQ ID NO: |
|---|---|---|
| IPC-gapDH_UT1_F | ACCCAACTGAATGGAGCCCTGCCAAATATGATGACATCAAG | 185 |
| IPC-gapDH_UT1_R | ACGCACTTGACTTGTCTTCGTGGTCGTTGAGGGCAATG | 186 |
| ospA-Rudenko_UT_F | ACCCAACTGAATGGAGCGAGCTTAAAGGAACTTCTGATAA | 187 |
| ospA-Rudenko_UT_R | ACGCACTTGACTTGTCTTCGTATTGTTGTACTGTAATTGT | 188 |
| ospB_UT1_F | ACCCAACTGAATGGAGCTGCGGTGACAGAAGACTC | 189 |
| ospB_UT1_R | ACGCACTTGACTTGTCTTCCAGCAGAAACTGTTAATTTTACTTTACTC | 190 |
| ospB_UT2_F | ACCCAACTGAATGGAGCTGCGGTGACAGAAGACTC | 191 |
| ospB_UT2_R | ACGCACTTGACTTGTCTTCAATCAGCAGAAACTGTTAATTTTACTTTAC | 192 |
| ospC-Bunikis_UT1_F | ACCCAACTGAATGGAGCATGAAAAAGAATACATTAAGTGC | 193 |
| ospC-Bunikis_UT1_R | ACGCACTTGACTTGTCTTCATTAATCTTATAATATTGATTTTAATTAAGG | 194 |
| ospC-Bunikis_UT2_F | ACCCAACTGAATGGAGCTATTAATGACTTTATTTTTATTTATATCT | 195 |
| ospC-Bunikis_UT2_R | ACGCACTTGACTTGTCTTCTTGATTTTAATTAAGGTTTTTTTGG | 196 |
| ospC-Wang_UT1_F | ACCCAACTGAATGGAGCAAAGAATACATTAAGTGCGATATT | 197 |
| ospC-Wang_UT1_R | ACGCACTTGACTTGTCTTCGGGCTTGTAAGCTCTTTAACT | 198 |
| ospD_UT1_F | ACCCAACTGAATGGAGCGAGCTTAAAGGAACTTCTGATAA | 199 |
| ospD_UT1_R | ACGCACTTGACTTGTCTTCGTATTGTTGTACTGTAATTGT | 200 |
| p66_UT1_F | ACCCAACTGAATGGAGCGAGCTTAAAGGAACTTCTGATAA | 201 |
| p66_UT1_R | ACGCACTTGACTTGTCTTCGTATTGTTGTACTGTAATTGT | 202 |
| p66_UT2_F | ACCCAACTGAATGGAGCGAGCTTAAAGGAACTTCTGATAA | 203 |
| p66_UT2_R | ACGCACTTGACTTGTCTTCGTATTGTTGTACTGTAATTGT | 204 |
| p66-Bunikis_UT1_F | ACCCAACTGAATGGAGCGATTTTTCTATATTTGGACACAT | 205 |
| p66-Bunikis_UT1_R | ACGCACTTGACTTGTCTTCTGTAAATCTTATTAGTTTTTCAAG | 206 |
| p66-Bunikis_UT2_F | ACCCAACTGAATGGAGCCAAAAAAGAAACACCCTCAGATCC | 207 |
| p66-Bunikis_UT2_R | ACGCACTTGACTTGTCTTCCCTGTTTTTAAATAAATTTTTGTAGCATC | 208 |
| p66-Rudenko_UT1_F | ACCCAACTGAATGGAGCCGAAGATACTAAATCTGT | 209 |
| p66-Rudenko_UT1_R | ACGCACTTGACTTGTCTTCGCTGCTTTTGAGATGTGTCC | 210 |
| parA_UT1_F | ACCCAACTGAATGGAGCGAGCTTAAAGGAACTTCTGATAA | 211 |
| parA_UT1_R | ACGCACTTGACTTGTCTTCGTATTGTTGTACTGTAATTGT | 212 |
| Yp3a_UT_F | ACCCAACTGAATGGAGCCATTGGACGGCATCACGAT | 213 |
| Yp3a_UT_R | ACGCACTTGACTTGTCTTCAGTTGGCCAGCGATTCGA | 214 |
| Ypp1a_UT_F | ACCCAACTGAATGGAGCGAAAGGAGTGCGGGTAATAGGTT | 215 |
| Ypp1a_UT_R | ACGCACTTGACTTGTCTTCGGCCTGCAAGTCCAATATATGG | 216 |

TABLE 3

Additional primers for LymeSeq Lyme Disease Next-Generation Sequencing Diagnostic Assay with the universal tail targets ACCCAACTGAATGGAGC (SEQ ID NO: 217) or ACGCACTTGACTTGCTTC (SEQ ID NO: 218).

| Target Purpose | Target Taxon | Target Gene/ Region | UT Assay Type | Assay | Primer | Sequence without UT | SEQ ID NO: |
|---|---|---|---|---|---|---|---|
| Species ID | Borrelia spp. | 16S-set of 5 assays to cover whole gene | Sequence-based | 16S-1_UT | 16S-1_UT_F | ACCCAACTGAATGG AGCGGGTGAGTAA CGCGTGAT | 315 |
| | | | | | 16S-1_UT_R | ACGCACTTGACTTG TCTTCCCTCTCAGG CCGGTTACTTATC | 316 |
| | | | | 16S-2_UT | 16S-2_UT_F | ACCCAACTGAATGG AGCCGGTCAACACTG GAACTGAGA | 317 |
| | | | | | 16S-2_UT_R | ACGCACTTGACTTG TCTTCGCTGCTGGC ACGTAATTAGC | 318 |
| | | | | 16S-3_UT | 16S-3_UT_F | ACCCAACTGAATGG AGCGCGGAGCGTTGT TCGGGAT | 319 |
| | | | | | 16S-3_UT_R | ACGCACTTGACTTG TCTTCACTCAGCGT CAGTCTTGACC | 320 |
| | | | | 16S-4_UT | 16S-4_UT_F | ACCCAACTGAATGG AGCCGCTGTAAACG ATGCACTTG | 321 |
| | | | | | 16S-4_UT_R | ACGCACTTGACTTG TCTTCACAACCATG CAGCACCTGTA | 322 |
| | | | | 16S-5_UT | 16S-5_UT_F | ACCCAACTGAATGG AGCGCAACGAGCGC AACCCTT | 323 |
| | | | | | 16S-5_UT_R | ACGCACTTGACTTG TCTTCTACAAGGCC CGAGAACGTATTCA C | 324 |

TABLE 3-continued

Additional primers for LymeSeq Lyme Disease Next-Generation Sequencing Diagnostic Assay with the universal tail targets ACCCAACTGAATGGAGC (SEQ ID NO: 217) or ACGCACTTGACTTGCTTC (SEQ ID NO: 218).

| Target Purpose | Target Taxon | Target Gene/ Region | UT Assay Type | Assay | Primer | Sequence without UT | SEQ ID NO: |
|---|---|---|---|---|---|---|---|
| Species ID | Borrelia spp. | IGS2 5S-23S | Sequence-based | IGS-5S-23S-Postic_UT | IGS2-5S-23S-Postic_UT_F | ACCCAACTGAATGGAGCCTGCGAGTTCGCGGGAGA | 325 |
|  |  |  |  |  | IGS-5S-23S-Postic_UT_R | ACGCACTTGACTTGTCTTCCCTAGGCATTCACCATA | 326 |
| Species ID new assays 062216 | Borrelia spp. | 16S-23S IGS | IGS rrs-rrlA | rrs-rrlA_UT1 | rrs-rrlA_UT1_F1 | ACCCAACTGAATGGAGCGGGTTCGAGTCCCTYAACCT | 327 |
|  |  |  |  |  | rrs-rrlA_UT1_F2 | ACCCAACTGAATGGAGCTTGGTTTAGAGCATCGGCTTTGC | 328 |
|  |  |  |  |  | rrs-rrlA_UT1_R1 | ACGCACTTGACTTGTCTTCCCTTGCACTTTAGCGAAACAAC | 329 |
|  |  |  |  |  | rrs-rrlA_UT1_R2 | ACGCACTTGACTTGTCTTCCCTTGTGCTTTAGTGAAACAAC | 330 |
|  |  |  |  |  | rrs-rrlA_UT1_R3 | ACGCACTTGACTTGTCTTCACTTGCCATACGTAAACACCGT | 331 |
|  |  |  |  |  | rrs-rrlA_UT1_R4 | ACGCACTTGACTTGTCTTCCTCATGACTTGTCACACGTAAACAAC | 332 |
|  |  |  |  |  | rrs-rrlA_UT1_R5 | ACGCACTTGACTTGTCTTGTTCAACTCCTCCTGGTCCCAA | 333 |
|  |  |  |  |  | rrs-rrlA_UT1_R6 | ACGCACTTGACTTGTCTTCATCCTATAGATGCAATCTCTTGWCC | 334 |
|  |  |  |  |  | rrs-rrlA_UT1_R7 | ACGCACTTGACTTGTCTTCTTGCATGTA | 335 |

TABLE 3-continued

Additional primers for LymeSeq Lyme Disease Next-Generation Sequencing Diagnostic Assay with the universal tail targets ACCCAACTGAATGGAGC (SEQ ID NO: 217) or ACGCACTTGACTTGTCTTC (SEQ ID NO: 218).

| Target Purpose | Target Taxon | Target Gene/ Region | UT Assay Type | Assay | Primer | Sequence without UT | SEQ ID NO: |
|---|---|---|---|---|---|---|---|
| | | | | | rrs-rrlA_UT1_R8 | ATCAAGTCTTGGAATTC | |
| | | | | | | ACGCACTTGACTTGTCTTCTACTTTCACCTCTAGACATTCTTGT | 336 |
| | | | | | rrs-rrlA_UT1_R9 | ACGCACTTGACTTGTCTTCTAGGTTGATTCATGATCAGGTCCTT | 337 |
| | | | | | rrs-rrlA_UT1_R10 | ACGCACTTGACTTGTCTTCCGAATTCGGTCACGGCTCTTAC | 338 |
| | | | | | rrs-rrlA_UT1_R11 | ACGCACTTGACTTGTCTTCCCTTATGATTTAGTAACACAGTAAGT | 339 |
| | | | | | rrs-rrlA_UT1_R12 | ACGCACTTGACTTGTCTTCAAGCTAGTAATGAATGTGGGATGTT | 340 |
| Species ID | Borrelia spp. | flaB | Sequence-based | flaB_UT1 | flaB_UT1_F | ACCCAACTGAATGGAGCGCWTCTGATGATGCTGCTGGIA | 341 |
| | | | | | flaB_UT1_R1 | ACGCACTTGACTTGTCTTCCGCATTCCAAGYTCTTCAGCTGT | 342 |
| | | | | | flaB_UT1_R2 | ACGCACTTGACTTGTCTTCGGCATTCCAAGCTCTTCAGCWGT | 343 |
| | | | flaB_UT2 | flaB_UT2_F1 | ACCCAACTGAATGGAGCACCAGCRTCRCTTTCAGG | 344 |

TABLE 3-continued

Additional primers for LymeSeq Lyme Disease Next-Generation Sequencing Diagnostic Assay with the universal tail targets ACCCAACTGAATGGAGC (SEQ ID NO: 217) or ACGCACTTGACTTGCTTC (SEQ ID NO: 218).

| Target Purpose | Target Taxon | Target Gene/ Region | UT Assay Type | Assay | Primer | Sequence without UT | SEQ ID NO: |
|---|---|---|---|---|---|---|---|
| | | | | | flaB_UT2_F2 | ACCCAACTGAATGG AGCACACCAGCATC AYTAKCTGGA | 345 |
| | | | | | flaB_UT2_F3 | ACCCAACTGAATGG AGCACACCAGCATC ATTRGCTGGA | 346 |
| | | | | | flaB_UT2_R1 | ACGCACTTGACTTG TCTTCTTGGAAAGC ACCTAAATTTGCYC TT | 347 |
| | | | | | flaB_UT2_R2 | ACGCACTTGACTTG TCTTCTTGRAAAGC ACCAAGATTTGCTC TT | 348 |
| | | | | | flaB_UT2_R3 | ACGCACTTGACTTG TCTTCTTGGAAAGC ACCYAAATTTGCTC TT | 349 |
| Species ID | non-Burgdorferi Borrelia spp. | glpQ | Sequence-based | glpQ_UT1 | glpQ_UT1_F1 | ACCCAACTGAATGG AGCCCAGAACATAC CTTAGAAKCTAAAG C | 350 |
| | | | | | glpQ_UT1_F2 | ACCCAACTGAATGG AGCCAGAACATACA TTAGAAGCCAAAGC | 351 |
| | | | | | glpQ_UT1_R1 | ACGCACTTGACTTG TCTTCCCTTGTTGYT TATGCCATAAKGGT T | 352 |
| | | | | | glpQ_UT1_R2 | ACGCACTTGACTTG TCTTCCCTTGTTGTT TATGCCAHAAGGGT T | 353 |

TABLE 3-continued

Additional primers for LymeSeq Lyme Disease Next-Generation Sequencing Diagnostic Assay with the universal tail targets ACCCAACTGAATGGAGC (SEQ ID NO: 217) or ACGCACTTGACTTGCTTC (SEQ ID NO: 218).

| Target Purpose | Target Taxon | Target Gene/ Region | Assay | UT Assay Type | Primer | Sequence without UT | SEQ ID NO: |
|---|---|---|---|---|---|---|---|
| Species ID | B. burgdorferiss | bbk32 | bbk32_UT | presence/absence | bbk32_UT_F1 | ACCCAACTGAATGG AGCTGAGGAGMC TATTGAAAGYAATG | 354 |
| | | | | | bbk32_UT_F2 | ACCCAACTGAATGG AGCTGAAGGAKACT ATTGAAAGYAATG | 355 |
| | | | | | bbk32_UT_R1 | ACGCACTTGACTTG TCTTCGCGTGTAGA ATACATTTGGGTTA GC | 356 |
| | | | | | bbk32_UT_R2 | ACGCACTTGACTTG TCTTCGACGTGTAG AATACATTTGGGTT TGC | 357 |
| Species ID | B. burgdorferi | dbpA | dbpA_UT2 | presence/absence | dbpA_UT2_F1 | ACCCAACTGAATGG AGCCAGCCGCATCT GTAACTG | 358 |
| | | | | | dbpA_UT2_F2 | ACCCAACTGAATGG AGCTCAGTTCCCAT TGAAACTG | 359 |
| | | | | | dbpA_UT2_F3 | ACCCAACTGAATGG AGCTTYAGCYGCAT CTGAGAC | 360 |
| | | | | | dbpA_UT2_F4 | ACCCAACTGAATGG AGCTTCAGCTGCCW TTGAGAC | 361 |
| | | | | | dbpA_UT2_R1 | ACGCACTTGACTTG TCTTCCAGGYAGCA AGGTATCAGA | 362 |
| | | | | | dbpA_UT2_R2 | ACGCACTTGACTTG TCTTCCRGGTAGYG GGGTATCAGA | 363 |

TABLE 3-continued

Additional primers for LymeSeq Lyme Disease Next-Generation Sequencing Diagnostic Assay with the universal tail targets ACCCAACTGAATGGAGC (SEQ ID NO: 217) or ACGCACTTGACTTGCTTC (SEQ ID NO: 218).

| Target Purpose | Target Taxon | Target Gene/ Region | Assay | UT Assay Type | Primer | Sequence without UT | SEQ ID NO: |
|---|---|---|---|---|---|---|---|
| | | | | | dbpA_UT2_R3 | ACGCACTTGACTTG TCTTCAACAGTRG AAAGYAGCA | 364 |
| Species ID | B. burgdorferi | dbpB | dbpB_UT2 | presence/absence | dbpB_UT2_F_1 | ACCCAACTGAATGG AGCCGCAAGCAATC TTTCAGYTGTGT | 365 |
| | | | | | dbpB_UT2_F2 | ACCCAACTGAATGG AGCCTCAACCAATC TTTCAGCYGTGT | 366 |
| | | | | | dbpB_UT2_F3 | ACCCAACTGAATGG AGCCTTCAAGCAAT CTTTCACATGTGT | 367 |
| | | | | | dbpB_UT2_F4 | ACCCAACTGAATGG AGCCCTCAATTAAT CTTTCAGATGTGCT | 368 |
| | | | | | dbpB_UT2_F5 | ACCCAACTGAATGG AGCTTCAAGCAATC TTTCGGCTGTGT | 369 |
| | | | | | dbpB_UT2_F6 | ACCCAACTGAATGG AGCCTCCATTACTC TTTCGGCTGTGT | 370 |
| | | | | | dbpB_UT2_R1 | ACGCACTTGACTTG TCTTCRYAGCKCTT GAATCRTCYTYTAA GG | 371 |
| | | | | | dbpB_UT2_R2 | ACGCACTTGACTTG TCTTCAAGCAATGC TTGAATCSTMTTCT GA | 372 |
| | | | | | dbpB_UT2_R3 | ACGCACTTGACTTG TCTTCAAGCAAAGC TTGAATCGTCTTCC | 373 |
| Species ID | Anaplasma phagocyto- | msp2 (major surface protein) | Ana- msp2_UT2 | | Ana- msp2_UT2_F | ACCCAACTGAATGG AGCGGGAGAGTAA | 374 |

TABLE 3-continued

Additional primers for LymeSeq Lyme Disease Next-Generation Sequencing Diagnostic Assay with the universal tail targets ACCCAACTGAATGGAGC (SEQ ID NO: 217) or ACGCACTTGACTTGCTTC (SEQ ID NO: 218).

| Target Purpose | Target Taxon | Target Gene/ Region | UT Assay Type | Assay | Primer | Sequence without UT | SEQ ID NO: |
|---|---|---|---|---|---|---|---|
| | phylum | | | | | CGGAGARACWAAGG | |
| | | | | | Ana-msp2_UT2_R1 | ACGCACTTGACTTGTCTTCCTGGCACCACCAATACCATAACC | 375 |
| | | | | | Ana-msp2_UT2_R2 | ACGCACTTGACTTGTCTTCCTGGCACCACCAATACCRTACC | 376 |
| Species ID | Ehrlichia genus | 16S | Sequence-based | Ehrl-16S_UT | Ehrl-16S_UT_F | ACCCAACTGAATGGAGCAGGATTTTATCTTTGTATTGTAGCTAAC | 377 |
| | | | | | Ehrl-16S_UT_R | ACGCACTTGACTTGTCTTGTAAGGTCCAGCCGAACTGACT | 378 |
| Species ID | Ehrlichia genus | 16S | Sequence-based | Ehrl-16S_UT2 | Ehrl-16S_UT2_F | ACCCAACTGAATGGAGCCAGGATTAGATACCCTGGTAGTCCA | 379 |
| | | | | | Ehrl-16S_UT2_R | ACGCACTTGACTTGTCTTCACGACGAGCTGACGACA | 380 |
| Species ID | Ehrlichia genus | sodB | presence/absence | Ehrl-sodB_UT | Ehrl-sodB_UT_F | ACCCAACTGAATGGAGCTTTAATAATGCTGGTCAAGTATGGAATCAT | 381 |
| | | | | | Ehrl-sodB_UT_R | ACGCACTTGACTTGTCTTCAAGCRTGYTCCCATACATCCATAG | 382 |
| Species ID | B. burgdorferi | ospB | presence/absence | ospB_UT3 | ospB_UT3_F1 | ACCCAACTGAATGGAGCGTYGAACTTAAAGGAACTTCCGAT | 383 |

TABLE 3-continued

Additional primers for LymeSeq Lyme Disease Next-Generation Sequencing Diagnostic Assay with the universal tail targets ACCCAACTGAATGGAGC (SEQ ID NO: 217) or ACGCACTTGACTTGCTTC (SEQ ID NO: 218).

| Target Purpose | Target Taxon | Target Gene/ Region | UT Assay Type | Assay | Primer | Sequence without UT | SEQ ID NO: |
|---|---|---|---|---|---|---|---|
| | | | | | ospB_UT3_F2 | ACCCAACTGAATGG AGCNTTGAGCTWA AAGGAACWTCTGA T | 384 |
| | | | | | ospB_UT3_F3 | ACCCAACTGAATGG AGCGTTGAGCTTAA AGGRGTTKCTGA | 385 |
| | | | | | ospB_UT3_F4 | ACCCAACTGAATGG AGCGGTGAGCTTAA AGGGATTTTGA | 386 |
| | | | | | ospB_UT3_F5 | ACCCAACTGAATGG AGCGTTGAGCTTAA AGGCCTTTCTGAG | 387 |
| | | | | | ospB_UT3_R1 | ACGCACTTGACTTG TCTTCCCGMCTMCA AGACTTCCTTCA | 388 |
| | | | | | ospB_UT3_R2 | ACGCACTTGACTTG TCTTCCGCCTACA AGATTTCCTGGA | 389 |
| | | | | | ospB_UT3_R3 | ACGCACTTGACTTG TCTTCCACCAACA AGACTTCCTTCTAG T | 390 |
| | | | | | ospB_UT3_R4 | ACGCACTTGACTTG TCTTCCACCAACT AGACTTCCTTTAAA C | 391 |
| | | | | | ospB_UT3_R5 | ACGCACTTGACTTG TCTTCCACCAACA AGATTTCCTTCGAA C | 392 |
| | | | | | ospB_UT3_R6 | ACGCACTTGACTTG TCTTCCATTAGCTA CTTTTCCTTCAAGA G | 393 |

TABLE 3-continued

Additional primers for LymeSeq Lyme Disease Next-Generation Sequencing Diagnostic Assay with the universal tail targets ACCCAACTGAATGGAGC (SEQ ID NO: 217) or ACGCACTTGACTGCTTC (SEQ ID NO: 218).

| Target Purpose | Target Taxon | Target Gene/ Region | UT Assay Type | Assay | Primer | Sequence without UT | SEQ ID NO: |
|---|---|---|---|---|---|---|---|
| | | | | | ospB_UT3_R7 | ACGCACTTGACTTG TCTTCCATTAGCTA GAGTTCCTTCAAGA G | 394 |
| | | | | | ospB_UT3_R8 | ACGCACTTGACTTG TCTTCTCAGCAGYT AGAGTTCCTTCAAG A | 395 |
| Species ID | B. burgdorferi | ospC-TG | presence/absence | ospC-TG_UT1 | ospC-TG_UT1_F | ACCCAACTGAATGG AGCTCAGGRAAAGA TGGGAATRCATCTG C | 396 |
| | | | | | ospC-TG_UT1_R | ACGCACTTGACTTG TCTTCGRCTTGTAA GCTCTTTAACTGMA TTAG | 397 |
| Species ID | B. burgdorferi | p66 | presence/absence | p66_UT3 | p66_UT3_F1 | ACCCAACTGAATGG AGCGCCYATGACYG GATTCAAA | 398 |
| | | | | | p66_UT3_F2 | ACCCAACTGAATGG AGCTTYGCACCTAT GACTGRTTT | 399 |
| | | | | | p66_UT3_R | ACGCACTTGACTTG TCTTCGGYTTCCAT GTTGCTTGAAY | 400 |
| | | | | p66_UT4 | p66_UT4_F1 | ACCCAACTGAATGG AGCTGARGCTATCC ATCCAAGRCC | 401 |
| | | | | | p66_UT4_F2 | ACCCAACTGAATGG ACGGAAGCTGTCCA TCCAAGATTAG | 402 |
| | | | | | p66_UT4_R1 | ACGCACTTGACTTG TCTTCCGGTTTAGCT TGGAATACAGATGA | 403 |

TABLE 3-continued

Additional primers for LymeSeq Lyme Disease Next-Generation Sequencing Diagnostic Assay with the universal tail targets ACCCAACTGAATGGAGC (SEQ ID NO: 217) or ACGCACTTGACTGTCTTC (SEQ ID NO: 218).

| Target Purpose | Target Taxon | Target Gene/ Region | UT Assay Type | Assay | Primer | Sequence without UT | SEQ ID NO: |
|---|---|---|---|---|---|---|---|
| | | | | | p66_UT4_R2 | ACGCACTTGACTTG TCTTCCGGTTTTGCC TGGAATAAAGATGA | 404 |
| | | | | | p66_UT4_R3 | ACGCACTTGACTTG TCTTCGGCYTAGCT TGGAAYATAGATGA | 405 |
| | | | | p66_UT5 | p66_UT5_F | ACCCAACTGAATGG AGCGCAATMGGAA AYTCAACATTC | 406 |
| | | | | | p66_UT5_R | ACGCACTTGACTTG TCTTCCRCTTGCAA ATGGGTCTATTCCT | 407 |
| Species ID | B. burgdorferi | ospA | ospA | ospA_UT1 | ospA_UT1_F1 | ACCCAACTGAATGG AGCGGITCTGAAAY ACTTGAAGG | 408 |
| | | | | | ospA_UT1_F2 | ACCCAACTGAATGG AGCGGATCTGGRRT RCTTGAAGG | 409 |
| | | | | | ospA_UT1_F3 | ACCCAACTGAATGG AGCGGTTCTGAAAS CCTTGARGG | 410 |
| | | | | | ospA_UT1_F4 | ACCCAACTGAATGG AGCGGRYCTGGGGT RCTTGAAGG | 411 |
| | | | | | ospA_UT1_F5 | ACCCAACTGAATGG AGCGGATCTGGGGG AAAGCTTGAAG | 412 |
| | | | | | ospA_UT1_F6 | ACCCAACTGAATGG AGCGGTTCTGDGT RCTKGAAGG | 413 |
| | | | | | ospA_UT1_F7 | ACCCAACTGAATGG AGCGGATCTGGMW HGCYYGAAGG | 414 |

TABLE 3-continued

Additional primers for LymeSeq Lyme Disease Next-Generation Sequencing Diagnostic Assay with the universal tail targets ACCCAACTGAATGGAGC (SEQ ID NO: 217) or ACGCACTTGACTTGCTTC (SEQ ID NO: 218).

| Target Purpose | Target Taxon | Target Gene/ Region | UT Assay Type | Assay | Primer | Sequence without UT | SEQ ID NO: |
|---|---|---|---|---|---|---|---|
| | | | | | ospA_UT1_F8 | ACCCAACTGAATGG AGCGGMGCTGGAM AWCTTGAAGG | 415 |
| | | | | | ospA_UT1_R1 | ACGCACTTGACTTG TCTTCCAAGTYTGK TKCCRTTTKCTCTTG | 416 |
| | | | | | ospA_UT1_R2 | ACGCACTTGACTTG TCTTCCAAGYYTGG TWCCGTYTGCTCTT R | 417 |
| | | | | | ospA_UT1_R3 | ACGCACTTGACTTG TCTTCCMAGTGTAG TYCCGYTTGDTCTT G | 418 |
| | | | | | ospA_UT1_R4 | ACGCACTTGACTTG TCTTCCAAGTMTKG WWCCRTTTGCTCTT R | 419 |
| | | | | | ospA_UT1_R5 | ACGCACTTGACTTG TCTTCCAAGKGTAG TTTCGTTTKCTCTTG | 420 |
| | | | | | ospA_UT1_R6 | ACGCACTTGACTTG TCTTCCAAKTGTAG TATYRTTTGATCTTG | 421 |
| | | | | | ospA_UT1_R7 | ACGCACTTGACTTG TCTTCCAAGMKTRG TKCCGTTTGCTCTTG | 422 |
| | | | | | ospA_UT1_R8 | ACGCACTTGACTTG TCTTCCAAGTCTGG TTCCGTCTTTTCTTG | 423 |
| | | | | | ospA_UT1_R9 | ACGCACTTGACTTG TCTTCCAAGTGGTG TTCCGTTTGTTCTTG | 424 |

TABLE 3-continued

Additional primers for LymeSeq Lyme Disease Next-Generation Sequencing Diagnostic Assay with the universal tail targets ACCCAACTGAATGGAGC (SEQ ID NO: 217) or ACGCACTTGACTTGCTTC (SEQ ID NO: 218).

| Target Purpose | Target Taxon | Target Gene/ Region | UT Assay Type | Assay | Primer | Sequence without UT | SEQ ID NO: |
|---|---|---|---|---|---|---|---|
| | | | | | ospA_UT1_R10 | ACGCACTTGACTTG TCTTCCAAGTCTATT TCCATTTGCTCTTG | 425 |
| | | | | | ospA_UT1_R11 | ACGCACTTGACTTG TCTTCCAAGTCTGG TTCCGTTAYCTCTTA | 426 |
| | | | | | ospA_UT1_R12 | ACGCACTTGACTTG TCTTCCAAGTCTGG TTCCATTTGCCCTTA | 427 |
| Species ID | Borrelia burgdorferi | porin gene | presence/absence | p66-borrelia_UT2 | p66_UT2_F | ACCCAACTGAATGG AGCTGTAATTGCAG AAACACCTTTGA | 428 |
| | | | | | p66_UT2_R | ACGCACTTGACTTG TCTTGCTGCTTTTG AGATGTGTCC | 429 |
| Genus ID | Bartonella | ssrA | presence/absence | Bart-ssrA_UT1 | Bart-ssrA_UT1_F | ACCCAACTGAATGG AGCGGCTAAATIAG TAGTTGCAAAYGAC A | 430 |
| | | | | | Bart-ssrA_UT1_R | ACGCACTTGACTTG TCTTGCTTCTGTTG CCAGGTG | 431 |
| Genus ID | Babesia | 18S | sequence-based | Babe-18S_UT1 | Babe-18S_UT1_F | ACCCAACTGAATGG AGCACCGTCCAAAG CTGATAGGTC | 432 |
| | | | | | Babe-18S_UT1_R | ACGCACTTGACTTG TCTTCCGAAACTGC GAATGGCTCATTA | 433 |
| Genus ID | Rickettsia | ompA | presence/absence | Rkttsia-ompA_UT1 | Rkttsia-ompA_UT1_F | ACCCAACTGAATGG AGCGGCCATTTACTT ACRGTGSTGAT | 434 |
| | | | | | Rkttsia-ompA_UT1_R | ACGCACTTGACTTG TCTTCCATGATTTG CAGCAAYAGCAT | 435 |

TABLE 3-continued

Additional primers for LymeSeq Lyme Disease Next-Generation Sequencing Diagnostic Assay with the universal tail targets ACCCAACTGAATGGAGC (SEQ ID NO: 217) or ACGCACTTGACTTGCTTC (SEQ ID NO: 218).

| Target Purpose | Target Taxon | Target Gene/ Region | UT Assay Type | Assay | Primer | Sequence without UT | SEQ ID NO: |
|---|---|---|---|---|---|---|---|
| | | | | Rkttsia-ompA_UT2 | Rkttsia-ompA_UT2_F | ACCCAACTGAATGG AGCCGYTAGCTGGG CTTAGRTATTC | 436 |
| | | | | | Rkttsia-ompA_UT2_R | ACGCACTTGACTTG TCTTCCGCCGRAAC TTTATTCTTGAATG | 437 |
| | | | | Rkttsia-ompA_UT3 | Rkttsia-ompA_UT3_F | ACCCAACTGAATGG AGCACTTAYGGTGG TGATTATAYTATC | 438 |
| | | | | | Rkttsia-ompA_UT3_R | ACGCACTTGACTTG TCTTCTGCAGCAAC AGCATTAKTACYG | 439 |
| | | | | Rkttsia-ompA_UT4 | Rkttsia-ompA_UT4_F1 | ACCCAACTGAATGG AGCGCTGRAGGAGT AGCTAATGGT | 440 |
| | | | | | Rkttsia-ompA_UT4_F2 | ACCCAACTGAATGG AGCGCAGCAGGAGT AGCTGATGAT | 441 |
| | | | | | Rkttsia-ompA_UT4_R | ACGCACTTGACTTG TCTTCMCGCAGCAG TACCGGTTAAAG | 442 |
| | | | | Rkttsia-ompA_UT5 | Rkttsia-ompA_UT5_F | ACCCAACTGAATGG AGCCAACCGCAGCR WTAATGCTAAC | 443 |
| | | | | | Rkttsia-ompA_UT5_R | ACGCACTTGACTTG TCTTCCCTCCCGTAT CTACCACTGAAC | 444 |
| | | | | Rkttsia-ompA_UT6 | Rkttsia-ompA_UT6_F | ACCCAACTGAATGG AGCTGCAGGAGCAG ATAATGGTA | 445 |
| | | | | | Rkttsia-ompA_UT6_R | ACGCACTTGACTTG TCTTCGCCGGCAGT AATAGTAACAG | 446 |

TABLE 3-continued

Additional primers for LymeSeq Lyme Disease Next-Generation Sequencing Diagnostic Assay with the universal tail targets ACCCAACTGAATGGAGC (SEQ ID NO: 217) or ACGCACTTGACTTGCTTC (SEQ ID NO: 218).

| Target Purpose | Target Taxon | Target Gene/ Region | UT Assay Type | Assay | Primer | Sequence without UT | SEQ ID NO: |
|---|---|---|---|---|---|---|---|
| | | | | Rkttsia-ompA_UT7 | Rkttsia-ompA_UT7_F1 | ACCCAACTGAATGG AGCGGTGCAAGCCA AGTAACATATAC | 447 |
| | | | | | Rkttsia-ompA_UT7_F2 | ACCCAACTGAATGG AGCAGTACAAATC AAGTAACATATACC | 448 |
| | | | | | Rkttsia-ompA_UT7_R1 | ACGCACTTGACTTG TCTTCAAACCGCCT TCCGTTTCTG | 449 |
| | | | | | Rkttsia-ompA_UT7_R2 | ACGCACTTGACTTG TCTTCAATCCACCT GCCGTTTCTG | 450 |
| Genus ID | Powassan and deer tick viruses | | presence/absence | Powass_UT | Powass_UT_F1 | ACCCAACTGAATGG AGCGGCDGTAGGYC ATGTTTATGAC | 451 |
| | | | | | Powass_UT_F2 | ACCCAACTGAATGG AGCAGCTGTGGGCC ACGTCTATGAC | 452 |
| | | | | | Powass_UT_R1 | ACGCACTTGACTTG TCTTCCGAAGGCA GGTGATCTTTG | 453 |
| | | | | | Powass_UT_R2 | ACGCACTTGACTTG TCTTCCAGAAGGCA GGTGGTCCTTG | 454 |
| Internal control | Human | gapDH | presence/absence | IPC-gapDH_UT1 | IPC-gapDH_UT1_F | ACCCAACTGAATGG AGCCCTGCCAAATA TGATGACATCAAG | 455 |
| | | | | | IPC-gapDH_UT1_R | ACGCACTTGACTTG TCTTCGTGTCGTT GAGGGCAATG | 456 |
| Differential diagnostics | Enterovirus strain D68 | VP1 | presence/absence | EV-D68_UT | EV-D68_UT_F1 | ACCCAACTGAATGG AGCACCAGARGAA GCCATACAAAC | 457 |

TABLE 3-continued

Additional primers for LymeSeq Lyme Disease Next-Generation Sequencing Diagnostic Assay with the universal tail targets ACCCAACTGAATGGAGC (SEQ ID NO: 217) or ACGCACTTGACTGTCTTC (SEQ ID NO: 218).

| Target Purpose | Target Taxon | Target Gene/ Region | UT Assay Type | Assay | Primer | Sequence without UT | SEQ ID NO: |
|---|---|---|---|---|---|---|---|
| | | | | | EV-D68_UT_F2 | ACCCAACTGAATGGAGCTGACACTTCAAGCAATGTTCGTA | 458 |
| | | | | | EV-D68_UT_F3 | ACCCAACTGAATGGAGCAACGCCGAACTTGGTGTG | 459 |
| | | | | | EV-D68_UT_F4 | ACCCAACTGAATGGAGCAACACCGAACCAGAGGAAG | 460 |
| | | | | | EV-D68_UT_R1 | ACGCACTTGACTTGTCTTCTGACACTTCAAGCAATGTTCGTA | 461 |
| | | | | | EV-D68_UT_R2 | ACGCACTTGACTTGTCTTCAACGCCGAACTTGGTGTG | 462 |
| | | | | | EV-D68_UT_R3 | ACGCACTTGACTTGTCTTCAACACCGAACCAGAGGAAG | 463 |
| | | | | | EV-D68_UT_R4 | ACGCACTTGACTTGTCTTCSCTGAYTGCCARTGGAATGAA | 464 |
| | | | | | EV-D68_UT_R5 | ACGCACTTGACTTGTCTTCATGTGCTGTTATTGCTACCTACTG | 465 |
| Differential diagnostics | Staphylococcus aureus | | | Sa_M4_UT2 | Sa_M4_UT2_F | ACCCAACTGAATGGAGCTAGCGTTGGTATTAAGTGGTTGT | 466 |
| | | | | | Sa_M4_UT2_R | ACGCACTTGACTTGTCTTCTCAAATCCAGCAAAGCCATCA | 467 |
| Differential diagnostics | Influenza A | matrix gene | presence/absence | H3N2_UT | H3N2_UT_F | ACCCAACTGAATGGAGCAAGACCAATYCTGTCACCTCTGA | 468 |

TABLE 3-continued

Additional primers for LymeSeq Lyme Disease Next-Generation Sequencing Diagnostic Assay with the universal tail targets ACCCAACTGAATGGAGC (SEQ ID NO: 217) or ACGCACTTGACTTGCTTC (SEQ ID NO: 218).

| Target Purpose | Target Taxon | Target Gene/ Region | UT Assay Type | Assay | Primer | Sequence without UT | SEQ ID NO: |
|---|---|---|---|---|---|---|---|
| | | | RNA target | | H3N2_UT_R | ACGCACTTGACTTG TCTTCTAGCGTTGG TATTAAGTGGTTGT | 469 |
| Differ- ential diag- nostics | Yersinia pestis | plasmid | | Ypp1a_UT | Ypp1a_UT_F | ACCCAACTGAATGG AGCGAAAGGAGTG CGGGTAATAGGTT | 470 |
| | | | | | Ypp1a_UT_R | ACGCACTTGACTTG TCTTCAAGACCAAT YCTGTCACCTCTGA | 471 |
| | | chromosome | | Yp3a_UT | Yp3a_UT_F | ACCCAACTGAATGG AGCCATTGGACGGC ATCACGAT | 472 |
| | | | | | Yp3a_UT_R | ACGCACTTGACTTG TCTTCGAAAGGAGT GCGGGTAATAGGTT | 473 |
| Differ- ential diag- nostics | Francisella tularensis | | SNP | Ft-G_UT | Ft-G_UT_F | ACCCAACTGAATGG AGCCTAAGCCATAA GCCCTTTCTCTAACT TGT | 474 |
| | | | | | Ft-G_UT_R | ACGCACTTGACTTG TCTTCCATTGGACG GCATCACGAT | 475 |

We claim:

1. A method of detecting one or more *Borrelia* species causing Lyme Disease or tick-borne relapsing fever (TBRF) within a sample from a subject, the method comprising:
   a) subjecting DNA and/or RNA from the sample to a multiplex PCR amplification reaction with primers targeting:
      at least one region of *Borrelia* 16S rRNA;
      at least one region of a 16S-23S intergenic spacer (IGS1);
      at least one region of a 5S-23S intergenic spacer (IGS2);
      at least one region of a flagella subunit B (flaB) gene;
      at least one region of a bbk32 gene;
      at least one region of a dbpA gene;
      at least one region of a dbpB gene;
      at least one region of an ospA gene
      at least one region of an ospB gene;
      at least one region of an ospC gene;
      at least one region of a p66 porin gene; and
      at least one region of a glpQ gene; and
   b) analyzing amplification products resulting from the PCR amplification reaction to detect the one or more *Borrelia* species,
   wherein the amplification products are analyzed by next-generation sequencing (NGS) to determine the sequence of each amplification product and the sequence of each amplification product is mapped to a reference library of known *Borrelia* sequences to detect the one or more *Borrelia* species and to identify *Borrelia* species that cause Lyme Disease and *Borrelia* species that do not cause Lyme Disease.

2. The method of claim 1, wherein the sample comprises contaminating nucleic acids and the multiplex PCR amplification reaction produces amplicons for sequencing in the presence of more than a 1,000-fold excess of the contaminating nucleic acids with no discernible inhibition.

3. The method of claim 2, wherein the RNA from the sample is subject to the PCR amplification reaction.

4. The method of claim 1, wherein
   the at least one region of *Borrelia* 16S rRNA contain sequences selected from the group consisting of SEQ ID NOS: 1-10;
   the at least one region of the 16S-23S intergenic spacer (IGS1) contains sequences selected from the group consisting of SEQ ID NOS: 17-20 and 219-232;
   the at least one region of the 5S-23S intergenic spacer (IGS2) contains sequences selected from the group consisting of SEQ ID NOS: 11-16;
   the at least one region of the flagella subunit B (flaB) gene contains sequences selected from the group consisting of SEQ ID NOS: 21-29;
   the at least one region of the bbk32 gene contains sequences selected from the group consisting of SEQ ID NOS: 41-44;
   the at least one region of the dbpA gene contains sequences selected from the group consisting of SEQ ID NOS: 45-46 and 233-239;
   the at least one region of the dbpB gene contains sequences selected from the group consisting of SEQ ID NOS: 47-48 and 240-248;
   the at least one region of the ospA gene contains sequences selected from the group consisting of SEQ ID NOS: 274-293;
   the at least one region of the ospB gene contains sequences selected from the group consisting of SEQ ID NOS: 60-63 and 249-261;
   the at least one region of the ospC gene contains sequences selected from the group consisting of SEQ ID NOS: 64-69 and 262-263;
   the at least one region of the p66 porin gene contains sequences selected from the group consisting of SEQ ID NOS: 70-75 and 264-273; and
   the at least one region of the glpQ gene contains sequences selected from the group consisting of SEQ ID NOS: 30-40.

5. The method of claim 1, wherein the amplification products are analyzed by size determination with agarose gel electrophoresis.

6. The method of claim 1, wherein the primer pairs comprise a universal tail sequence.

7. The method of claim 1, wherein the one or more *Borrelia* species are selected from the group consisting of: *Borrelia afzelii*, *Borrelia americana*, *Borrelia andersonii*, *Borrelia anserina*, *Borrelia baltazardii*, *Borrelia bavariensis*, *Borrelia bissettii*, *Borrelia brasiliensis*, *Borrelia burgdorferi*, *Borrelia californiensis*, *Borrelia carolinensis*, *Borrelia caucasica*, *Borrelia coriaceae*, *Borrelia crocidurae*, *Borrelia dugesii*, *Borrelia duttonii*, *Borrelia garinii*, *Borrelia graingeri*, *Borrelia harveyi*, *Borrelia hermsii*, *Borrelia hispanica*, *Borrelia japonica*, *Borrelia kurtenbachii*, *Borrelia latyschewii*, *Borrelia lonestari*, *Borrelia lusitaniae*, *Borrelia mayonii*, *Borrelia mazzottii*, *Borrelia merionesi*, *Borrelia microti*, *Borrelia miyamotoi*, *Borrelia parkeri*, *Borrelia persica*, *Borrelia queenslandica*, *Borrelia recurrentis*, *Borrelia sinica*, *Borrelia spielmanii*, *Borrelia tanukii*, *Borrelia theileri*, *Borrelia tillae*, *Borrelia turcica*, *Borrelia turdi*, *Borrelia turicatae*, *Borrelia valaisiana*, *Borrelia venezuelensis*, *Borrelia vincentii*, and *Candidatus Borrelia texasensis*.

8. The method of claim 7, wherein the one or more *Borrelia* species are selected from the group consisting of: *Borrelia burgdorferi*, *Borrelia garinii*, *Borrelia mayonii*, and *Borrelia afzelii*.

9. The method of claim 1, further comprising detecting in the sample a *Babesia* species, an *Ehrlichia* species, a *Bartonella* species, *Francisella tularensis*, *Yersinia pestis*, *Staphylococcus aureus*, *Anaplasma phagocytophilum*, Enterovirus, Powassan and deer tick virus, *Rickettsia* species, and/or *Influenza* by subjecting the DNA and/or RNA from the sample to a second PCR amplification reaction using primer pairs containing sequences selected from the group consisting of:
   SEQ ID NOS: 49-55 for detection of *Anaplasma phagocytophilum*;
   SEQ ID NOS: 56-59 for detection of an *Ehrlichia* species;
   SEQ ID NOS: 78-86 for detection of Enterovirus;
   SEQ ID NOS: 87-88 for detection of *Staphylococcus aureus*;
   SEQ ID NOS: 89-90 for detection of *Influenza*;
   SEQ ID NOS: 91-94 for detection of *Yersinia pestis*;
   SEQ ID NOS: 95-96 for detection of *Francisella tularensis*;
   SEQ ID NOS: 105-106 for detection of a *Bartonella* species;
   SEQ ID NOS: 107-108 for detection of a *Babesia* species;
   SEQ ID NOS: 294-310 for detection of a *Rickettsia* species; and
   SEQ ID NOS: 311-314 for detection of a Powassan and deer tick virus.

10. The method of claim 1, wherein the sample is selected from the group consisting of: whole blood, serum, plasma, buffy coat, and connective tissue.

11. The method of claim 1, wherein the subject is a human.

12. The method of claim 1, wherein an amplification product from the *Borrelia* genus-wide assay targeting at least one region of the flagella subunit B (flaB) gene is mapped to the reference library of known *Borrelia* sequences to identify *Borrelia* species that cause Lyme Disease and *Borrelia* species that do not cause Lyme Disease.

13. The method of claim 1, wherein an amplification product from the *Borrelia* genus-wide assay targeting at least one region of *Borrelia* 16S rRNA is mapped to the reference library of known *Borrelia* sequences to identify *Borrelia* species that cause Lyme Disease and *Borrelia* species that do not cause Lyme Disease.

14. The method of claim 2, wherein the sample is obtained from a human subject and comprises human tissue and/or additional living organisms.

* * * * *